United States Patent
Abadi et al.

(10) Patent No.: US 11,984,211 B2
(45) Date of Patent: May 14, 2024

(54) SYSTEM AND METHOD FOR UTILIZATION OF DATA FROM REMOTE REGULATION AND MONITORING OF DRUG DELIVERY

(71) Applicants: Isaac Abadi, Atlanta, GA (US); Adam Verga, Atlanta, GA (US); Jacob Banov, Atlanta, GA (US); Daniel Liubovich, Shrewsbury, MA (US); Brandon Kleber, Atlanta, GA (US)

(72) Inventors: Isaac Abadi, Atlanta, GA (US); Adam Verga, Atlanta, GA (US); Jacob Banov, Atlanta, GA (US); Daniel Liubovich, Shrewsbury, MA (US); Brandon Kleber, Atlanta, GA (US)

( * ) Notice: Subject to any disclaimer, the term of this patent is extended or adjusted under 35 U.S.C. 154(b) by 197 days.

(21) Appl. No.: 17/737,940

(22) Filed: May 5, 2022

(65) Prior Publication Data
US 2023/0065458 A1    Mar. 2, 2023

Related U.S. Application Data

(63) Continuation-in-part of application No. 17/461,837, filed on Aug. 30, 2021, now abandoned.

(51) Int. Cl.
*G06Q 10/00*     (2023.01)
*A61M 5/50*      (2006.01)
(Continued)

(52) U.S. Cl.
CPC .......... *G16H 20/13* (2018.01); *A61M 5/5086* (2013.01); *A61M 15/08* (2013.01); *G16H 40/20* (2018.01);
(Continued)

(58) Field of Classification Search
CPC ......... H01L 27/0922; H01L 21/823807; H01L 21/823871; H01L 29/0665;
(Continued)

(56) References Cited

U.S. PATENT DOCUMENTS 4,830,224 A     5/1989   Brison
5,064,122 A    11/1991   Kamishita
(Continued)

FOREIGN PATENT DOCUMENTS

AU     2017248205 A1    11/2018
CA        2364009 C      2/2007
(Continued)

OTHER PUBLICATIONS

Timothy Aungst, "The Big List of Digital Health Medication List Companies", Nov. 2, 2018, [retrieved on May 26, 2020, Retrieved from the Internet <URL: https://www.pharmacytimes.com/contributor/timothy-aungst-pharmd/2018/ 11/the-big-list-of-digital-healthmedication-list-companies>, 4 pages, United States of America.
(Continued)

*Primary Examiner* — Tai T Nguyen

(57) ABSTRACT

Aspects and embodiments of the present invention generally include a device for patient self-administration of a prescribed medication. The device makes available for administration the precise quantity of medication constituting a dose at times designated by a health care provider (HCP). Preferably, the device also detects and transmits information to a remote management system accessible to the HCP, including detected attempts to tamper with the device. Advantageously, HCPs may render oversight and control over the device and its use to mitigate risks associated with patients self-administering medication without in-person supervision. This control may include establishing prerequisites the patient must meet prior to a dose being made available, or remote deactivation of the device. This oversight by the HCP may include patient-specific and aggregate data analysis for optimization of treatment or evaluation of the safety and efficacy of a treatment. Furthermore, this oversight may be conducted via a web-based interface.

12 Claims, 25 Drawing Sheets

(51) Int. Cl.
  *A61M 15/08* (2006.01)
  *G16H 20/13* (2018.01)
  *G16H 40/20* (2018.01)
  *G16H 40/67* (2018.01)
(52) U.S. Cl.
  CPC ......... *G16H 40/67* (2018.01); *A61M 2205/13* (2013.01); *A61M 2205/3553* (2013.01); *A61M 2205/3584* (2013.01); *A61M 2205/50* (2013.01)
(58) Field of Classification Search
  CPC ......... H01L 29/42392; H01L 29/78696; H01L 29/42372; B82Y 10/00
  USPC .......................................................... 705/2
  See application file for complete search history.

(56) References Cited

U.S. PATENT DOCUMENTS

| | | | |
|---|---|---|---|
| 5,331,954 | A | 7/1994 | Rex |
| 5,437,267 | A | 8/1995 | Weinstein |
| 6,948,492 | B2 | 9/2005 | Wermeling |
| 7,100,601 | B2 | 9/2006 | Bruna |
| 7,743,923 | B2 | 6/2010 | Conley |
| 8,060,249 | B2 | 11/2011 | Bear |
| 8,552,868 | B1 | 10/2013 | Ferguson |
| 8,555,878 | B2 | 10/2013 | Djupesland |
| 8,744,620 | B2 | 6/2014 | Shavelsky |
| 8,786,272 | B2 | 7/2014 | Carapelli |
| 8,817,258 | B2 | 8/2014 | Whalley |
| 8,849,449 | B2 | 9/2014 | Waugh |
| 8,978,647 | B2 | 3/2015 | Djupesland |
| 9,173,837 | B2 | 11/2015 | Hillis |
| 9,361,780 | B2 | 6/2016 | Burke |
| 9,452,272 | B2 | 9/2016 | Djupesland |
| 9,456,959 | B2 | 10/2016 | Reddy |
| 9,468,729 | B2 | 10/2016 | Sutherland |
| 9,492,357 | B2 | 11/2016 | MacVittie |
| 9,550,031 | B2 | 1/2017 | Van Sickle |
| 9,953,140 | B2 | 4/2018 | McLean |
| 10,010,678 | B2 | 7/2018 | Schildt |
| 10,019,555 | B2 | 7/2018 | Manice |
| 10,065,788 | B2 | 9/2018 | Fagen |
| 10,071,022 | B2 | 9/2018 | Park |
| 10,176,663 | B2 | 1/2019 | King |
| 10,220,166 | B2 | 3/2019 | Van Sickle |
| 10,287,066 | B2 | 5/2019 | Hatton |
| 10,292,642 | B2 | 5/2019 | Euliano |
| 10,332,623 | B2 | 6/2019 | Edwards |
| 10,433,787 | B2 | 10/2019 | Kanukurthy |
| 10,441,194 | B2 | 10/2019 | Robertson |
| 10,441,511 | B2 | 10/2019 | Hamilton |
| 10,452,816 | B2 | 10/2019 | Kidd |
| 10,517,756 | B2 | 12/2019 | Andino |
| 10,555,874 | B2 | 2/2020 | Feng |
| 10,803,149 | B2 | 10/2020 | Kalyanpur |
| 2007/0287753 | A1 | 12/2007 | Charney |
| 2010/0328099 | A1 | 12/2010 | Wachman |
| 2011/0166700 | A1 | 7/2011 | Dunn |
| 2014/0236616 | A1 | 8/2014 | Oberfest |
| 2014/0278210 | A1* | 9/2014 | Krauss ............... G01B 21/04 |
| | | | 702/150 |
| 2014/0278510 | A1 | 9/2014 | McLean |
| 2016/0074283 | A1 | 3/2016 | Aggarwal |
| 2016/0357914 | A1* | 12/2016 | Morris ............... G16H 10/60 |
| 2017/0182258 | A1 | 6/2017 | Michael |
| 2017/0326034 | A1 | 11/2017 | Lewis |
| 2018/0079586 | A1 | 3/2018 | Burton |
| 2019/0240430 | A1 | 8/2019 | Jackson |
| 2019/0348165 | A1 | 11/2019 | Saint |
| 2019/0392937 | A1 | 12/2019 | Mensinger |
| 2020/0009081 | A1 | 1/2020 | Wang |
| 2021/0059903 | A1 | 3/2021 | Crowley |
| 2021/0236752 | A1 | 8/2021 | Botha |
| 2021/0268217 | A1 | 9/2021 | Botha |

FOREIGN PATENT DOCUMENTS

| | | |
|---|---|---|
| CA | 2976259 A1 | 8/2016 |
| CA | 2438977 C | 7/2018 |
| EP | 2037990 B1 | 6/2012 |
| EP | 2653183 B1 | 3/2015 |
| GB | 2570509 B | 1/2020 |
| WO | WO2005086852 A2 | 9/2005 |
| WO | WO2013025520 A2 | 2/2013 |
| WO | WO2021127335 A1 | 6/2021 |

OTHER PUBLICATIONS

Adherium, "Proven Health Technologies", 2020, [retrieved on May 26, 2020], Retrieved from the Internet <URL: https://www.adherium. corn/technology/>, 4 pages, New Zealand.

E-pill, "MedSmart", 2020, [retrieved in 2020], Retrieved from the Internet <URL: https://www.epill.com/medsmart.html>, 3 pages, United States of America.

MedVault, "About MedVault", 2020, [retrieved on 2020], Retrieved from the Internet <URL: https://medvault.wordpress.corn/about/about-medvault/>, 1 page, United States of America.

Aavia, "aavia", 2020, [retrieved on Jun. 6, 2020], Retrieved from the Internet <URL: https://aavia.io/>, 4 pages, United States of America.

Janssen Pharmaceuticals, Inc., "About Spravato", 2019-2020, [retrieved on 2019], Retrieved from the Internet <URL: https://www.spravato.com/what-is-spravato>, 9 pages, United States of America.

Popit, "Popit", 2020, [retrieved on Jun. 6, 2020], Retrieved from Internet <URL: https://popit.io/>, 7 pages, Finland.

AptarGroup, Inc., "E-Lockout", 2020, [retrieved on 2020], Retrieved from Internet <URL: https://pharma.aptar.corn/en-us/dispensingsolutions/e-lockout.html>, 1 page, United States of America.

Pillpresso, "pillpresso", 2020, [Retrieved on Jun. 6, 2020], Retrieved from Internet <URL: https://pillpresso.corn/>, 5 pages, United States of America.

Mamta Kapoor, A review of intranasal formulations for the treatment of seizure emergencies, Journal of Controlled Release, Sep. 10, 2016, 147-159, vol. 237, Elsevier B.V., USA.

Nemera, "Safe'n'Spray™: the smart electronic concept device with locking features," 2019-2020, [retrieved in 2019], Retrieved from Internet <URL: https://www.nemera.net/products/ear-nasal-throat/safenspray/>, 1 page, France.

Jon Hamilton, "FDA Approves Esketamine Nasal Spray for Hard-To-Treat Depression", 2019-2020, [retrieved in 2019], Retrieved from Internet <URL: https://www.npr.org/sections/health-shots/2019/03/05/700509903/fda-clears-esketamine-nasal-spray-for-hard-totreat depression>, 4 pages, United States of America.

Per Gisle Djupesland, Nasal drug delivery devices: characteristics and performance in a clinical perspective-a review, Drug Delivery and Translational Research, Oct. 18, 2012, 42-62, vol. 3(1), National Center for Biotechnology Information, U.S. National Library of Medicine, Bethesda, MD.

Ulrika Westin Espefalt, Olfactory Transfer of Analgesic Drugs After Nasal Administration, Digital Comprehensive Sununaries of Uppsala Dissertations from the Faculty of Pharmacy 55, Apr. 19, 2007, Uppsala Universitet, Sweden.

Bjorn Jansson, Models for the Transfer of Drugs from the Nasal Cavity to the Central Nervous System, Comprehensive Sununaries of Uppsala Dissertations from the Faculty of Pharmacy 305, Jan. 30, 2004, Uppsala Universitet, Sweden.

Medminder Sy stems, Inc., "Locked Pill Dispenser", 2019, [retrieved on Feb. 24, 2019], Retrieved from Internet <URL: https://www.medminder.com/pill-dispenser/locked-pill-dispenser/>, 5 pages, United States of America.

Degenhard Marx, Multi-Dose Container for Nasal and Ophthalmic Drugs: A Preservative Free Future?, Aptar, Dec. 7, 2011, 509-524, InTechOpen, Germany.

Limor Wainstein, "Cloud-Based Telehealth Defined: Advantages, Applications, and Security", Jun. 26, 2018, [retrieved on Feb. 24, 2019], Retrieved from internet <URL: https://telemedicine.arizona.

(56) References Cited

OTHER PUBLICATIONS edu/blog/cloud-based-telehealth-defined-advantages-applicationsand-security>, University of Arizona Telemedicine Program, Arizona, USA.

Kiao Inthavong, Optimising nasal spray parameters for efficient drug delivery using computational fluid dynamics, Computers in Biology and Medicine, 713-726, vol. 38(6), Jun. 2008, Elsevier, Australia.

Raepak LTD, "Nasal Spray Pump—Clip Lock", 2019, [retrieved on Feb. 24, 2019], retrieved from internet <URL: https://www.raepak.com/product/nasal-spray-pump-clip-lock/>, 5 pages, United Kingdom.

Philip Chen, Sinus Penetration of a Pulsating Device Versus the Classic Squeeze Bottle in Cadavers Undergoing Sinus Surgery, Annals of Otology, Rhinology & Laryngology, 9-13 , 126(1), Sep. 29, 2016, San Antonio, Texas.

International Search Report and Written Opinion of the International Searching Authority, for corresponding PCT Application US2020/036858, dated Oct. 15, 2020.

\* cited by examiner

SYSTEM AND METHOD FOR UTILIZATION OF DATA FROM REMOTE REGULATION AND MONITORING OF DRUG DELIVERY

RELATED APPLICATIONS

The present application claims the benefit of U.S. Provisional Patent Application 62/859,138, filed Jun. 9, 2019. The present application is a continuation-in-part of U.S. patent application Ser. No. 17/461,837, filed Aug. 30, 2021, now abandoned, which is a continuation of Ser. No. 16/897,232 filed Jun. 9, 2020, now issued as U.S. Pat. No. 11,103,422, which claims the benefit of U.S. Provisional Patent Application 62/859,138, filed Jun. 9, 2019.

BACKGROUND

Field of the Invention

The present application is directed generally toward medication administration, and in particular, to patient self-administration of a prescribed medication.

Related Art

Few technologies exist that allow for health care practitioners to have optimal oversight over patients when the patients are not in their immediate care. This lack of oversight is most evident in patient use of prescription medications. A substantial percentage of patients fail to fill their prescriptions, and a substantial percentage of those that fill their prescriptions fail to take the medications as prescribed. And of those patients that follow the prescription, many fail to do so continuously or consistently. This is further compounded by the misuse of prescription medications, either due to abuse or error. As a result, the administration of the more acutely dangerous prescription medications as well as the administration of medications to treat a serious medical condition, typically require the medication to be administered under the immediate care of a health care practitioner.

SUMMARY

Aspects and embodiments of the present invention generally include a system comprising a device for patient self-administration of a prescribed medication. The total quantity of doses to be contained in the device, the quantity of prescribed medication comprising each individual dose, and the dosing schedule, are controlled solely by a health care provider (HCP) such as the patient's physician. In accordance with a prescribed dosing schedule, the device makes available for administration the precise quantity of prescribed medication constituting an individual dose. Patient access to the medication as well as patient control of the device is limited solely to the aspects of the device necessary to administer the available dose. The device also detects and transmits relevant device information to a remote management system accessible to the HCP, including detected attempts to alter, access, control or otherwise tamper with the device beyond its prescribed use, and detected events of self-administration. The device may deliver the prescribed medication in any number of possible delivery mechanisms, for example a nasal spray, inhaler, transdermal patch, intravenous injection, intramuscular injection, or eye drop, and in any number of possible forms, for example aerosol, mist, vapor, smoke, powder, or gel. The device is further configured to send monitored parameters to, and receive control commands from, a remote server of the system on which a patient management software is executing, at least in part.

The functionality of the system works to enable the patient's physician or other HCP to remotely monitor and control the device. HCP regulatory commands include, for example, commands to alter the dosing quantity and/or schedule, create or modify prerequisites for making a dose available, to permit access to the device for prescription refills, as well as to cease operability of the device should it be tampered with or reported lost or stolen. The system is configured to provide the HCP with access to relevant controls and collected data as well as analysis of this data, for example through an interface such as a web-based application. This interface can be designed for different categories of HCPs, for example private practices, hospitals, and assisted living facilities, each of which having an interface customized to their individual needs. The analysis may be of data from one or more patients and may be collected via the device, patient, HCP, or external source. Some embodiments of the system for example comprise a patient interface such as a smartphone application for data input for example health surveys, as well as to give the patient oversight and notification tools to improve compliance. The results of the analysis of this data can then be utilized by the HCP, patient, device, or external system such as a pharmacy, hospital, insurance company, government, drug manufacturer, device manufacturer, healthcare software developer, research institution, or electronic medical records system. Some examples of data analysis include compliance tracking, medical conditions, side-effects, trends in survey results, treatment progress, data from various sensors, correlations and trends between variables, comparisons between drugs, and comparisons between clinical trial groups. This analysis can be presented to the HCP, and allow them to use it to monitor patient compliance, optimize treatment, view diagnostic data, check for health risks, assess treatment efficacy and safety, and perform a cost-benefit analysis of the treatment.

Methods for managing administration of a single dose of a medication to a patient utilizing a remotely regulated and monitored patient-controlled drug delivery device, configured to store a plurality of medication doses, are also disclosed herein. This method includes the establishment of treatment parameters, ensuring one or more prerequisite requirements set by the HCP have been fulfilled, making available a single dose of the plurality of medication doses conditioned on said prerequisite requirements fulfillment indication, delivering the available single dose of medication to the patient upon the reception of patient control actions, receiving treatment feedback related to patient use of the device, and conducting analysis on said treatment feedback. These treatment parameters can be modified through one or more mechanisms, which may include manually by the HCP in real-time mid-prescription, manually by the HCP upon new prescription, automatically by software component of the system based on data, and manually by patient with pre-approval of HCP. These prerequisite requirements for a dose to be made available may include for example successful passing of a user identification test by the patient, agreeing to policies by the patient, confirming the patient's readiness and ability to use the device to self-administer the medication, successful passing of a health status test by the patient, the absence of a detected tamper event, a preset time has elapsed since the prior self-administration by the patient, being more than a minimum temporal proximity to the following scheduled dose, reception by device of updated treatment parameters, successful patient adherence to dose schedule up to present, active communication between patient and HCP, and successful and timely data transfer between system components. Some examples of potential treatment feedback include confirming successful self-administration of the single dose of medication by the patient, reporting of problem by the patient, data collected by the use of at least one survey by the patient, data collected by the device regarding a self-administration event occurrence, data collected by the device regarding patient health parameters, data collected by external devices, and data collected by the HCP through communication with the patient. The making available and subsequent delivery of a single dose could possibly be confirmed through any number of mechanisms, medication flow sensor, medication volume sensor, medication weight sensor, medication height sensor, medication location sensor, delivery interface state sensor, patient control action sensor, medication separation mechanism feedback, patient blood content sensor, and algorithms within the system.

In addition, methods for delivering a single dose of a medication to a patient by a remotely regulated and monitored patient-controlled drug delivery device configured to store a plurality of medication doses are disclosed herein, including receiving treatment parameters, receiving an indication that one or more prerequisite requirements set by the HCP have been fulfilled, making available a single dose of the plurality of medication doses conditioned on said prerequisite requirements fulfillment indication, delivering the available single dose of medication to the patient upon the reception of the patient control actions, storing data regarding use, and transmitting data regarding use. In one embodiment, the storing of data regarding use is initiated in the absence of connectivity to the internet, and that upon the restoration of this connection, this data is transmitted. This data regarding use could include administration events, fluid levels or quantities, fluid flow rates, battery charge, access hatch status, tamper events, device location, network connection status, patient identification data, and patient health parameter data.

BRIEF DESCRIPTION OF THE DRAWINGS

The features and advantages of the described aspects and embodiments of the present invention will be more clearly appreciated from the following detailed description, when taken in conjunction with the accompanying drawings. The accompanying drawings are not drawn to scale. In the drawings, each identical or nearly identical component that is illustrated in various figures is represented by a like or similar reference numeral or descriptor. For purposes of clarity, not every component may be labeled in every drawing. The drawing figures are.

DETAILED DESCRIPTION

Figure 1:
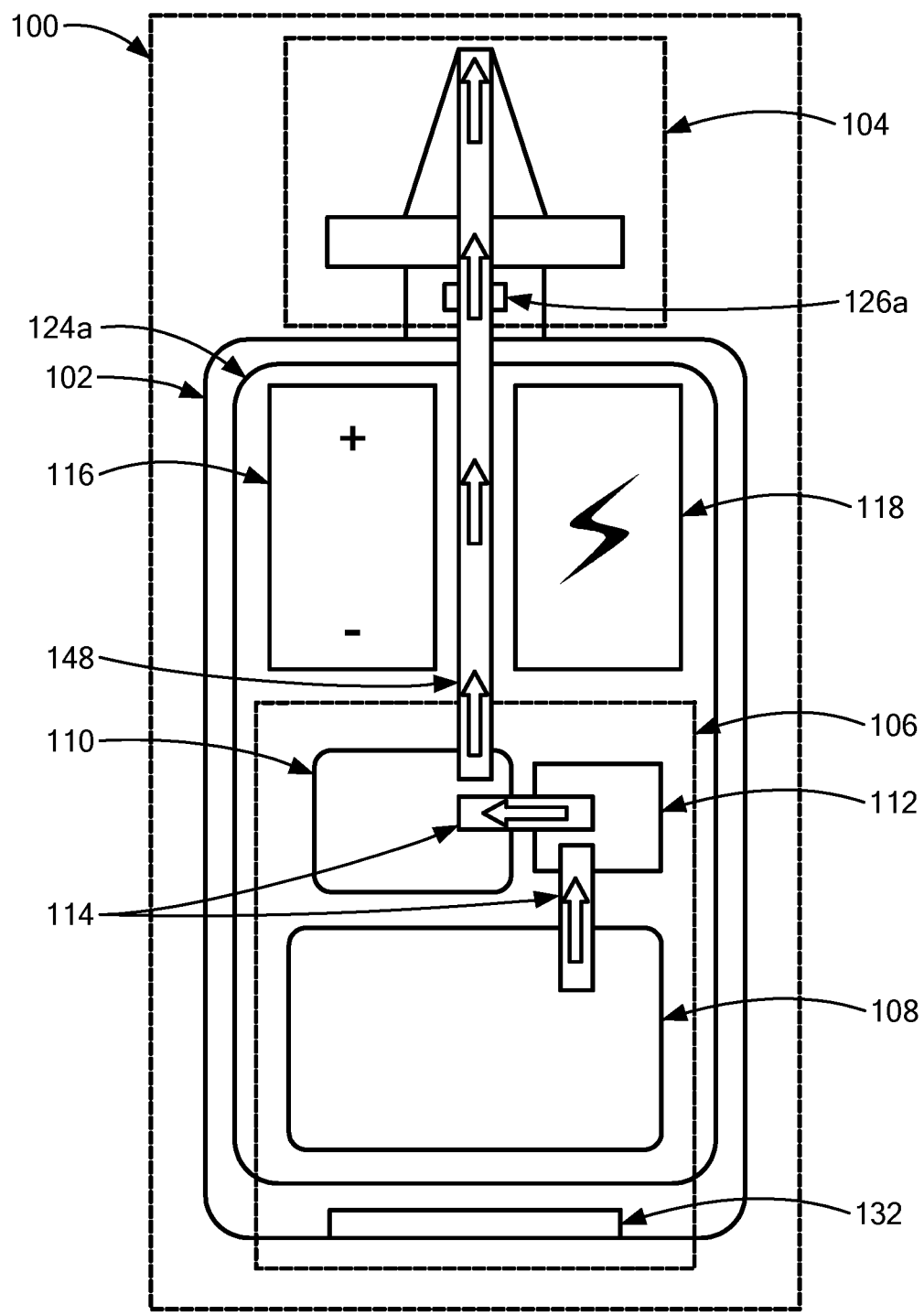
FIG. 1 is a schematic block diagram of one embodiment of a medication self-administration device.

Aspects and embodiments of the present invention generally include a device for patient self-administration of a prescribed medication. The total quantity of doses to be contained in the device, the quantity of prescribed medication comprising each individual dose, and the dosing schedule, collectively referred to as prescription parameters, are determined and controlled solely by a health care provider (HCP) such as the patient's physician. In accordance with a prescribed dosing schedule, the device makes available for administration the precise quantity of prescribed medication constituting an individual dose. Patient access to the medication as well as patient control of the device is limited solely to the aspects of the device necessary to administer the available dose; that is, the patient has no control over the prescription parameters utilized by the device; that is, the quantity of a dose, the availability of individual doses, the schedule at which the doses are made available to the patient, nor the prescribed medication itself which is contained in the device. Preferably, the device also has a monitored subassembly which detects and transmits relevant device information to a remote management system accessible to the HCP, including detected attempts to alter, access, control or otherwise tamper with the device beyond its prescribed use. Advantageously, HCPs are provided with the capability to render sufficient oversight and control over the device and its use to mitigate the risks associated with patient self-administration of potentially dangerous or abusable medication without direct, in-person supervision.

Aspects and embodiments of the present invention are further directed to a system in which the functionality of the device is remotely monitored and controlled by the patient's physician or other HCP. HCP regulatory commands include, for example, commands to alter the dosing quantity and/or schedule, to permit access to the device for prescription refills, as well as to cease operability of the device should it be tampered with or reported lost or stolen.

The device is further configured to send monitored parameters to, and receive control commands from, a remote server of the system on which a patient management software is executing, at least in part. This server is configured to provide the HCP with access to relevant data and controls. Some embodiments of the system further comprise a patient interface for data input, oversight and notifications. Some embodiments of the system also further comprise additional external devices for any number of functions, some examples include biometric sensors, user-identifying sensors, and global positioning systems.

Other embodiments include additional features to monitor patient biometrics directly or indirectly via third-party medical equipment. In such embodiments, the device may be programmed by the HCP to alter the dosing parameters or device functionality based on the availability and specified range of such biometric values. Advantageously, such embodiments provide additional levels of security and safety, ensuring that the device is utilized by the intended people, and that the patient's daily health condition does not warrant a change or cessation of the prescription.

As noted, aspects of the present invention are directed to a device for use by a patient to self-administer a prescribed medication, generally referred to herein as a medication self-administration device. Preferred forms in which a prescribed medication is to be administered depend on numerous factors, such as the bioavailability in a given form, location of the target area, and intended therapeutic effects. As such, various embodiments of the device are each configured to be used by a patient to administer a prescribed medication in the prescribed form and in accordance with the recommended method of delivery.

These delivery methods include, for example, spray for the delivery of mist, which is typically delivered to the nasal passage, atomizer for the delivery of mist or vapor, typically delivered to the nasal passages and/or the lungs, and more specifically, a nebulizer which is often used for the delivery of a mist to the lungs. Some embodiments may deliver a fluidic medication via intramuscular or intravenous injection, while other embodiments may have the medication in aerosol form for inhalation, for example using an inhaler. Furthermore, larger droplets or even a stream of liquid may also be administered in certain embodiments, for example eye drops. It should also be appreciated that as used herein, the term "self-administration" refers generally and collectively to direct and indirect administration of a prescribed medication. For example, large droplets or a liquid stream of a prescribed medication may be administered directly to the nasal passage in one embodiment of the device, or administered indirectly using the same or different embodiment of the device. An example of indirect delivery methods include but are not limited to the dispensing of droplets or a liquid stream into an external container to be titrated; that is, mixed with water, prior to being ingested by, for example, drinking. Other examples of indirect delivery methods include the spraying of a mist into an external holding chamber prior inhaling and the dispensing of solid-phase medication for ingestion or otherwise.

Further examples of possible forms in which the medication could be delivered, in addition to those examples noted above, include suspension, colloid, solution, smoke, powder, gel, paste, and cream. Some such suspensions may comprise solid in liquid, solid in gas, liquid in gas, or any combination thereof. The form in which the medication is in prior to delivery, and that in which it is in upon delivery, may be reliant on the specific pharmaceutical formulation being used and the specific conditions of the patient(s) for which an embodiment is targeted to treat. Such medication may include any number of components, for example active ingredients and preservatives, and may be manufactured and combined in any number of forms, for example aqueous solution and mixture of liquids.

Further possible delivery methods include intramuscular, subcutaneous, intradermal, and transdermal delivery. These delivery methods may utilize injection, infusion, and any mechanism which allows for such delivery, including but limited to patches and other devices which adhere to the patient's skin. Some such devices both deliver medication while also monitoring patient parameters, and such measurements may be used to influence when and how much medication is made available. Some adhesive embodiments utilize an array of needles, for example microneedles, while others utilize only a single needle. Other embodiments utilize vaporization, which may include, for example, the vaporization of a liquid, such as those comprising vegetable glycerin and/or propylene glycol, and vaporization of a solid, such as those comprising psychoactive herbs. Other delivery methods involve contact resulting in the absorption through the skin without the aid of needles.

Aspects and embodiments of the present invention will be described in connection with an exemplary medication self-administration device, a nasal delivery device configured to deliver a prescribed fluid medication in an aerated form to a nasal cavity. It should be appreciated, however, that in alternative embodiments the medication self-administration device may be configured to deliver other forms of a prescribed medication to other target areas or indirectly, as noted above.

Figure 5A:
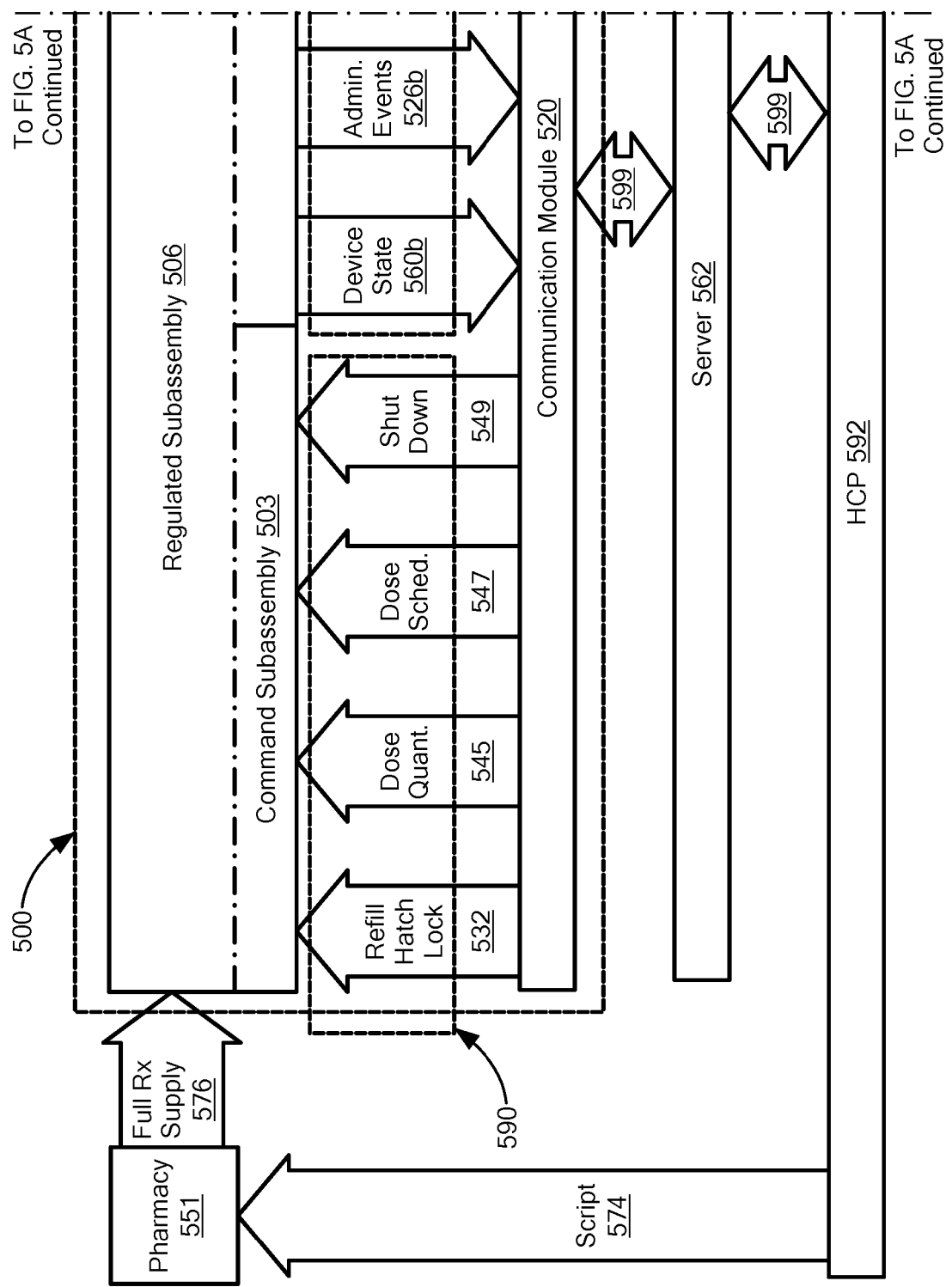
FIG. 5A is a functional block diagram of an exemplary system of the present invention.

FIG. 5A is a functional block diagram of an exemplary system of the present invention. System 501 includes an exemplary medication self-administration device 500. Device 500 receives prescribed medication 576, typically from a pharmacy 551. As noted, The total number of doses contained in a medication self-administration device of the present invention is determined and controlled solely by a health care provider, shown as HCP 592 in FIG. 5A. Such a health care provider may be, for example, the patient's physician, a physician's assistant (PA), nurse practitioner (NP), and/or others that operate under the direction and supervision of the patient's physician.

HCP 592 provides a prescription 574 to pharmacy 551 specifying the requisite prescription parameters so that pharmacy 551 is able to dispense the total quantity of medication to device 500 for a patient 594. This quantity of medication, referred to herein as a full Rx supply 576 of such medication, is delivered directly into device 500 by pharmacy 551. It is anticipated that the form of the prescribed medication is likely to be a fluid. As such, prescribed medication 576 may be poured or otherwise fluidically transferred directly, or via an attached tubing, into a chamber in the device via an appropriately configured delivery port. Alternatively, pharmacy 551 may inject the prescribed medication through a silicone seal. In alternative embodiments, full Rx supply 576 may be provided in a sealed container which is physically inserted through an aperture into a compartment of device 500. Whether such access is provided by a port, injection seal, aperture or other structure or mechanism, device 500 preferably includes a secure hatch through which such port, injection seal or aperture is accessed should the device be filled by pharmacy 551 or HCP 592. In some embodiments, device 500 is filled with medication by the manufacturer before distribution, preferably the case for disposable embodiments of device 500.

Device 500 includes a regulated fluidics subassembly 506 configured to receive and securely store full Rx supply 576 of a prescribed medication, and to make available for administration the precise prescribed individual dose of the stored medication, referred to herein as metered dose 512. Regulated subassembly 506 is responsive to remotely generated control signals 590 generated by HCP 592 to manage the operation of—that is, to regulate—device 500. As such, control signals 590 are sometimes referred to herein as regulatory commands or regulatory control signals. Control signals 590 may be transmitted directly to device 500 from HCP 592, such as through a networked computer local to HCP 592 which is communicably connected to device 500, or indirectly by HCP 594, such as by invoking software executing on server 562 to generate such commands 590. The networked communications between HCP 592 and server 562, and between server 562 and device 500, are schematically depicted in FIG. 5A as arrows 599.

Remotely generated control signals 590 include, for example, the noted prescription parameters such as dose quantity 545 and dose schedule 547 (the total quantity of prescribed medication being specified or derived from prescription parameters contained in prescription 574, as noted above). Other control signals 590 include, for example, device shut-down control signal 549, which will cause device 500 to cease operation.

Command subassembly 503 of device 500 generates signals to control regulated subassembly 506 in response to regulatory commands 590 generated by HCP 592 and transmitted to device 500. The outputs of command subassembly 503 may take on any form suitable for the controlled components. For example, command subassembly 503 may generate electronic signals, may shift the voltage on certain input pins of a component, may write data to a microcontroller memory of a component, and so on. As such, for ease of description, the outputs and actions of command subassembly 503 are also referred to herein as command signals 590.

In some embodiments, as mentioned above, the restricted components of the regulated subassembly may be accessible to a party that is not the patient, for example, a HCP, manufacturer, distributor, etc. for reasons which may include but are not limited to refilling, refurbishing, and maintenance. In those embodiments in which device 500 is to be refilled, regulatory control commands 590 preferably include a hatch lock command 532. HCP 592 directly or indirectly generates a hatch lock command 532 to unlock such a hatch so that pharmacy 551 may access device 500 and refill the prescription. Although in FIG. 5A hatch lock command 532 is shown as being remotely generated by HCP 592, it should be appreciated that in alternative embodiments, hatch lock command 532 may be generated by pharmacy 551 or other HCP, depending on the protocols established to ensure safe administration of the prescribed medication.

As noted, in response to a prescribed dosing schedule 574, regulated subassembly 506 makes available for administration metered dose 512 which is the precise individual dose of the medication prescribed by HCP 592 in dose quantity 545. A medication delivery interface 504, responsive to patient control actions 553, retrieves, receives or otherwise accesses metered dose 512, and delivers metered dose 512 of the prescribed medication to patient 594 as administered dose 582.

As noted, aspects of the present invention are directed to a device for use by a patient to self-administer a prescribed medication. Various embodiments of device are each configured to be used to administer a prescribed medication in a prescribed form or state (liquid, gas, mist, etc.) and in accordance with the recommended or required delivery method (nasal spray, inhaler, injection, etc.) Depending on the quantity of medication contained in an individual metered dose 512, the form of the administered medication, the specified delivery method, the characteristics of the target delivery location, as well as the conditions and characteristics of patient 594, administered dose 582 may be delivered in a series of two or more applications 583 to patient 594. For example, patient 594 may be unable to tolerate, swallow, inhale or otherwise therapeutically accept a single application 582 of dose quantity 545 of medication at one time. Embodiments of device 500 employed under such circumstances preferably comprises a device interface 504 configured to enable patient 594 to control, via patient actions 553, the portion of metered dose 512 which is to be delivered in each successive application 583.

A monitored subassembly 522 comprises passive and/or active components described below to detect device operations and operational states, which may include but are not limited to data regarding measured fluid levels or quantities, detected physical shocks, detected device modification or disassembly attempts, detected or derived fluid escape or leakage, and other device parameters. Some embodiments of the monitored subassembly may further be configured to detect patient parameters, such as biometrics and/or user identity. It should be appreciated that such measuring, sensing, detecting, etc., may be conducted by sensors located in regulated subassembly 506 and delivery interface 504 as well as other components of device 500 such as its housing, etc. Alternatively or additionally, such monitored device parameters may be retrieved from the memory in, or interpreted based on signals generated by, components included in subassembly 506 and interface 504. To reflect this flow of information, the boundaries between monitored subassembly 522 and regulated subassembly 506 and delivery interface 504 are depicted in FIG. 5A as being porous, as shown by dashed lines in the figure.

Monitored subassembly 522 is further configured to store and transmit such monitored device parameters to a remote server 562 for processing by a patient management software executing at least in part on server 562, and/or for access by/presentation to HCP 592. Such transmission may occur immediately, in accordance with a predetermined schedule or in response to a request for such data by server 562. The functions and operations performed in system 501 to transmit and process monitored device parameters are collectively and generally referred to herein as remote monitoring 588.

In the embodiment of system 501, the device parameters that are gathered by monitored subassembly 522 and transmitted to server 562 include device operational states 560b such as the current charge of an onboard rechargeable battery, the position or state of the refill hatch, if any, the position, orientation, etc., of any electromechanical components of regulated subassembly 506, the functional health of such device components, etc.

Monitored device parameters of system embodiment 501 also include, in certain embodiments, fluid levels 528b of the medication contained in device 500. If such medication is distributed in regulated subassembly 506, then the fluid levels at each location of the medication can be monitored and included in fluid levels 528b. For device 500 embodiments configured for medication forms other than fluids, this parameter could be a measure of weight, volume, quantity, or any other metric that could indicate an amount of medication in a given location within device 500.

Administration event data 526b collected by monitored subassembly 522, in some nasal spray configurations of device 500, may be collected by one or more contact sensors located so as to detect when the nozzle has been depressed, and/or a fluid flow sensor or fluid level sensor. In other such embodiments, a sensor detects the distance the plunger travels. In some embodiments of device 500 which are intended for use with medications in forms other than a fluid, other types of sensors may be used which serve the function of detecting an administration event. Such detection methods may include but are not limited to detection of changes in mass within device 500, disruptions to an optical beam, an imaging sensor, or any other method which may serve this purpose.

In embodiments of device 500, monitored device parameters include tamper events 524b reflecting any sensed or detected event, the occurrence of which may be as a result of an attempted unauthorized use of device 500. For example, in some embodiments, device 500 includes one or more accelerometers to detect the application of forces greater than those that may occur during everyday use. Physical shocks of such magnitude indicate potential attempted breach of the device suitable for reporting to server 562 and HCP 592. Other embodiments may include a circuit network whose electrical feedback would change after physical manipulation or contact. Whether due to intentional tampering or accidental handling, such sensor(s) may be activated whenever the functionality of device 500 has possibly been compromised. This sensor could be of any nature which effectively accomplishes this task. In other embodiments, monitored subassembly 522 includes electronic contacts to detect any adjustment of mated parts. Attempts to access the prescribed medication in device 501 by disassembling the device will be detected by such contacts and reported to server 562 and HCP 592. In other embodiments, monitored subassembly 522 includes piezoelectric sensors to measure changes in strain or force in regulated subassembly 506, processing and interpreting signals from such sensors to determine potential tampering or unauthorized access. Some other embodiments of device 500 may detect tampering with changes in internal pressures, the detection of light leakage into a region of the device normally kept dark, and the detection of oxygen or another gas or substance in a region of the device normally void of it.

Some embodiments of device 500 include a reactive agent which is released into the medication chamber(s) upon tamper event signal 524b and renders the medication harmless. Such an agent could be released automatically by software on device 500 or after receiving a command from HCP 592. In one such embodiment, this agent is released by a mechanical assembly which is activated by software automatically upon a detected tamper event. In another possible embodiment, the agent is released by an impact upon the device, such as the use of excessing force to fracture the device in an attempt to access a multitude of doses.

It should be appreciated that monitored subassembly 522 may include other types of sensors deemed appropriate to monitor the use and condition of device 500 and to provide such information to server 562 or HCP 592 to ensure proper administration of prescribed medication 576. For example, in some embodiments, monitored subassembly 522 includes capacitance sensors to detect leakage or other changes in the normal operating environment of device 500.

Remote monitoring 588 also contains structural and functional components for monitoring patient 594. For example, monitoring biometric data derived from or provided by patient 594 may be considered in connection with treatments involving certain prescribed medications. Specific biometric data may be considered, for example, during the course of treatment with the prescribed medication. Similarly, the condition of patient 594 may need to be considered prior to permitting device 500 to deliver each successive dose of prescribed medication. In many circumstances the condition of patient 594 that is of concern may be obtained by onboard biometric sensors in device 500 and resulting data including biometric data 530b included in remote monitoring 588. Depending on the implementation, HCP 592 may adjust the dose quantity 545 or schedule 547 based on received biometrics 530b. Other embodiments include additional security features requiring the input of patient identity data 543b so that only the intended patient (or patient's approved caregiver) may operate the device. In such embodiments, HCP 592 review of certain collected data may be a prerequisite to enabling regulated subassembly 506 to make a metered dose 512 available for device interface 506. It should be appreciated that in some embodiments, such a determination may be made by monitored subassembly 522, programs executing on server 562 or HCP 592.

In the illustrative embodiment of system 501, the patient parameters that are gathered by monitored subassembly 522 and transmitted to server 562 include patient information such as user identification security data 543b, for example fingerprint scans, and other patient biometrics 530b, for example vital signs, measured by onboard biometric measurement devices (not shown). Note that in some embodiments, user identification data 543b is not collected by a biometric sensor, for example confidential information such as a pin entered into a pin pad on device 500. Monitored patient parameters further include parameters that are not directly obtained from patient 594 by device 501; rather such patient biometric data may be inferred from the noted device parameters. For example, the time at which administration event 526b indicates device 500 was used to deliver administered dose 582, and the quantity of medication included in administered dose 582, may be used to estimate the quantity of medication remaining in patient 594 at some time subsequent to the time of administration. Besides enabling HCP 592 to confirm when prescribed dose 582 has been administered, HCP 592 may determine whether to alter dose schedule 547 should the scheduled time of the next dose be too soon given the estimated or measured blood concentrations of the medication. Such information will also be used to determine the quantity of prescribed medication remaining in device 500 thereby enabling HCP 592 to determine how best to proceed with patient 594.

In some embodiments of system 501, additional features are utilized to monitor patient 594 and collect data, for example user identification data and other biometric data such as vitals collected by components not onboard device 500. For example, some embodiments of system 501 are configured to interface with a smart external device 572a, which can collect biometric data 572b, for example user identifying data or patient vital signs. Biometric data 572b may be transmitted to a component of system 501, for example server 562, indirectly through an API, external database, or patient terminal 568 (described below), while some embodiments of external device 572a communicate directly with the system 501 and server 562 itself. Possible embodiments of a device 572a include a blood pressure monitor, heart rate monitor, a continuous or discrete blood glucose monitor, oximeter, implanted and/or ingestible sensors, as well as a sensor which may aid in user identification or communication such as a camera.

To satisfy the patient's need for easy access to personal treatment data and a method for easily communicating information to their physician, some embodiments of system 501 comprise a patient interface 570, here implemented as a companion application 573 to be accessed via a patient terminal 568, for example patient's smartphone, laptop, desktop, or other computing device. The software of interface 570 may be configured to execute on server 562, locally on terminal 568, or elsewhere. Companion app 573 may include features 586 enabling the input of data and feedback, treatment oversight tools 571, and notifications 569. Such a software 573 may be configured to enable patient 594 to provide objective (measured) or subjective biometric data and other information. The companion application user interface could allow for the manual input of data, such as feedback 523 including side effects, as well as input biometric data 537, and the transmission of this data to the physician via programs executing on server 562. In that way, such programs can consolidate such information with other information related to patient 594 and device 500. Companion application 573 could also make viewable to the patient their personal treatment data, such as real-time updates and reminders, administration log, and calendar. Input biometrics 537 can include measured by external devices which do not themselves interface with system 501. This could include for example the patient's weight, derived from a standard weight scale, where the patient can be trusted to measure themselves and record their weight.

As shown in FIG. 5A, device 500 comprises an electronic communication module 520 configured for transmitting and receiving information via local and global networks, as is well known in the art. Some embodiments of communication module 520 utilize wireless communications; such modes of communication include but are not limited to radio, Wi-Fi, Bluetooth, and LTE. Other embodiments of communication module 520 communicate with the internet via a wired connection. Thus, it should be appreciated that while some embodiments of communication module 520 communicate directly with the internet, for example through Wi-Fi, other embodiments communicate indirectly with the internet, for example via a Bluetooth connection between the device and a smartphone, which is itself wirelessly connected to the internet via a mobile cellular network or wi-fi connection with a local network. Exchanged information may include but is not limited to the sensor data collected by the monitored subassembly 522 and any commands intended for the command subassembly 503 (and hence the regulated subassembly 506).

In one embodiment, patient authorization may be done using near-field communications (NFC). A secure external device used by the patient such as a smartphone, a card, or an implanted device can be used to confirm the patient's identity. In some embodiments, NFC may be utilized to enable the device to communicate with the server through patient terminal 568. In other embodiments, bluetooth communication between the device and patient terminal 568 may be encrypted, or previously verified using a bluetooth pairing code shown by the device using an LED display, sticker or engraving, or otherwise.

It should be appreciated that device 500 may take on a myriad of configurations depending on the risk profile of the prescribed medication, and the prescribed delivery form and method. It is envisioned, therefore, that all or part of device 500 may be handheld, wall mounted, or a desktop or floor-based design.

It should also be appreciated that patient access to the medication as well as patient control 553 of device 500 is limited solely to the administration of the available dose in delivery interface 504, as the patient has no direct control over the quantity of a dose made available, the criteria for availability of individual doses, the schedule at which the doses are available to the patient, nor the identity and associated risk profile of the prescribed medication itself stored in regulated subassembly 506. Advantageously, embodiments of system 501 and device 500 may be used by HCPs to allow patients to self-administer potentially dangerous/abusable medication without direct, real-time supervision, confident that the patient will be unable to administer the prescribed medication other than exactly as it was prescribed.

Figure 5A:
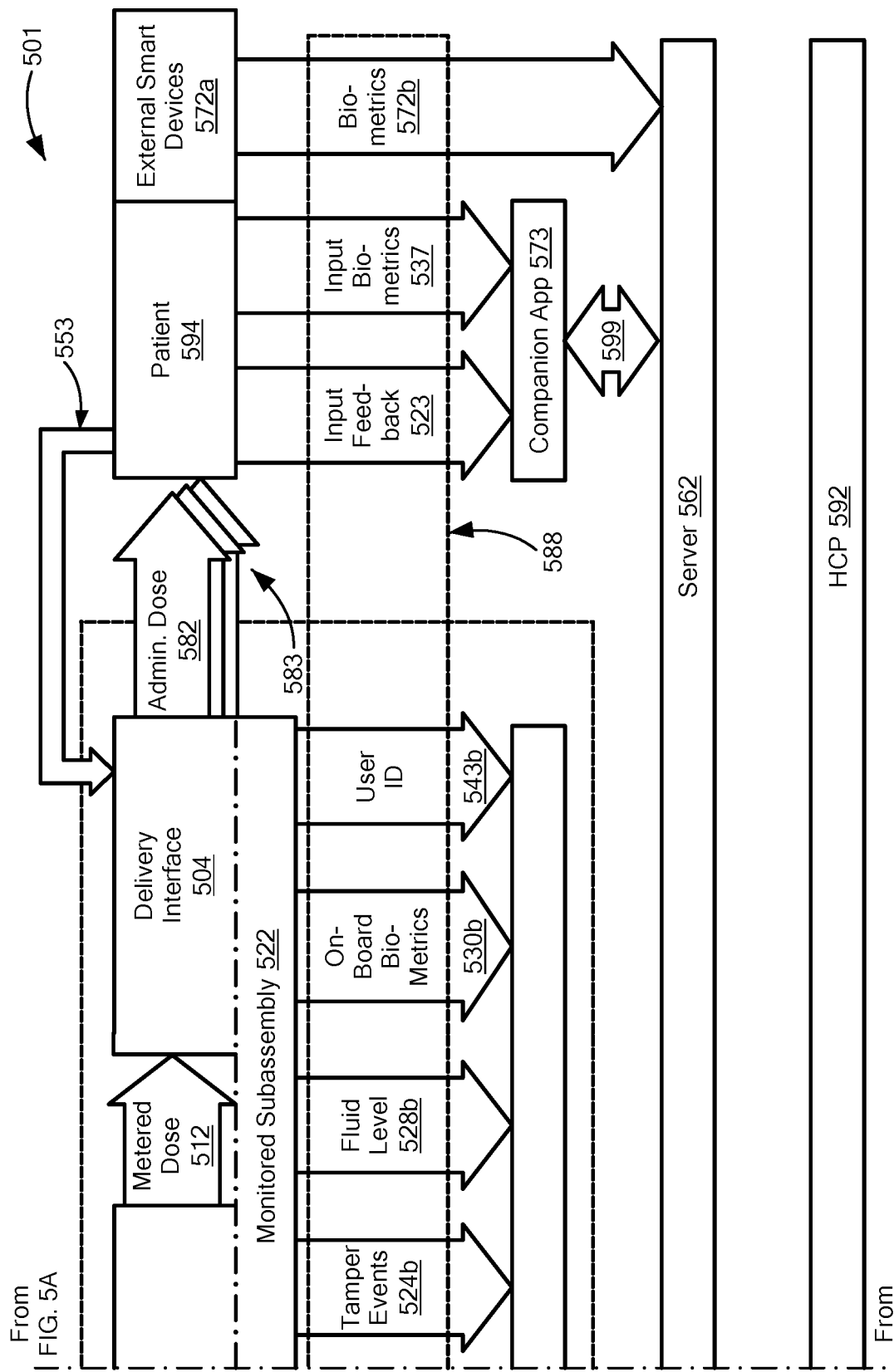
Figure 5B:
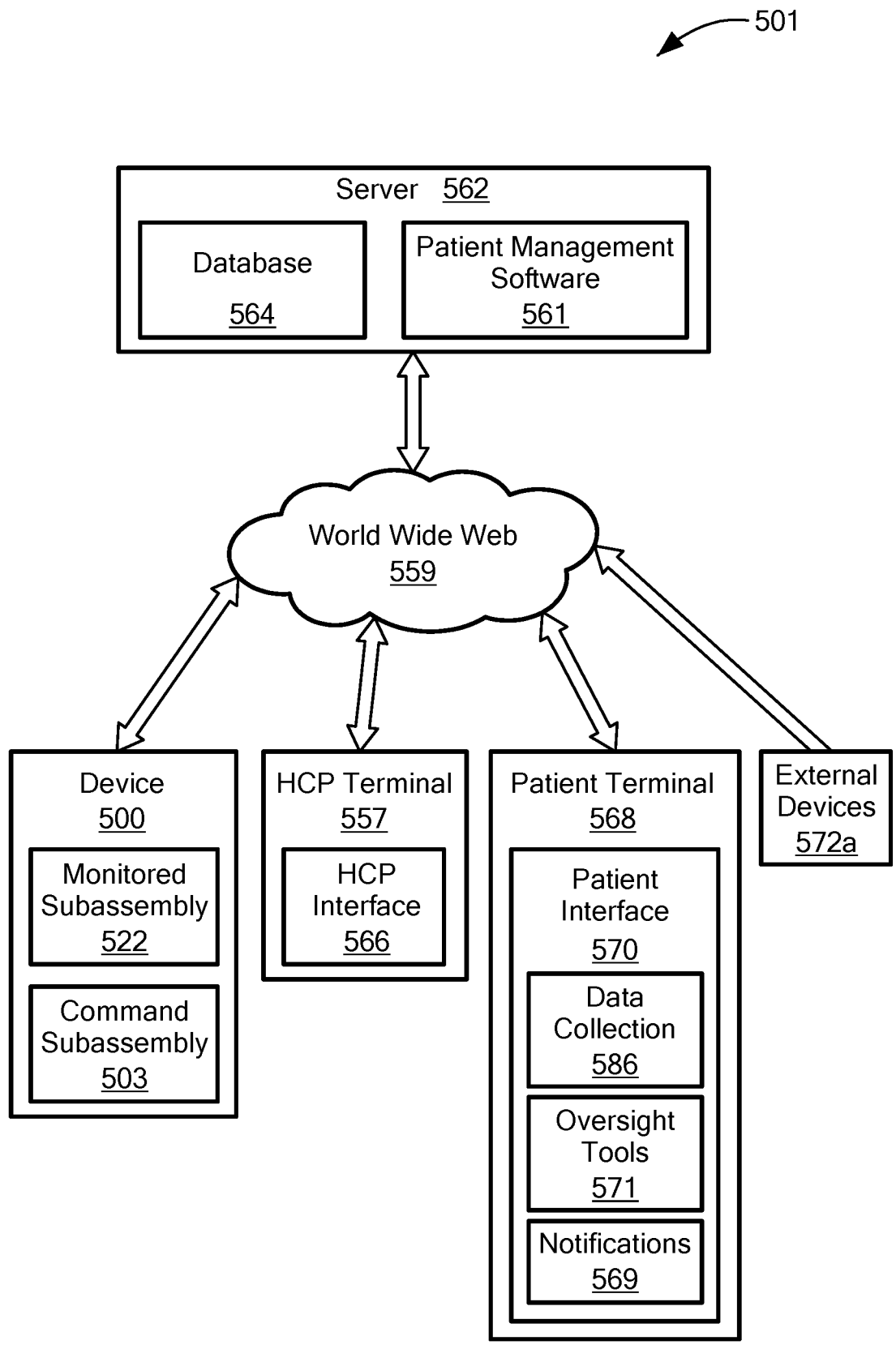
FIG. 5B is a schematic diagram of one embodiment of the information and data flow through a system of the present invention.

The distributed functional components of the present invention are described in greater detail with reference to FIG. 5B. FIG. 5B is a schematic diagram of information and data flow through system 501. In this illustrative arrangement, the communications occur over the World Wide Web 559. It should be appreciated, that although not illustrated, each communicating component may be communicating through a local area network, wide-area network, internet service provider network, and the like, implementing whatever communications technology and protocols required by that network.

The descriptions below address the functionality of certain distributed components and the communication of commands, device and patient parameters, and other data and information between such components. The structural and functional elements of these components which provide them with the capability to communicate remotely over one or more types of networks implementing various network protocols are not described herein as such hardware and software components are well-known in the art.

It should also be appreciated that components of the present invention implement security protocols via dedicated or integrated hardware/software security modules to protect the confidentiality of patient medical records. Such security measures are mandated by international, federal, state and local laws and regulations, as well as health care provider policies. The scope of such security measures encompass, for example, the distribution and storage of patient data, access to patient medical records including device parameters of the specific device 500 utilized by a patient, encryption of communications, validation of individual identities as a condition precedent for granting access to any component in system 501, and so on. In some embodiments of system 501, confidential patient data in the database 564 on server 562 may be anonymized, with identifying information stored locally on the doctor's terminal 557, and/or patient's smartphone 568, for additional security and privacy. It should be understood that the implemented security features change over time as the pertinent laws, regulations and policies change, and as technology and the characteristics of security threats change. Such functionality is not described further herein.

It should be appreciated that aspects of the present invention are anticipated to be implemented in software suitable for executing on general purpose computing platforms operating under the control of any commercially available or proprietary operating system. It should be understood as well that the functional modules described herein as being located on one component or another is for ease of description only and that the functionality described may be distributed across two or more communicating components in system 501.

It should also be appreciated that the functionality described herein may be implemented in software, hardware, or combinations thereof. Thus, the options available in alternative embodiments to allocate the described functionality across hardware and/or software platforms is not described further herein. The described functionality may be implemented as specified or understood to those of ordinary skill in the relevant arts.

As noted above and as shown in FIG. 5A, device 500, remote HCP 592, patient 594, and external smart devices 572a communicate directly with server 562 which is potentially located remotely from each such communicating component. Also noted above and shown in FIG. 5A, monitored device and patient parameters 588 generated by device 500, patient 594 and external smart devices 572a are transmitted over a network to remote server 562 for processing, storage and presentation to HCP 592. Conversely, HCP reviews patient and device parameters, and other patient data or information stored on server 562, and controls device 500 through the creation and transmission of regulatory commands 590 by server 562. For clarity, this architecture is maintained in the following description of FIG. 5B. It should be appreciated, however, that other architectures may be implemented in alternative embodiments.

Referring now to FIG. 5B, a functional block diagram of medication self-administration device 500 is shown. Device 500 includes two functional components relevant to this description: monitored subassembly 522 and command subassembly 503, both of which are described above with reference to FIG. 5A.

Briefly, then, monitored subassembly 522 contains sensors, detectors, etc., the outputs of which are used by subassembly 522 to determine the operational state of regulated subassembly 506 and delivery interface 504, which patient control commands 553 have been applied to delivery interface 504, and to measure the quantity of medication contained at one or more locations in device 500. Monitored subassembly 522 also gathers data from any on-board biometric device(s) 530a and on-board user-identifying devices 543a used by the patient.

Monitored subassembly 522 may also have means for accessing the electronics and memory of any such sensor, detector, etc. to retrieve such device or patient data. Monitored subassembly 522 may process the above data given that the type and format of communications used to transmit such data may be specific to the implemented components in regulated subassembly 506, display interface 504, etc., and may also be specific to the implemented sensors, detectors and the like.

Furthermore, monitored subassembly 522 is configured to interpret such information to determine the values of certain device and/or patient parameters. Such device and patient parameters are transmitted to patient management software 561 executing on server 562 via the internet, as described above. Similarly, command subassembly 503 of device 500 generates signals to control regulated subassembly 506 in response to regulatory commands generated by HCP 592 and transmitted to device 500. The outputs of command assembly 503 may take on any form suitable for the controlled components. For example, command subassembly 503 may generate electronic signals, may shift the voltage on certain input pins of a component, may write data to a microcontroller memory of a component, and so on.

In some embodiments data collected by monitored subassembly 522, such as tamper events and administration sensor events, may be cached or otherwise stored on device 500 or patient terminal 568. This may occur at all times or solely when device 500 is not direct or indirect active communication with World Wide Web 559. In such embodiments, device 500 may relay stored events to server 562 once active communication with World Wide Web 559 is re-established. There may be a period of time that device 500 will function normally and continue to allow patients to self-administer doses without active communication with World Wide Web 559, and after this period, should communication not have been restored, treatment is halted. This may be to ensure patient compliance and device performance. Conversely, patient management software 561 may store data to be sent to device 500 when active communication with World Wide Web 559 is re-established. This may include, but is not limited to, changes in schedule, dose, or data necessary for a dose to be made available, new requirements for biometric data, modifications to schedule 547, and device software updates. Said period may be important for patients who often are in situations without access to World Wide Web 559; for example in wireless embodiments, where a patient may be traveling or lacks access to the internet.

System 501 also includes a patient interface 570 executing on a patient local platform 568. To provide patients with a simple and easy way to access their personal data regarding their use of device 500, as well as to provide information to their physicians, a patient interface 570 is implemented in a terminal, computer, smartphone or other platform 568 local to the patient. In one embodiment, patient interface 570 is implemented in companion application 573 introduced above with reference to FIG. 5A.

A patient data collection function 586 is preferably included in patient interface 570 to provide displays, questions and prompts, data entry fields, file attachment capabilities, and the like to receive subjective data entered by the patient. This includes, for example, patient feedback 523 regarding the medication administered using device 500, side effects, and other medical issues such as relative timing of using device 500 and the administration of other medications, food, etc. Biometric data 537 gathered by the patient is anticipated, and various displays to prompt and receive such data is also provided in embodiments of patient data collection 586. This information is provided to patient management software 561 executing on remote server 562. Patient data collection preferably includes prompts requesting the patient to confirm the successful administration of the prescribed medication as well as any problems administering the medication. In some embodiments, a health survey is displayed automatically after confirmation of successful administration is provided by the patient. In other embodiments, and more generally, patient data collection 586 periodically displays a health checkup form to update the patient's physician with the patient's current medical conditions to enable the physician to optimize treatment. In some embodiments, such a health survey or checkup form may use existing questionnaires, such as a PHQ-9 survey, to collect a specific set of information.

Patient interface program 570 preferably includes a program module 571 that implements oversight tools which facilitate the proper and safe use of device 500. Such tools can include, for example, timers counting down to time of next dose, automatic calculators that determine remaining doses, timing between doses, an emergency call button on each page; a log of future and past administrations; a calendar showing doses as well as calls and appointments with the doctor; a contact page with buttons for contacting the prescribing doctor, the pharmacy, and device customer service. The information utilized and presented by oversight tools 571 is obtained from patient management software 561 on server 562.

Patient Interface 570 preferably also includes patient notifications 569 to to present urgent, important, or otherwise helpful alerts, notices and the like on patient terminal 568. Instructions to display patient notices are transmitted to patient self-management interface 570 by patient management software 561 executing on server 562.

System 501 may include means for utilizing patient-related data generated by external devices 572a, described above with reference to FIG. 5A. If the physician deems it necessary to monitor additional or alternative conditions of patient 594, system 501 may include the ability to access the patient-related data generated by external devices 572a. External devices 572a may include but are not limited to devices that can measure blood pressure, pulse rate, blood oximetry, etc., and/or perform tests such as a breathalyzer test to ensure the patient can safely take the prescribed medication. External devices 572a may also include a global positioning system tracker, camera, etc. It should be appreciated that such patient-related data may be obtained directly from external devices 572a or indirectly from network-accessible system or memory associated with external devices 572a.

For HCP 592 to remotely monitor patient 594 and control device 500, embodiments of system 501 include HCP interface program 566 executing on terminal 557 or executing on server 562 and accessible via a web-based portal by physician 592 via terminal 557. Such access may be available to the doctor, pharmacist, or any other HCP 592 who may need to exercise remote monitoring, remote control, device programming or device filling functions.

Executing on server 562 is a patient management software 561 which accesses patient medical records and device status database 564. Patient management software 561 performs remote monitoring functions performed by patient management software 561 include receiving and processing monitored device parameters and monitored patient parameters transmitted by device 500 over the internet. Such information is stored and formatted for presentation to HCP 592 via HCP interface 566, and for presentation to patient 594 via patient interface 570. Remote regulation functions performed by patient management software 561 include receipt of HCP impetus at HCP interface 566 regarding the control of device 500, and transmitting such device regulatory commands 590 to device 500.

Patient management software 561 receives, processes and collates all patient biometric data 572b received from external devices 572a, input biometric data 537 from patient interface 570, and biometric data 530b from device 500. Patient management software 561 also contains means for drawing inferences regarding a patient's medical condition based on information provided by other external devices that are not biometric devices alone or in combination with the noted biometric data. All this information is stored in patient database 564 for subsequent retrieval and presentation and presented to HCP 592 via HCP interface 566. Patient management software 561 preferably includes means for determining whether the patient biometric data and other medical information, in sum, reveals a condition or situation that warrants timely involvement of HCP 592. This information may include, but is not limited to, logs of device usage, measurements of compliance, measures of health parameters over time, and outcome measures specified by HCP 592 in the form of text, graphs, or a calendar overview.

Patient management software transmits device and patient data to patient interface 570 and HCP interface 566, and receives commands and data provided by the patient and HCP via the same interfaces.

It should be appreciated that patient management software 561 may be integrated with other systems to facilitate communications and data transfer with the patient and HCP. Such systems include email, text services, video conferencing, and the like.

As one of ordinary skill in the art understands, server 562 may be any networked server now or later developed which is communicably coupled to World Wide Web 559. Also, the range of information being exchanged throughout the system 501, all of which passes through the server 562, may include but is not limited to the information depicted in FIG. 5B. This information is processed by patient management software 561 and stored in database 564. Should the patient indicate a need to communicate with HCP or should patient management software 561 determine, based on the information presented alone or in combination with other information in system 501, patient management software 561 generates and transmits a message to HCP 592 indicating that the recent information provided by the patient warrants immediate review. Patient management software 561 can also generate and transmit commands based on analysis of data received, for example a shut-down command 549 upon tamper detection 524b.

There exists a family of embodiments where database 564 is a relational database that stores patient and HCP information in a tabular fashion. Logs can be stored in a separate database table as a set of time-stamped information, including for example critical information such as a tamper event, or more general usage information such as a dose administration history. Diagnostic data, if any, may exist in a separate database table, for example form responses that may be analyzed for consumption by the HCP. Database 564 and associated tables can be encrypted, keeping patient information secure and compliant with international, national, or state laws. In a database table for patient metadata, information stored may include but is not limited to the patient's name and unique identifier, a unique identifier for HCP 592, hashed version of data to confirm user ID 543b, and prescription 574. In some embodiments this is paired to associated tables in which said patients' other data is stored, including but not limited to compliance data, health parameter data, survey data, and notifications 569. In another family of embodiments, database 564 is a non-relational database containing a stream of data. In some embodiments, this data is analyzed periodically, while in others, it is analyzed in real time. In one possible application of real time analysis, the HCP terminal 557 may request PHQ-9 survey results from server 562, where server 562 will query the data from database 564 before returning the analyzed data to HCP terminal 557. In other embodiments, a non-relation and relational database model may be combined. For example, patient and HCP data are stored in a tabular fashion in a relational database, while logs and notifications are stored in a non-relational database as a stream of data.

FIG. 1 is a schematic block diagram of an exemplary embodiment of medication self-administration device 500, referred to herein as medication self-administration device 100. Device 100 is configured to deliver a prescribed medication in the form of an aerated mist into the nasal passage of a patient using the delivery method of a spray nozzle.

Given its intended use, device 100 has an exterior housing 102 configured to be held in one hand by a typical patient 594 and operated by that patient using that same hand. Various embodiments of housing 102 include ergonomic features to facilitate patient control of device 100. It should be appreciated that this is due to the particular delivery site for the medication, and that other embodiments of the device need not be configured similarly. Preferably, exterior housing 102 also has sufficient structural integrity to withstand a range of anticipated forces (type and magnitude) which may be applied to device 100 to gain unauthorized access to a prescribed medication stored therein, as well as to detect leakage, gaseous escape, sudden changes in quantity, and so on.

Delivery interface 104 is, as noted, a manually-controlled spray nozzle. As will be described in detail below, patient 594 operates delivery interface 104 via patient control actions 553 which, in this embodiment, comprises one or more manual depressions of spray nozzle 104 each causing delivery interface 104 to draw medication from a reservoir in device 100 and apply 583 the medication to the nasal cavity of patient 594. Multiple such depressions/applications may be necessary to apply an entire administered dose 582.

Recall that regulated subassembly 506 generally includes those components of device 500 which securely store prescribed medication 576 and precisely provide delivery interface 504 with a metered dose 512 of medication in accordance with remote commands provided by HCP 592. Some aspects of regulated subassembly 506 comprise two distinct yet coupled medication-holding chambers. Such embodiments of regulated subassembly 506 are referred to herein as having a dual chamber configuration.

In the exemplary embodiment illustrated in FIG. 1, device 100 has a dual chamber configuration. Specifically, in this illustrative embodiment, device 100 has two compartments for storing a prescribed medication: a secure, relatively larger, primary chamber 108 fluidically coupled to a relatively smaller, accessible metered chamber 110. Primary chamber 108 is not accessible to delivery interface 106 nor patient 594.

Primary chamber 108 is constructed and arranged to provide a hermetically sealed and tamper-resistant reservoir for storing a prescribed medication. Primary chamber 108 is configured to be refilled by pharmacy 551 via hatch 132, if necessary, and has a volumetric capacity sufficient to hold a predetermined quantity of the medication which may safely be possessed by the patient over an extended period of time while being accessible to the patient only in the limited and controlled manner as described herein.

This predetermined quantity of medication is at least the quantity reflected in full Rx supply 576 of prescribed medication described above with reference to FIG. 5A. Embodiments of hatch 132 include electromagnetic, motorized and/or physical locking mechanism. Such a hatch lock/release mechanism is configured to be controlled remotely by HCP 592, as described above, or hatch 132 may be configured to be controlled directly by, for example, pharmacy 551. In the same or alternative embodiments, primary chamber 108 has a structurally reinforced design that enables the chamber to prevent leakage and withstand attempts of penetration under any reasonable impact or other force.

Metered chamber 110 is configured to store the maximum potential dosage of the prescribed medication for ultimate transfer to delivery interface 104. Metered chamber 110 is configured to be accessible by delivery interface 506 as described herein. As will be described in detail below, in a dual chamber configuration, a specified amount of medication, at the specified time, is transferred from primary chamber 108 to metered chamber 110, allowing the patient to activate the delivery interface to administer the medication in the metered chamber. Fluidic tubing or a needle outlet 148 extends from an opening in the metered chamber or any location where the entirety of fluid volume dispensed into it by the pump is accessible. Embodiments of the metered chamber are configured to prevent access to the medication that is located upstream (not yet transferred, i.e. not intended for current dose) of this chamber.

As noted, primary chamber 108 and metered chamber 110 are fluidically connected to each other. This fluid path 114 consists of suitable tubing. In other embodiments, the two chambers are contained in a single housing and are fluidically coupled via channels in a substrate.

In response to dose quantity command 545 and dose schedule 547, a single dose is transferred from primary chamber 108 to metered chamber 110 via fluidic tubing 114 by a fluid transfer mechanism in form of pump 112. The device makes a precise dose available and nothing more, and the medication transfer mechanism is responsible for transferring this precise dose into a location accessible to the delivery interface 104 and hence the user. In the embodiment of the device in FIG. 1, this mechanism takes the form of a fluidic pump, which, on schedule 547 set by the HCP, pumps precisely one dose from the primary chamber 108 into the metered chamber 110.

Pump 112 is any pump now or later developed that precisely and accurately transfers fluid. The pump type may differ between embodiments, with some possibilities including peristaltic, piezoelectric, syringe, and solenoid pumps. Embodiments of the pump may or may not serve the additional purpose of a one-way valve. In some embodiments, one or more one-way valves may be implemented, as may one or more physical locking mechanisms, to restrict upstream flow and to restrict access to the primary chamber 108.

In the above description of the embodiments illustrated in FIG. 1, chambers 108 and 110 are referred to as having a fixed volumetric capacity. It should be appreciated, however, that in alternative embodiments, either or both chambers are configured to have an adjustable volumetric capacity.

The components of the fluidic subassembly can be spatially configured in any way in order to minimize size and optimize performance. In alternative embodiments one or both of the primary and secondary reservoirs may be adjustable to accommodate a particular medication prescription and desired duration between refills. For example, in one embodiment, the interior surface of one wall of the reservoirs is adjustable by pharmacy 551 or HCP 592 via a volumetric control interface on the device. In certain embodiments, manually adjusting the control interface to one of a few available settings permanently changes the position of the adjustable interior wall. Interlocking features prevent further adjustment. In another embodiment, the reservoirs include a bladder and the volumetric capacity of the bladder is adjusted by the HCP by limiting the expansion of the bladder such as, for example, by filling the interstitial space between the bladder and the interior surface of the reservoirs. In an alternative embodiment, each reservoir is one of a set of reservoirs all having the same form, fit and function but each having a different volumetric capacity.

The embodiment of monitored subassembly 522 of device 100 comprises a tamper sensor 124a and an administration event sensor 126a. Tamper sensor 124a is configured and arranged in device 100 so as to detect unauthorized attempts to access regulated subassembly 106. Implementations of tamper sensor 124a include but are not limited to, capacitive, resistive, or piezoelectric sensors arranged in device 101 to detect applied forces. Other embodiments of tamper sensor 124a detect light or air entering a part of device 100 normally isolated from the outside environment.

Administration event sensor 126a is configured and arranged to detect when patient 594 is using device 100 to self-administer the medication. Embodiments of sensor 126a include but are not limited to, a contact sensor within the spray nozzle delivery interface 104, fluid level sensor within metered chamber 110, or biometric sensor to detect expected biometric changes accompanying a dose. Another embodiment of sensor 126a is a camera structure and arranged to capture images of patient 594 administering the medication or performing some test or act. The electronic subassembly is configured to wirelessly receive commands and to execute such commands, as well as to wirelessly transmit sensor data to the server. The storage, processing, and transmission of data is all designed and executed in accordance with government regulations. A wireless transmitter/receiver receives remote commands (e.g. aliquot dose or unlock refill hatch) and sends them to a microcontroller, which processes them and outputs the necessary signal to the associated subcircuit for execution. Sensor data is recorded by the microcontroller, which then sends it to the wireless transmitter/receiver for transmittance to the paired device/server.

Device 100 is powered through any current or future method, called herein the power source 116. Some possible embodiments of the power source include but are not limited to a disposable battery, a rechargeable battery, a power cord directly to a wall outlet, USB charging port, and wireless charging coil. The entire electronic subassembly is supplied with direct current from a power source 116, which supplies power to each electronic component needing it.

Figure 2:
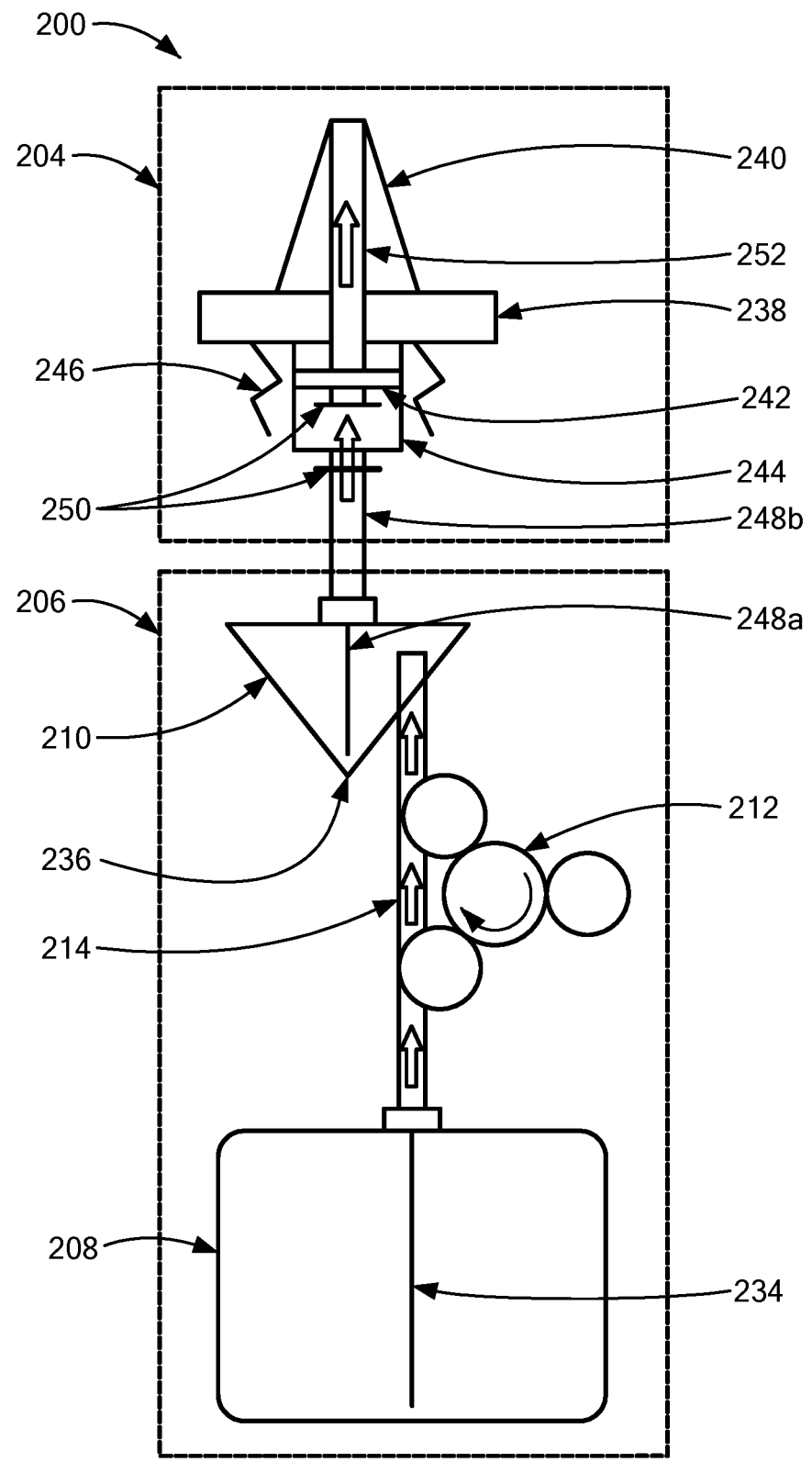
FIG. 2 is a schematic block diagram of one embodiment of a dual-chamber nasal spray delivery device.

FIG. 2 is a schematic block diagram of one embodiment of dual-chamber nasal spray delivery device 100, referred to herein as device 200. Device 200 includes a regulated subassembly 206 fluidically coupled to a delivery interface 204. Regulated subassembly 206 has a dual chamber configuration, comprising primary chamber 208 fluidically coupled to metered chamber 210 via a pump 212.

In the embodiment illustrated in FIG. 2, primary chamber 208 has a secure, hermetically sealed port of connection with a tube 214 which fluidically couples primary chamber 208 and metered chamber 210. Fluidic tubing 214 is coupled to a needle 234 which extends through primary chamber 208, terminating at a location which ensures all of the medication stored in primary chamber 208 is retrievable for transfer to metered chamber 210. In some embodiments, needle 234 is an integrated component of primary chamber 208 while in other embodiments it is a unitary feature of primary chamber 208. In some embodiments, the interior surface of primary chamber 208 opposite the port side of the chamber is configured to facilitate uptake of the medication by needle 234.

Pump 212 is constructed and arranged to transfer medication from primary chamber 208 to metered chamber 210, and in this embodiment is a peristaltic pump 212, through which tubing 214 passes. Peristaltic pump 212 is a form of positive displacement pump, and works by utilizing a carousel of cylinders, at least one of which is always in contact with and pressing flat tubing 214, restricting flow at that pinch point. When pumping, this carousel rotates about its central axis, driven by an electric motor, and the cylinders rotate around this central axis with it, as well as on their own individual rotational axes to reduce friction with tubing 214. The pinched point on tubing 214 is hence moved forward along the tube, pushing with it the fluid above the pinch point, and creating a suction which draws up more fluid. By the time the uppermost pinch point is released, the next cylinder has already pinched a lower point in the tube. This rotational motion of the carousel therefore transfers a quantized volume of fluid with each revolution.

The medication advanced by pump 212 continues through tubing 214 into metered chamber 210. As noted, the medication stored in metered chamber 210 is accessible to delivery interface 204. An extraction needle 248*a* extends from an outlet port at the top of metered chamber 210 to the opposing, bottom surface of the chamber, for example the metered chamber's nadir 236. In this embodiment, the bottom interior surface is concave, facilitating the accumulation of medication in metered chamber 210. has a concave interior surface When device 200 is held in its application/delivery orientation, the medication will accumulate at the nadir 236 of the concave surface. In such embodiments, the fluidic tubing or needle 248*a* extends through metered chamber 210, terminating immediately above nadir 236.

In other embodiments, the interior surface(s) of either chamber and/or tubing (208, 210, 214, 234, 248*a*, 248*b*) include channels, coatings, etc. optimized for the viscosity and other properties of the medication to facilitate the fluidic transport of the medication through device 200. The fluidic tubing provides a hermetically sealed, tamper-proof and sterile passage between primary chamber 208 and a fluidic pump.

As noted above with reference to FIG. 1, medication delivery interface 104 is a manually-controlled spray nozzle configured to draw medication from a reservoir in device 101. Patient 594 operates delivery interface 104 via patient control actions 553 which, in this embodiment, comprises the manual depression of spray nozzle 104 causing an application 583 of medication to the nasal cavity of patient 594. Multiple such depressions may be necessary to apply an entire administered dose 582.

This illustrative embodiment of spray nozzle 204 includes a spray chamber 244 having a capacity to retain a volume of prescribed medication ideal for uptake by the nasal mucosa in a single application or administration 583 of the medication.

A rounded nasal cone 240 with a capillary 252 from the center of its base through its tip serves as the nozzle, and is designed to fit well in a common nostril and spray a medication particle array of optimal geometry. Spray capillary 252 extends through a reverse plunger piston 242, terminating in spray chamber 244. As such, there is a contiguous fluid path from spray chamber 244 through nasal cone 240 to exit the distal end of the nasal cone.

Spray chamber 244 is fluidically connected to metered chamber 210 via tubing 248*b*. Tubing 248*b* is configured to be securely attached to an access port of metered chamber 210 and metered chamber extractor tubing or needle 248*a*. Spray nozzle 204 includes a one-way valve 250 in extractor tubing 248*b* to prevent upstream, or reverse, flow of medication retained in spray chamber 244.

Device 204 is to be controllably grasped in one hand of patient 594, with the index and middle fingers resting on the flanges of nozzle depressor 238, causing nasal cone 240 to extend through the fingers. Patient control actions 533 include patient 594 depressing nozzle depressor 238, causing it to travel toward the body of device 200.

Embodiments of spray nozzle 204 include a manually-controllable reverse plunger piston 242 configured to drive the medication retained in spray chamber 244 through a spray capillary 252 as piston 242 advances through chamber 244 in response to patient 594 depressing nozzle depressor 238. medication traveling through spray capillary 252 exits the distal end of nasal cone 240 in a mist.

A spring 246 located in spray nozzle 204 applies a bias force to nozzle depressor 238. When patient 594 activates spray nozzle 204, the manual force applied to nozzle depressor 238 is sufficient to overcome the spring bias force so as to move nozzle depressor 238 toward device housing 102.

Subsequent physical release of depressor 238 enables plunger piston 242 to return to its original, retracted position due to the biasing force of spring 246. As plunger piston 242 returns to its retracted position, it creates a vacuum in spray chamber 244 sufficient to draw additional medication, if any, from metered chamber 210. A second one-way valve 250 configured and arranged to prevent air from entering metered chamber 210 via spray nozzle 204.

It should be appreciated that in some embodiments nasal cone 240 and reverse plunger piston 242 are a single, unitary unit. In other embodiments nasal cone 240 is detachable from piston 242 and is one of a set of nasal cones of various sizes and shapes, each configured to optimally fit in a predetermined class of patient nasal cavities.

System 501 may further comprise a confirmation subsystem in some embodiments which confirm certain steps of the medication delivery process to ensure a precise amount was properly self-administered by the patient. This may be done through any number of methods, but three primary approaches comprise confirmation of the amount of medication made available to the patient, confirmation of the amount of medication which exits the device during administration, and the amount of medication which is properly received by the patient's body. Any number of these approaches could be incorporated into a confirmation subsystem. Note that some embodiments of the confirmation subsystem may be fully or in part a component of monitored subassembly 522. Descriptions of specific embodiments of system 501 which comprise a confirmation subsystem are as follows.

The first approach to a confirmation subsystem, one which confirms the amount of medication made available to the patient to self-administer, could use any number of methods to achieve this task. Some embodiments of device 200 for example comprise a fluid level sensor to determine the volume of fluid that is in metered chamber 210 during and/or after a dose is transferred into it, while other embodiments comprise a fluid level sensor to determine the volume of fluid that is in the primary chamber 208, the decrease in which indicates the amount of medication made available to the patient. In some embodiments, a flow sensor is used to determine the volume of fluid that has been transferred from primary chamber 208 to metered chamber 210, actively measuring the medication being made available to the patient as it is being made available. In some embodiments of system 501, the confirmation subsystem and the data it provides with its sensors and algorithms can be utilized to improve regulation itself. For example, there is an embodiment of device 200 comprising a flow sensor incorporated into the fluidic tubing 214 between the peristaltic pump 212 and metered chamber 210. When the pump is activated in order to make a dose available, it remains active only until the flow sensor detects that exactly a full single dose has been transferred to metered chamber 210, at which point pump 212 becomes inactive.

The second approach to a confirmation subsystem, one which confirms the amount of medication which exits the device when a dose is administered, could use any number of methods to achieve this task. Some embodiments of such a confirmation subsystem includes one or more fluid level or volume sensors positioned in or proximate to metered chamber 210 controlled by the confirmation subsystem to detect the amount of medication in metered chamber 210 before and after a dose is administered. The confirmation subsystem determines the amount of medication that exited device 200 by calculating the difference between these two values. In other embodiments, this is achieved by directly measuring the amount of fluid that exits or flows out of metered chamber 210. For example, in some embodiments, a flow sensor is incorporated in or adjacent to nozzle 204, for example between metered chamber 210 and spray chamber 244 or between spray chamber 244 and the distal tip of nasal cone 240. The confirmation subsystem controls this flow sensor to detect fluid exiting nozzle 204 and thus device 200. Depending on the type and location of such a flow sensor, the confirmation subsystem utilizes the outputs of such a flow sensor to calculate the quantity of medication administered to the patient. In a further embodiment, the confirmation subsystem comprises an internal scale which detects the total mass of the device or any combination of components therein, and any decrease in which can be assumed to be due to medication exiting the device.

The third approach to a confirmation subsystem, one which confirms that the correct amount of medication is properly received by the patient's body, could use any number of methods to achieve this task. In some such embodiments, an external device, such as a blood monitoring system, may be cross-referenced to determine concentration of medication in the bloodstream. Such a sensor may also be onboard device 500 in some embodiments. In some embodiments, a proximity sensor is used to calculate the distance between device 500 and the patient, and using that information to estimate medication uptake. This information may be used to improve the accuracy and precision of the dose dispensed, for example by automatically adjusting the pump time (within a preset safe range) to compensate for poor uptake trends, or by giving an informal recommendation to the HCP regarding dose concentration or schedule.

If it is determined by the confirmation subassembly, through one or multiple of these approaches and methods, that a patient has not properly taken their dose, system 501 may take reactionary measures. For example, by measuring the amount of medication available and/or the amount of medication which exited the device, it may on occasion be determined that a portion of the dose remained in the device after administration. This may lead, for example, to the patient receiving a notification on their companion application notifying them of the error and instructing them to reattempt administration. In some embodiments, should this occur, and perhaps after the patient fails to take corrective action, the device makes less medication available upon the subsequent dose. In other embodiments, the device will retract the availability of the leftover medication. For example, in device 200, peristaltic pump 212 may reverse and pump leftover fluid from the previous dose from metered chamber 210 back into primary chamber 208. HCP 592 may be made notified, and the HCP or patient management software may modify dose amount 545 or schedule 547 or may shut down the device. Analysis 961 may draw data regarding leftover doses in analyzing patient compliance. In other embodiments, system 501, patient management software 561, or HCP 592 may become aware of poor dose uptake from a patient and take corrective action. For example, more doses may be made available or the volume of future doses may be increased. For the purpose of illustration, if external devices 572 determines that only half the dose has entered the patient's bloodstream, an additional dose may be requisitioned by HCP 592.

Figure 3:
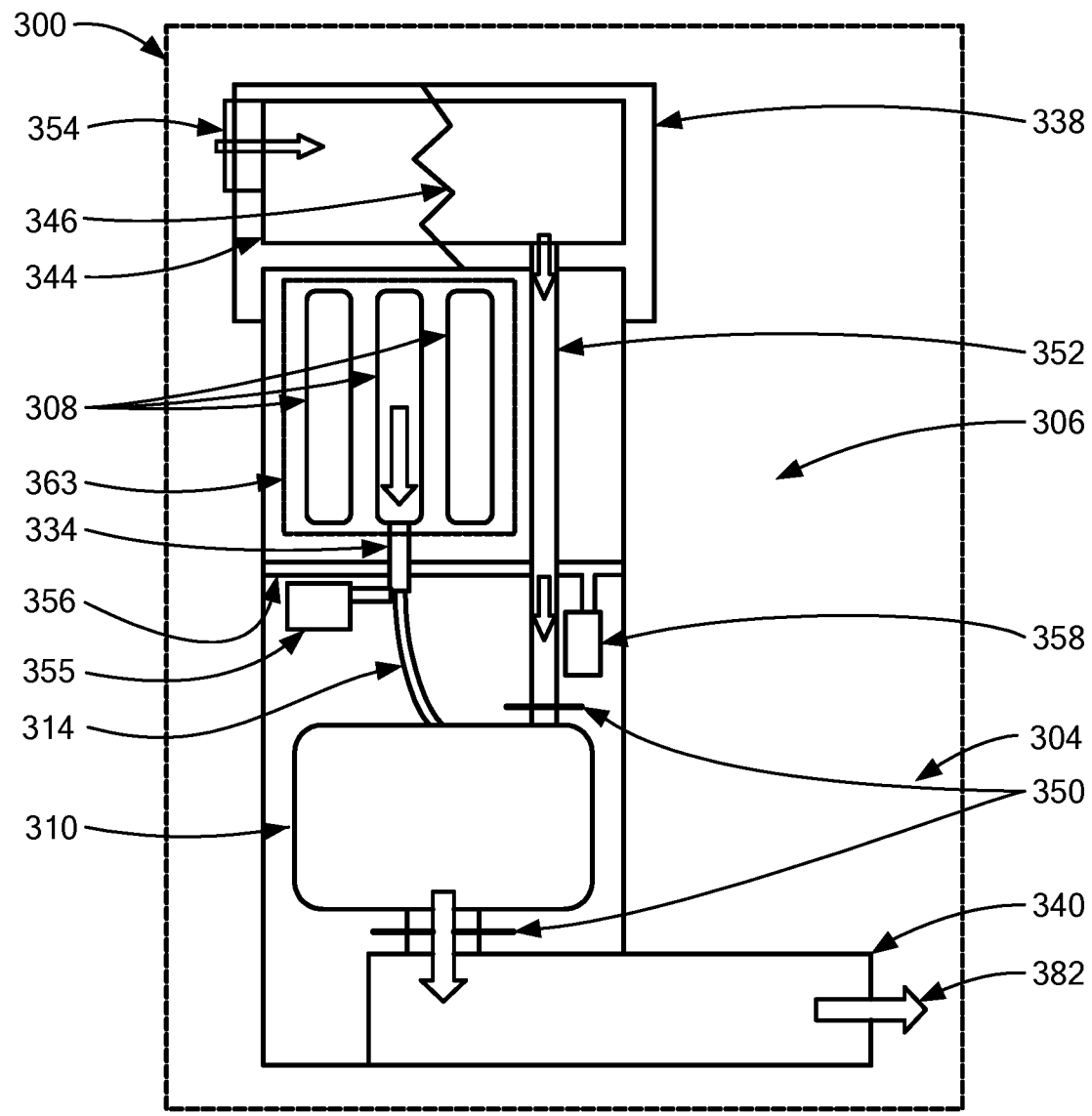
FIG. 3 is a schematic block diagram of an alternative embodiment of a medication self-administration device.

FIG. 3 is a schematic block diagram of an alternative embodiment of medication delivery device 500, referred to herein as medication delivery device 300. Device 300 is configured to provide an administered dose 382 of prescribed medication in the form of a gas using the delivery method of an inhaler for the purpose of making the gaseous medication available for inhalation by a patient. Device 300 includes an alternative embodiment of regulated subassembly 506, referred to herein as regulated subassembly 306.

Regulated subassembly 306 has a set of independent compartments, referred to herein as cartridges 308, each configured to store at least a single dose of prescribed medication. In the embodiment shown in FIG. 3, regulated subassembly 306 has three such cartridges 308. It should be appreciated, however, that any number of cartridges 308 may be implemented in alternative cartridge configurations. As will be appreciated from the description below, collectively, cartridges 308 are functionally analogous to the primary chamber in the dual chamber configurations described above. Similarly, a currently-accessed cartridge 308 is functionally analogous to the metered chamber in the dual chamber configurations described above.

Device 300 includes an alternative embodiment of delivery interface 504, referred to herein as delivery interface 304. Regulated subassembly 306 is fluidically coupled to delivery interface 304 as described hereinbelow. Delivery interface 304 contains a holding chamber 310 fluidically coupled to a selected cartridge 308 via a fluid transfer mechanism of regulated subassembly 306. Holding chamber 310 is configured to store a single gaseous dose of a prescribed medication, and to provide that medication to the patient as described below.

Said fluid transfer mechanism includes an extraction tap 334 configured to penetrate a selected cartridge 308 to initiate a fluid path between the selected cartridge and holding chamber 310. Cartridges 308 may be configured with a penetrable port while extraction tap 334 is configured to penetrate the implemented type of port. For example, in one embodiment, cartridges 308 have a silicone seal while extraction tap 334 comprises a syringe. Cartridges 308 are pressurized; that is, cartridges 308 retain prescribed medication under pressure which evacuates the cartridge when penetrated by extraction tap 334.

The fluid transfer mechanism includes a series of integrated tracks 356 over which extraction tap 334 travels. Integrated tracks 356 are proximate the array 363 of cartridges 308. Under the control of one or more motors 358, extraction tap 334 travels over tracks 356 to be positioned immediately adjacent a selected cartridge 308. Once tap 334 is aligned with selected cartridge 308, an actuator 355 advances tap 334 toward selected cartridge 308 until tap contacts selected cartridge 308. Upon contact, extraction tap 334 penetrates the selected cartridge.

Extraction tap 334 is fluidically coupled to a tube 314 the opposing end of which terminates in holding chamber 310. Thus, extraction tap 334 and tubing 314 provide a continuous fluid path into holding chamber 310.

As noted, cartridges 308 are pressurized. As such, when tap 334 penetrates selected cartridge 308, the medication contained therein is evacuated under the cartridge pressure, causing the medication to flow into holding chamber 310.

It should be appreciated that in alternative embodiments, fluid transfer mechanism 312 retains extraction tap 334 in a fixed position, and array 363 of cartridges 308 rotates or translates relative to extraction tap 334 to align a selected cartridge adjacent to the tap.

It should also be appreciated that in alternative embodiments, extraction tap 334 translates relative to cartridges 308, and penetrates a selected cartridge 308, in response to patient control actions rather than in response to electromechanical motors 358 and actuators 355.

Delivery interface 304 of device 300 comprises a collapsible air chamber 344 fluidically coupled to holding chamber 310 via air exit duct 352. Collapsible air chamber 344 is constructed and arranged to be manually collapsed in response to a manual force applied to a depressor cap 338.

As air chamber 344 is being collapsed, air occupying the chamber is forced through air exit duct 352 into holding chamber 310, replacing and forcing the medication contained therein out of the chamber and through a mouthpiece 340 to exit the device as an administered dose 382 of the prescribed medication.

When depressor cap 338 is released, the bias force of spring 346 drives the cap back up to its original position. As depressor cap 338 returns to its default position, it causes collapsible air chamber 344 to expand, creating a vacuum that draws air into the chamber through one-way air intake duct and filter 354.

In an alternative embodiment, fluid transfer mechanism 312 provides a direct path from an extraction tap 334 to mouthpiece 340 or other delivery interface component suitable for the specified delivery method. In still other embodiments, cartridges 308 are not pressurized and the prescribed medication contained in a selected cartridge is drawn from the cartridge by delivery interface 304.

Advantageously, embodiments of medication delivery device 300 securely stores the prescribed medication unselected cartridges of cartridge array 363, which are inaccessible by the patient and the delivery mechanism. The patient only has access to the precise dose of prescribed medication stored in a selected cartridge 308, which is made accessible in accordance with the dose schedule command provided by HCP.

Figure 4:
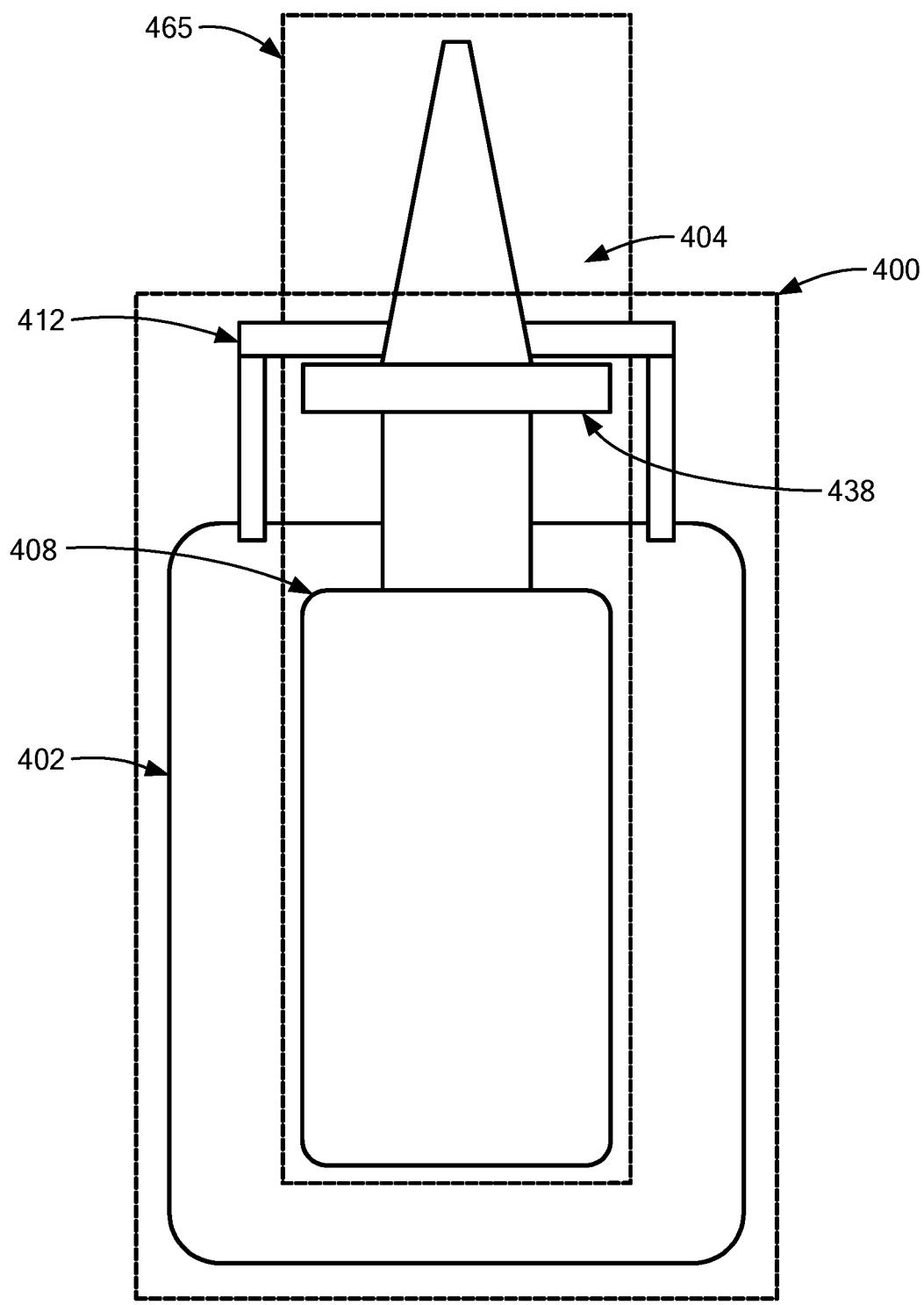
FIG. 4 is a schematic block diagram of an alternative embodiment of a medication self-administration device.

FIG. 4 is a schematic diagram of an alternative embodiment of the device of the present invention, referred to herein as having an add-on device configuration. Such an add-on device may be used in conjunction with an existing third-party medication delivery device 465 rather than as a replacement for such device. The functionality of the two devices in tandem would be equivalent to those functions described for device 500. One example of such an embodiment is a device 400 which attaches and locks onto an existing nasal spray product, and adds to it the regulating and monitoring functions of device 500. While the third-party device 465 would be storing and delivering the medication, the add-on device 400 could allow depression of the spray nozzle only a specified number of times, at specified times and dates, while also tracking administration, tampering, and more. This add-on device would be internet-connected, and have all the same functionality as device 500 beside the storage and delivery of medication.

Device 400 is one embodiment of such an add-on device, paired with 3rd-party standard nasal spray 465. The standard nasal spray 465 consists of a single chamber of medication 408 which is directly accessible to spray nozzle assembly 404. Device 400 is securely attached to device 465. Device 400 has a tamper-resistant outer shell 402 which fully surrounds chamber 408 and has built-in sensors to detect any attempt to separate the two devices. Device 400 regulates the use of device 465, including both dose quantity 545 and schedule 547, with a component 412 which encapsulates the spray nozzle depressor 438 of device 465. The ability for the user to depress the depressor and hence administer medication is determined by the state of component 412, which, utilizing an electromagnetic mechanical locking mechanism, can unlock to allow for administration, and lock to restrict administration. Device 400 further consists of a monitored subassembly and necessary electronics, including a communication module, in order for the paired devices to together have the same functionality as device 500.

The displays generated by one embodiment of patient interface 570 are illustrated in FIGS. 6A-6H. As noted, interface 570 may be implemented as a downloadable application to execute on a patient's smartphone. Such a downloadable application was introduced above as companion app 573 in connection with FIGS. 5A and 5B.

Figure 6A:
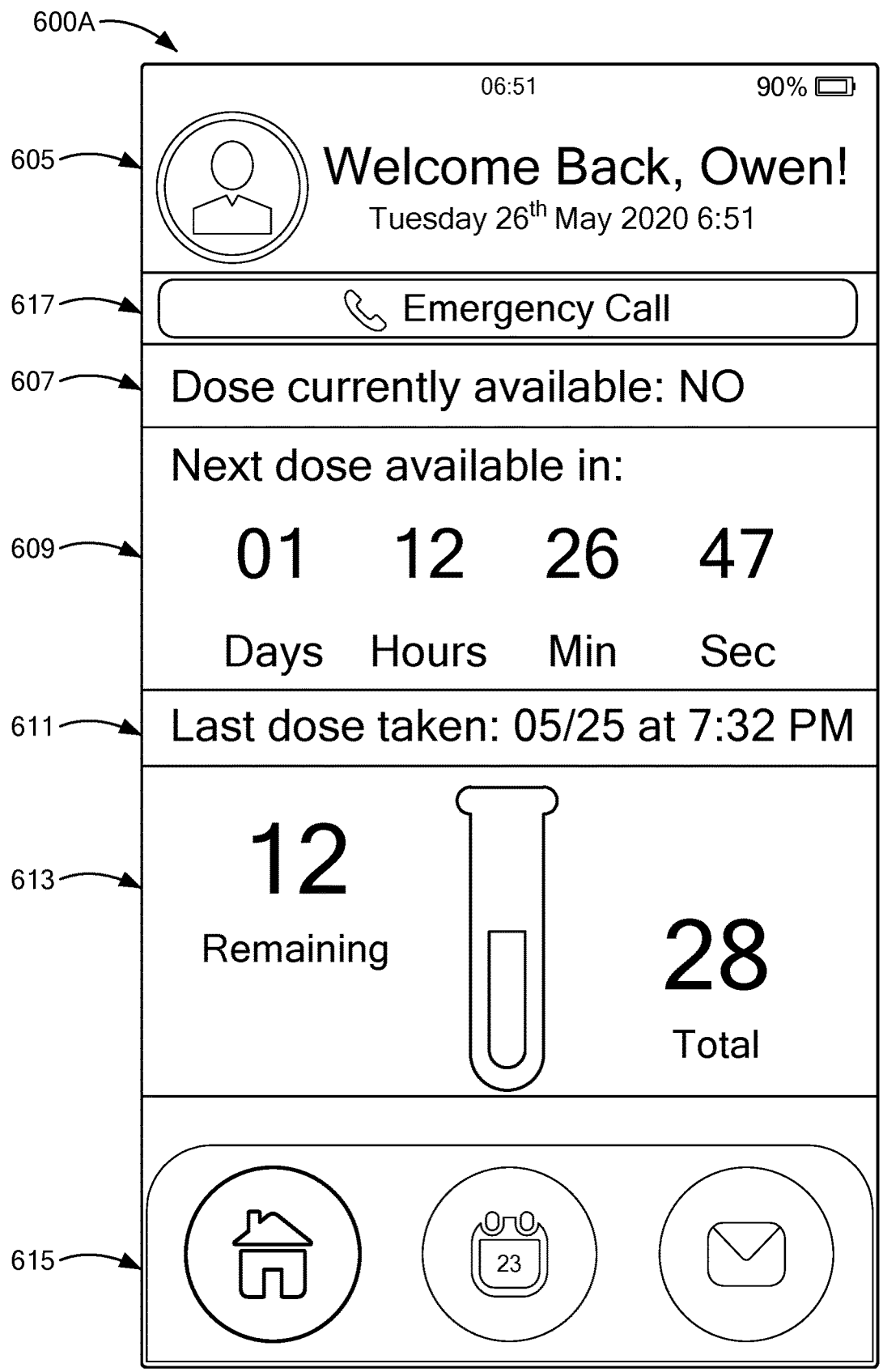
FIGS. 6A-6H are displays generated by embodiments of a patient interface of the present invention.

A home page 600A is presented in FIG. 6A. Home page 600A has a header 605 including user profile information and current time and date, as well as an emergency call button 617 which dials emergency services after the patient confirms the initial selection of the call button was intentional. Below the header is an indication 607 of whether a dose is currently available or not. Below 607 is an actively ticking countdown 609 to the next scheduled dose. Below that is indication 611 of the time and date of the last dose taken, and below that is an indication 613 of how many doses are remaining in the current prescription. At the bottom of the page is a navigation menu 615, with large buttons to navigate between the home page 600A, calendar/log page 600B/C and contact page 600D.

Figure 6B:
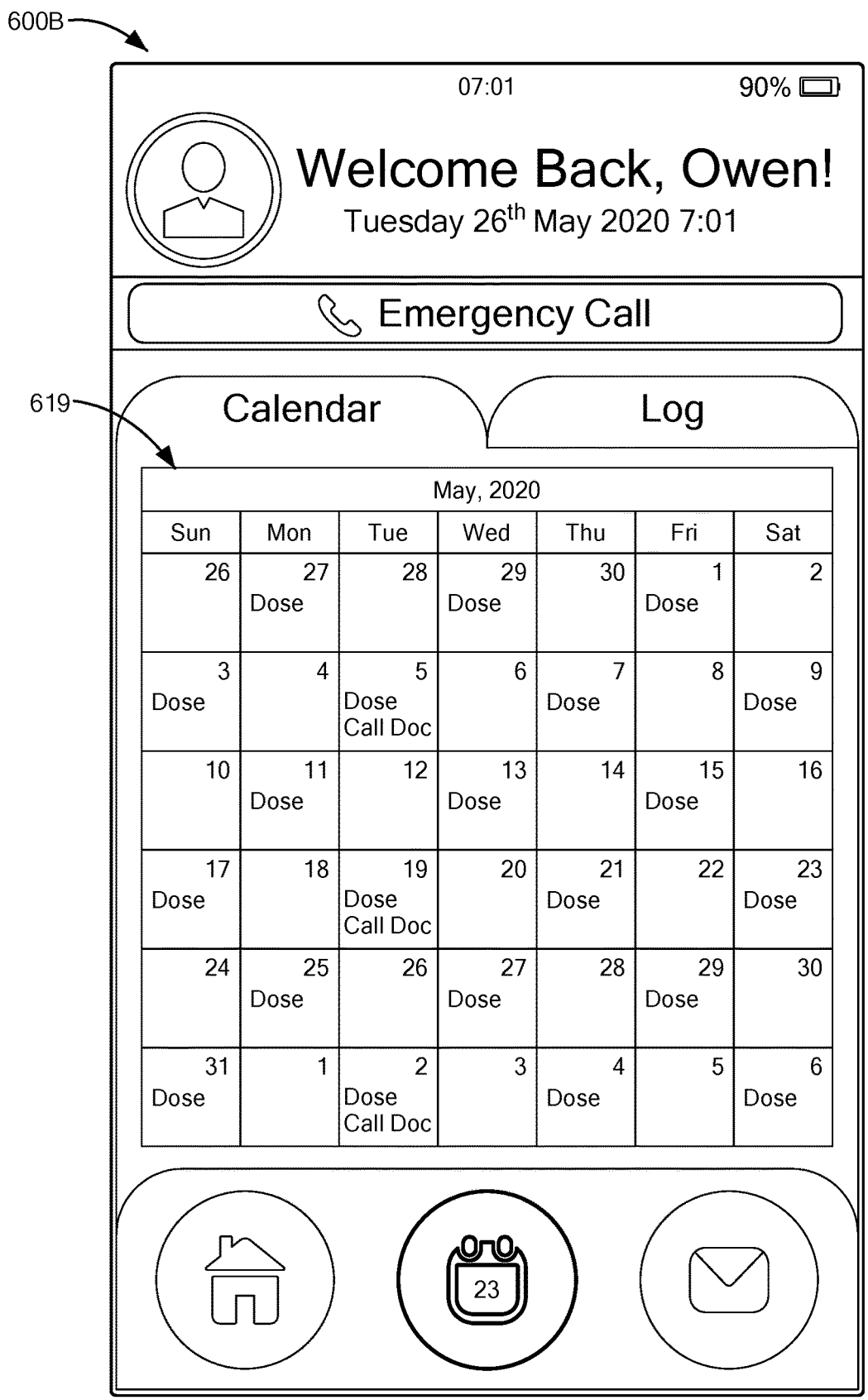

A displayed scheduling page 600B is presented in FIG. 6B. Page 600B includes a calendar 619 in addition to the same header 605, emergency call button 617, and menu 615. Calendar 619 includes doses, scheduled check-up calls with the doctor, as well as doctor's appointments.

Figure 6C:
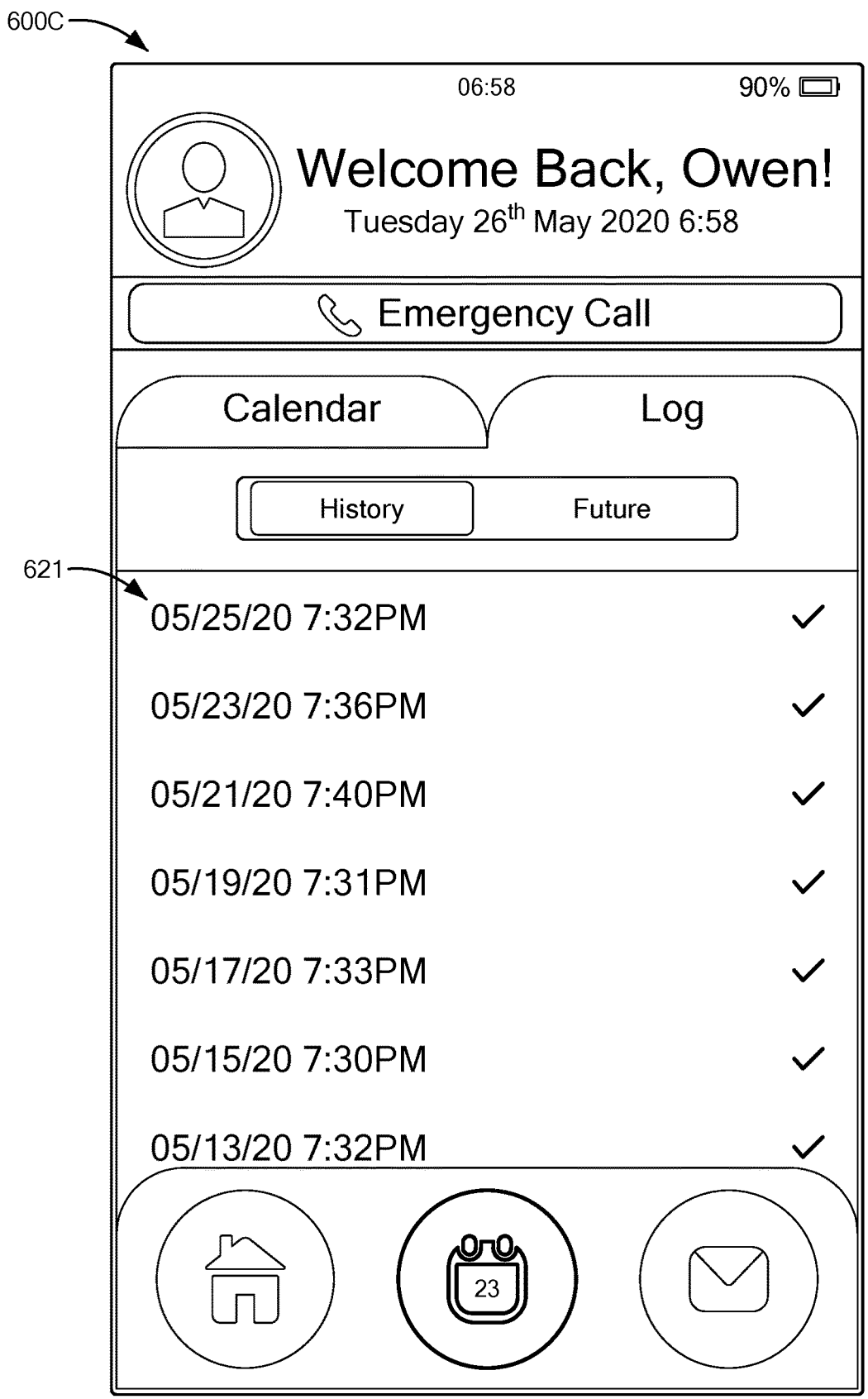

A displayed log page 600C is presented in FIG. 6C. Log page 600C includes a listing or log 621 of prior and future doses. Log 621 and calendar 619 are both within the same navigation page, which can be toggled between them.

Figure 6D:
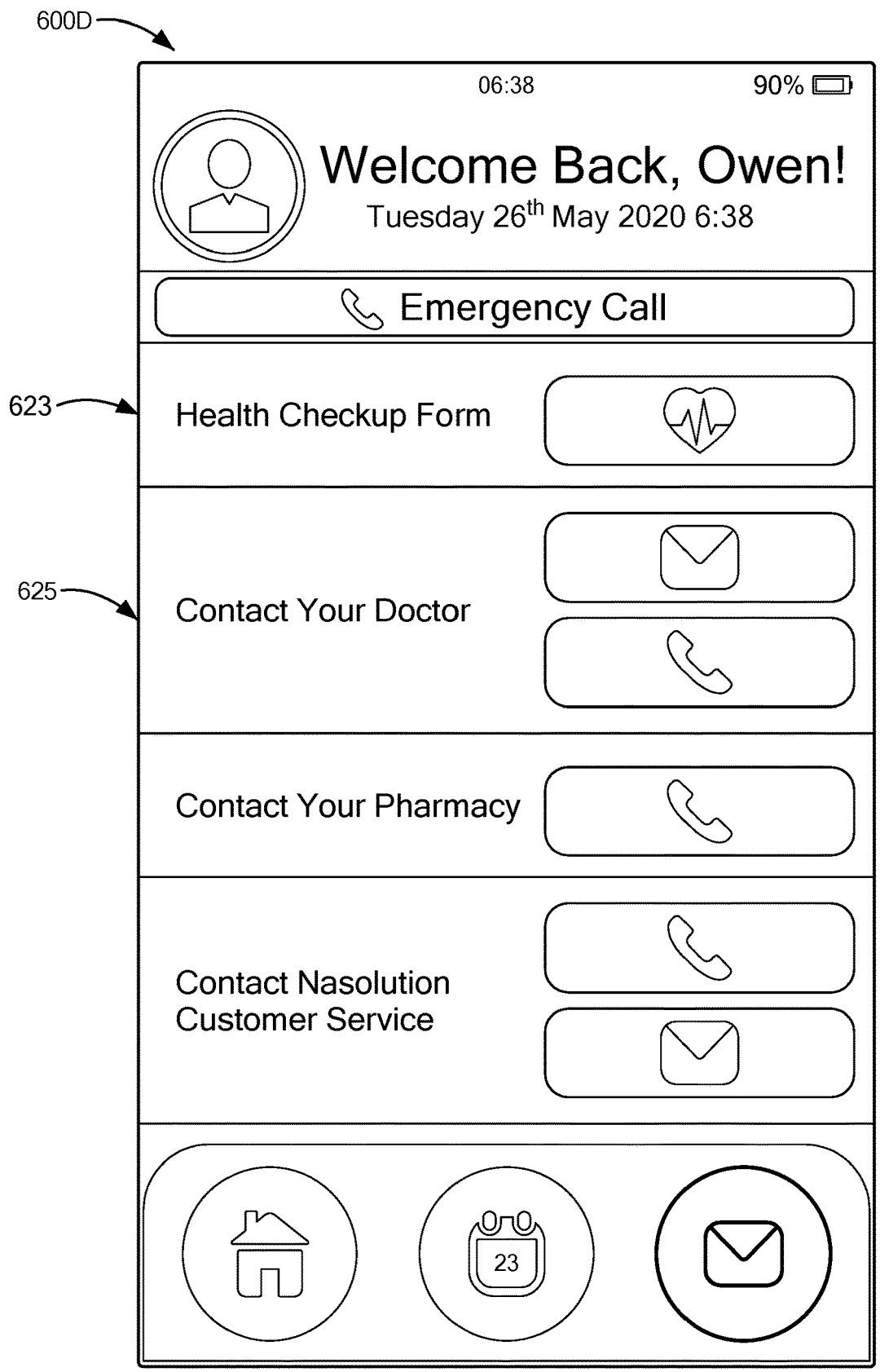

A displayed contact page 600D is presented in FIG. 6D. Contact page 600D includes the same header 605, emergency call button 617, and menu 615. In addition, a button is displayed which, when selected, brings the patient to a health checkup form 623. Form 623 has data entry fields and option selection features for the patient to input health-related data into patient interface 570, including the input of feedback 523 and biometric 537. This information is transmitted to patient management software 561 executing on server 562 for processing and storage, and for presentation to HCP 592 when appropriate.

Returning to display page 600D in FIG. 6D, below the health checkup form button is a series of contact links 625, including buttons to email and call the user's prescribing doctor, call the pharmacy from which the medication was obtained, as well as call and email the customer service for help with the device or other system component.

Figure 6E:
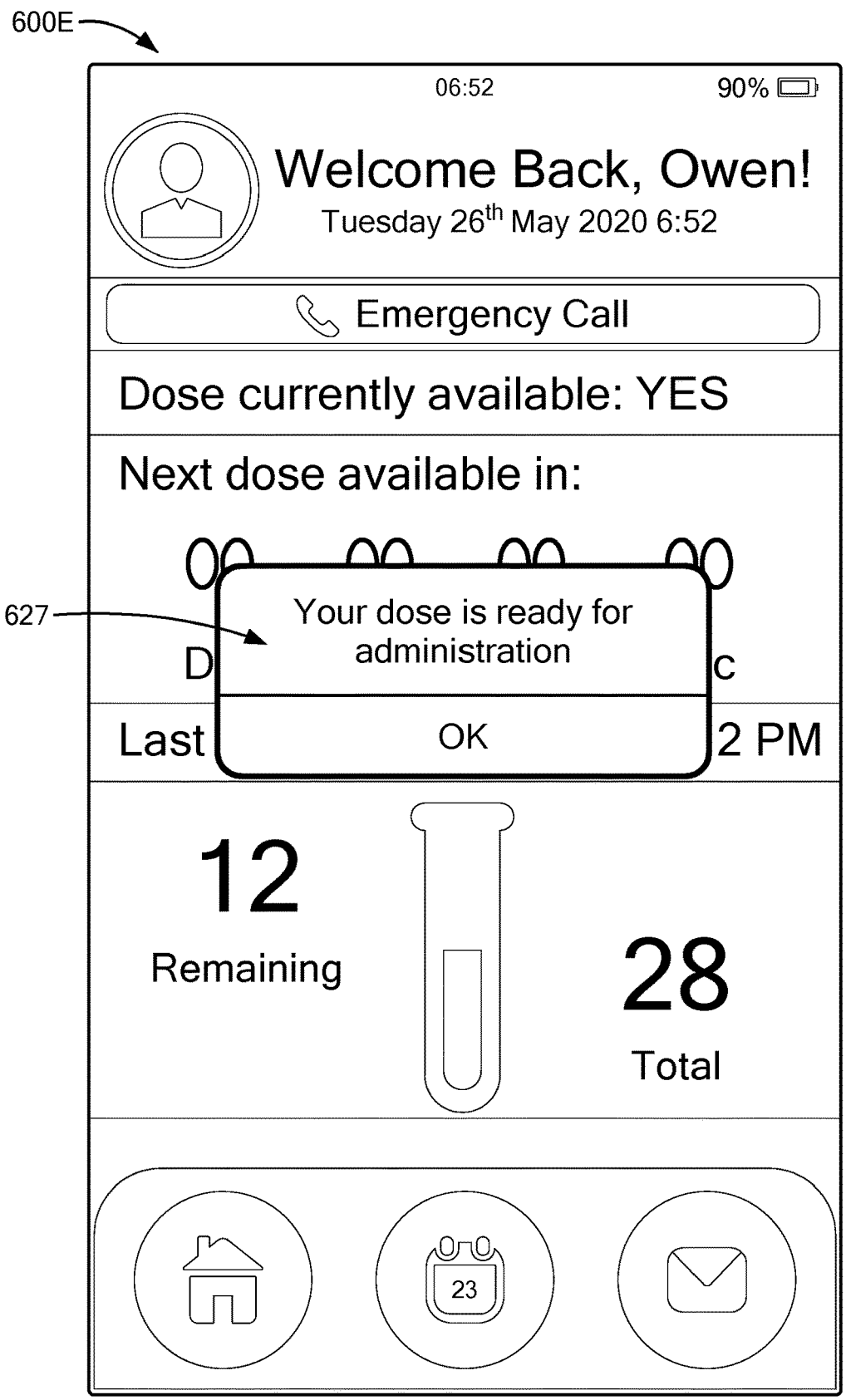

A displayed notification page 600E is presented in FIG. 6E. Page 600E includes a popup dialogue 627 indicating that a dose is ready to be administered. This popup would appear after the scheduled dose time arrives, all requirements are met, and the device makes the dose available. This popup would also be accompanied by a push notification.

Figure 6F:
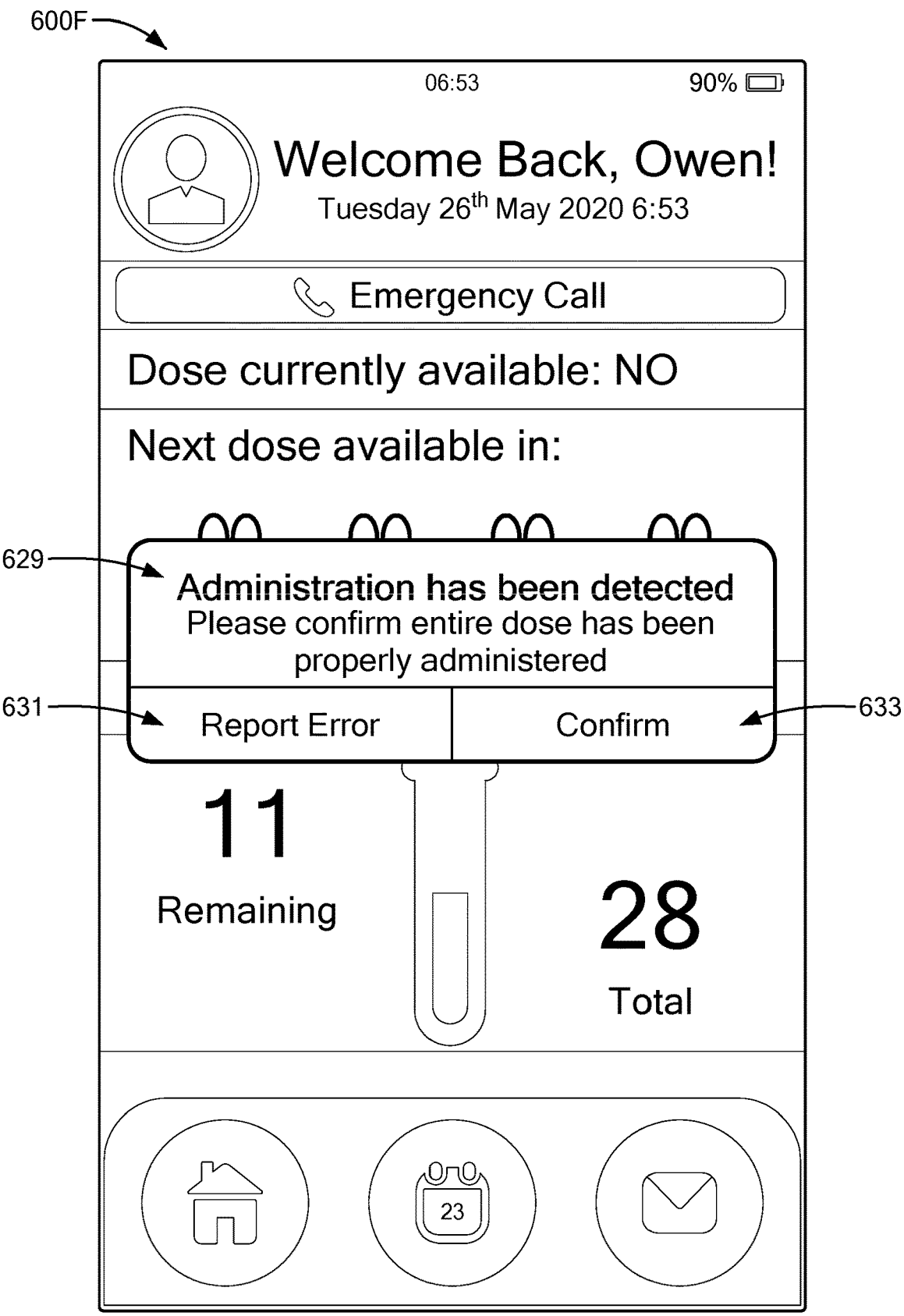

An inquiry display page 600F is presented in FIG. 6F. Page 600F depicts the popup dialogue 629 indicating that the administration of the scheduled and available dose has been detected by the device's onboard administration sensor(s). This popup requests for the user to either confirm that the dose was successfully administered 633 or report an error 631. When 631 is selected, another popup dialogue inquires about the error type and helps to hopefully resolve the problem. By selecting 633, the system is updated to reflect the successful administration, and another popup window appears asking for feedback on health and side effects experienced as well as the treatment as a whole. Such a popup may be similar or identical to health checkup form 623.

Figure 6G:
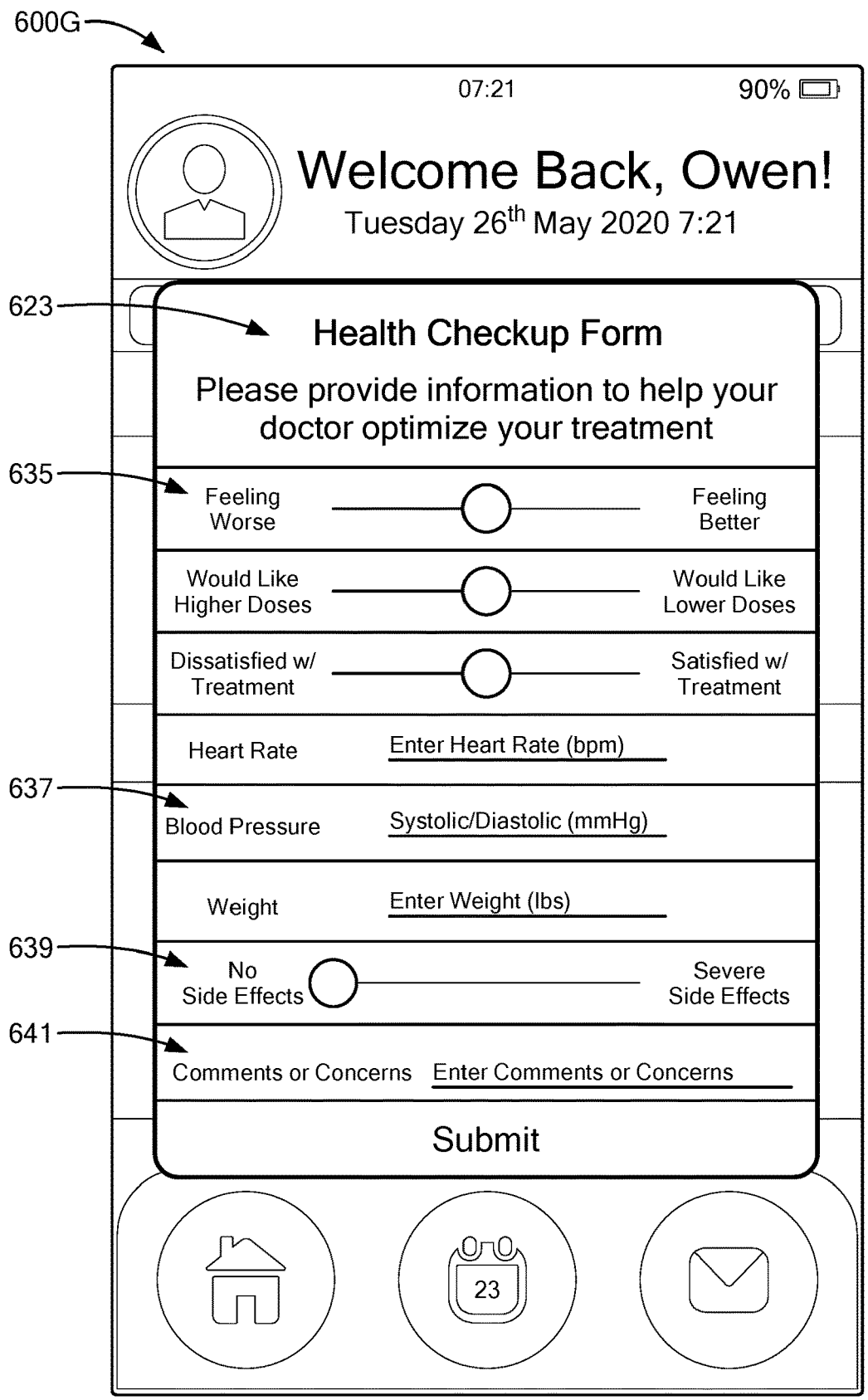

Health checkup form 623, depicted in FIG. 6G, uses slidebars 635 adjustable by the patient to reflect a rating of feeling worse to feeling better, wanting higher or lower doses, and being satisfied or not with the treatment progress. Requests for manually-input biometric data 637 enable the patient to send "easy to collect" biometric data back to his/her HCP. As side effects are often a concern of doctors, a side-effects inquiry 639 inquires into the severity and type of side effects, which pops up in a separate window found in F6H. Lastly, a free response comment section 641 is supplied to allow patients to give any feedback that does not concern one of the subjects already covered.

Figure 6H:
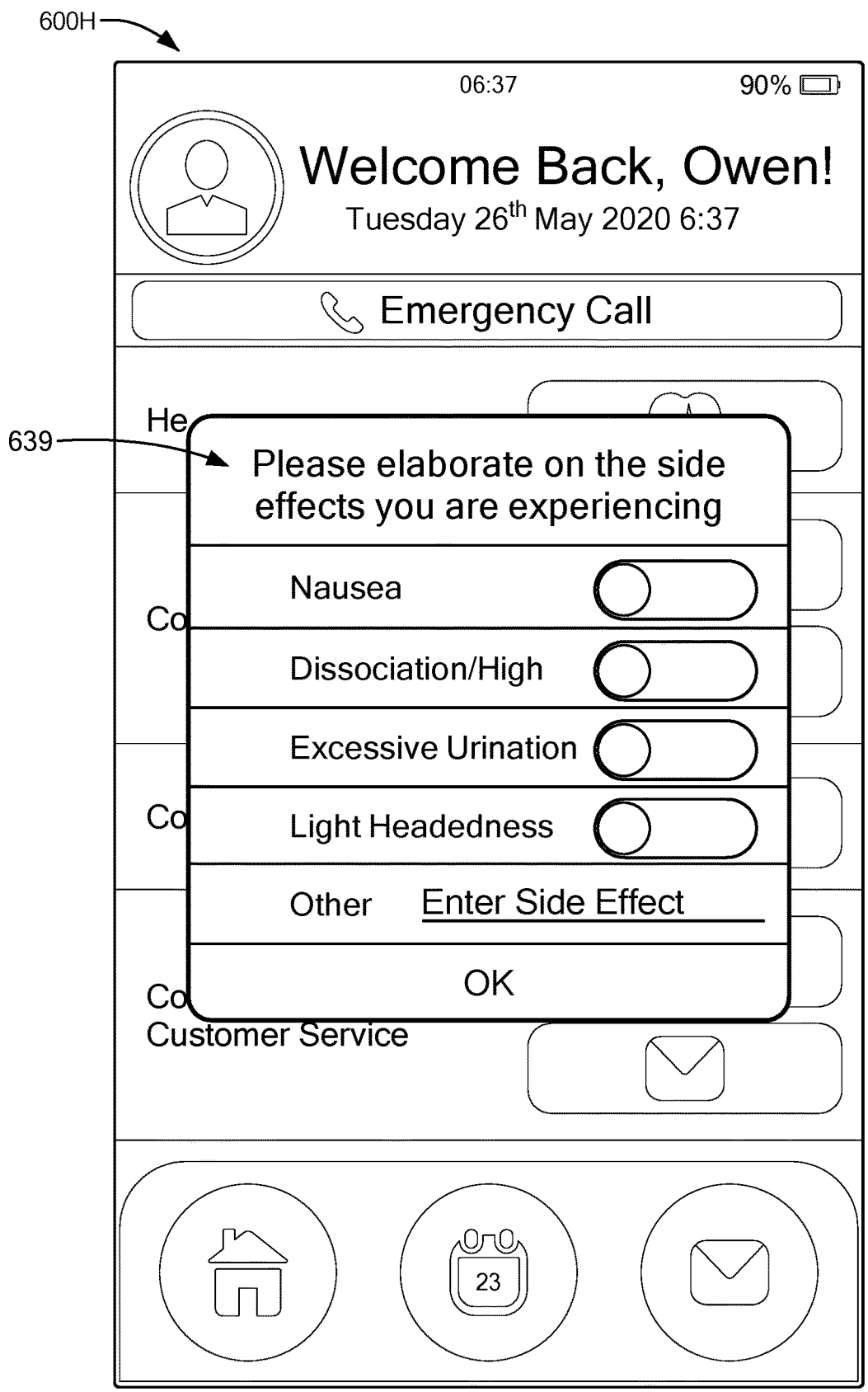

A side-effects display page 600H is presented in FIG. 6H. Display page 600H depicts side effect inquiry 639 including a request for additional details regarding which side effects the patient is experiencing. Display page 600H receives patient selection of software switches displayed adjacent to specific side-effects which may occur when taking the prescribed medication. The likelihood of occurrence, based on clinical trial and post-market reports, may be used to order the potential side-effects. In addition, data entry fields are included in display page 600H to receive patient-entered text providing additional information related to the selected side effects, or to identify side effects not listed as a selectable option.

Figure 7:
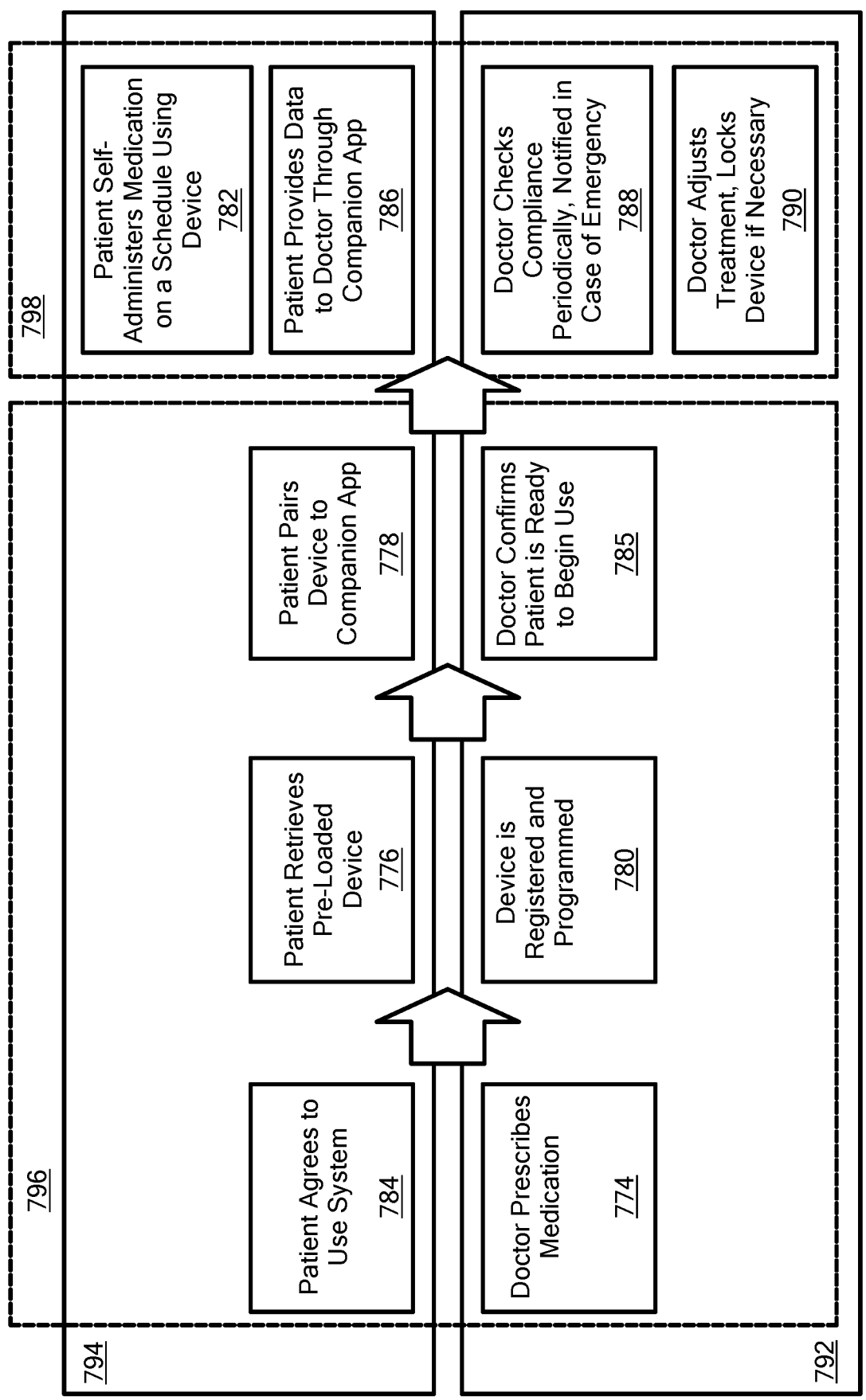
FIG. 7 is a flowchart of an embodiment of a method for the use of a system of the present invention.

FIG. 7 is a flowchart of an embodiment of a method for the use of system 501. Prior to the patient 594 using device 500, a series of steps or functions 796 are performed. After steps 796 are performed, regular use of the system 501 can begin, which entails steps 798. All blocks vertically aligned with each other may occur concurrently. The upper half of FIG. 7, labeled 794, includes those blocks which describe actions performed by patient 594. The lower half of FIG. 7, labeled 792, includes those blocks which describe actions performed by doctor 592.

At block 774, a doctor or other health care provider (HCP) 592 prescribes medication to the patient. This prescription 574 includes the medication, patient-specific dosage and schedule information, concentration (if the medication is to be compounded) and/or other prescription parameters. The same prescription or different unique information may pair device 500 to the prescribed medication contained therein and given patient. Patient 594 may receive the device filled with medication from pharmacy 551 or HCP 592. Alternatively, device 500 is brought to pharmacy 551 to be filled with the prescribed medication, or the medication may be acquired elsewhere. It should be appreciated that a patient may obtain device 500 in myriad ways; the prescribed medication on the other hand is dispensed by pharmacy 551 or other authorized HCP, or delivered by mail. Distribution of the prescribed medication 576 may be conditioned on the patient taking particular actions which may include but are not limited to use of system 501, acquisition of the device 500, installation of a companion application 573 on the patient's smartphone or other computing device 568, and acquire any additional external devices 572a deemed necessary by HCP 592.

At block 784, the patient agrees to use system 501 and device 500 and undergo any necessary prerequisite training. The doctor may be the one to recommend or require using system 501, or perhaps the patient, a family member of the patient, or another doctor recommends or requests the use of the system.

At block 776, the patient retrieves a pre-filled device. As noted above, some embodiments of device 500 are disposable while others are refillable. Prefilled device 500 may have been filled by pharmacy 551, the pharmaceutical company manufacturing the prescribed medication, or other authorized entity or individual.

A description of one possible method for filling device 500 with a full Rx dose 576 of a prescribed medication is as follows. Once the doctor transmits prescription 574 to pharmacy 551, the doctor and pharmacist will communicate as needed. It is common practice for doctors to communicate with pharmacists when prescribing compounded medications.

The pharmacist may also ask the doctor's office to unlock the refill hatch 132 of the device 500, which can be done exclusively through the HCP interface 566. The unlocking command 532 is transmitted from the patient management software 561 to the command subassembly 503 on device 500. Other possible embodiments of this process could include a method for the pharmacist to personally input parameters to the system via a pharmacist-specific software or website, and/or unlock the device's refill hatch directly, such as with a manufacturer-issued traditional key or key fob. In other embodiments, the device is disposable and only gets filled once.

One embodiment of system 501 has disposable devices which come pre-filled from the manufacturer. Once hatch 132 is open, the pharmacist can load in the medication and when done will close it, at which point the hatch will automatically relock and the device may notify the server that it has been successfully refilled. The return of the loaded device to the patient may be confirmed in the system by the patient via the patient interface. The system could be designed so as to notify all users when it is approaching empty.

At block 780, device 500 is registered and programmed. This programming may include but is not limited to patient identity, dose quantity, dose schedule, and any prerequisite requirements to be met prior to the patient being able to take dose. These prerequisites to administrations may for example be values or ranges of values for different parameters selected by the HCP based on the prescribed medication, patient's health, other medications currently being taken, trustworthiness/other risk factors of the patient, or any factor. Exemplary prerequisite requirements are further described below with reference to FIG. 8.

This programming may be on any number of system components, for example patient management software 561 or on on-board command subassembly 503. This programming may occur before or after the patient receives device 500. One embodiment of the filling process above requires this programming to be done during the filling process, perhaps by the pharmacist themself, or responsibility could fall on the doctor, pharmacist, manufacturer, or other qualified entity. This programming could occur remotely utilizing software on the server 562, or may require having the physical device 500. In one embodiment of this process 780, the doctor accesses the HCP interface and inputs the patient's device ID into the centralized online system 501. Software assigns a code to the patient's device, retaining all of the patient identification information on server 562. In some embodiments of this process 780, the patient inputs their device's unique identifier into the system, for example through companion application 573, website, or phone call. Such a device identifier could be in any form and be input via any method, for example an alphanumeric sequence that is manually typed in, encoded in a barcode that is scanned, or transmitted wirelessly via bluetooth or NFC.

At block 778, the patient 594 establishes access to patient interface 570 on patient's smartphone 568 or equivalent device. The process of obtaining and installing any software may be done with the help of an HCP, or could be a part of the prerequisite training 784 or registering/programming 780. Once process 778 is complete, all system 501 users and integrated softwares and devices are paired with one another through server 562, and the patient has an updated entry in the database 564. This process may include for example downloading a companion app 573 and logging into their patient account and pairing bluetooth devices such as 500 and 572a to a smartphone.

At block 785, doctor 592 confirms patient 594 is ready to begin treatment using system 501. This confirmation may take place directly through system 501 for example through a prompt received on companion application 573, over the phone, in person, or through any other method of communication. This confirmation may include ensuring the patient has all necessary devices, software, and training.

At block 782, patient 594 executes patient control actions 553 on device 501 to self-administer a dose 582 of prescribed medication in accordance with dose schedule 547. An embodiment of process 782 is described in greater detail below in FIG. 8.

At block 786, patient 594 regularly uses patient interface 570. Patient uses patient interface 570 for data collection 586, which may include feedback 523 and input biometric information 537. The patient also may use patient interface 570 for access to information on patient management software 561 on server 562 using oversight tools 571.

At block 788, HCP 592 utilizes the monitoring functions of system 501, which may include but is not limited to the review of monitored parameter data 588, by checking compliance periodically through HCP interface 566, receiving notifications in case of emergency, and direct communication with the patient 594.

At block 790, HCP 592 utilizes the regulating functions of system 501, which may include but is not limited to the initiation of control commands 590, adjusting treatment or shutting down device 500 if necessary through HCP interface 566 or otherwise modifying patient experience.

There exists a family of embodiments in which HCP 592 modifies control signals 590 using HCP interface 566. These modifications may include, but are not limited to, all patients within the HCP's practice, a subset of patients, or a single patient. These modifications may include, for example, dose prerequisites 867 (described in detail below with reference to FIG. 8), a patient's prescription quantity 545 or schedule 547. HCP 592 may also in some embodiments have the ability to modify other aspects of the patient experience and data collection as well for example contact information for HCP 592, companion application 573 features, or use of additional sensors. For the purpose of illustration, HCP 592 may require the completion of a survey prior to or after a dose is made available for administration, on a specified interval, or a combination thereof.

These modifications may be preplanned, requested by the patient, or chosen by HCP 592 for other reasons. HCP 592 may make an unplanned modification upon receipt of new data, which may include for example diagnostic or other data or information from any number of sources which may include but is not limited to system 501, an in-person visit and any tests which may have been conducted therein, pharmaceutical or device manufacturer, insurance company, or otherwise. For example, HCP 592 may adjust treatment based on patient parameters, such as by adding an additional survey for patients with a PHQ-9 score below a threshold, reducing dosage based on higher than expected blood pressure, and starting to require the direct oversight of a nurse based on suspected tampering. Note that the use of any data or the use of analyses of any data generated through the use of system 501 may or may not be for diagnostic purposes. In some embodiments, these modifications may be made in real time. For example, HCP 592 may add an additional survey for a patient to take prior to self-administering a dose, and this modification is reflected the next time a patient is to self-administer a dose.

Such modifications to control signals 590 may take effect at any number of times or upon any number of conditions being met. HCP 592 may or may not have restrictions on what can be modified and when. For example, it may be beneficial for some changes to occur only upon the start of a new prescription, most notably should the modification be to medication concentration or composition.

Figure 8:
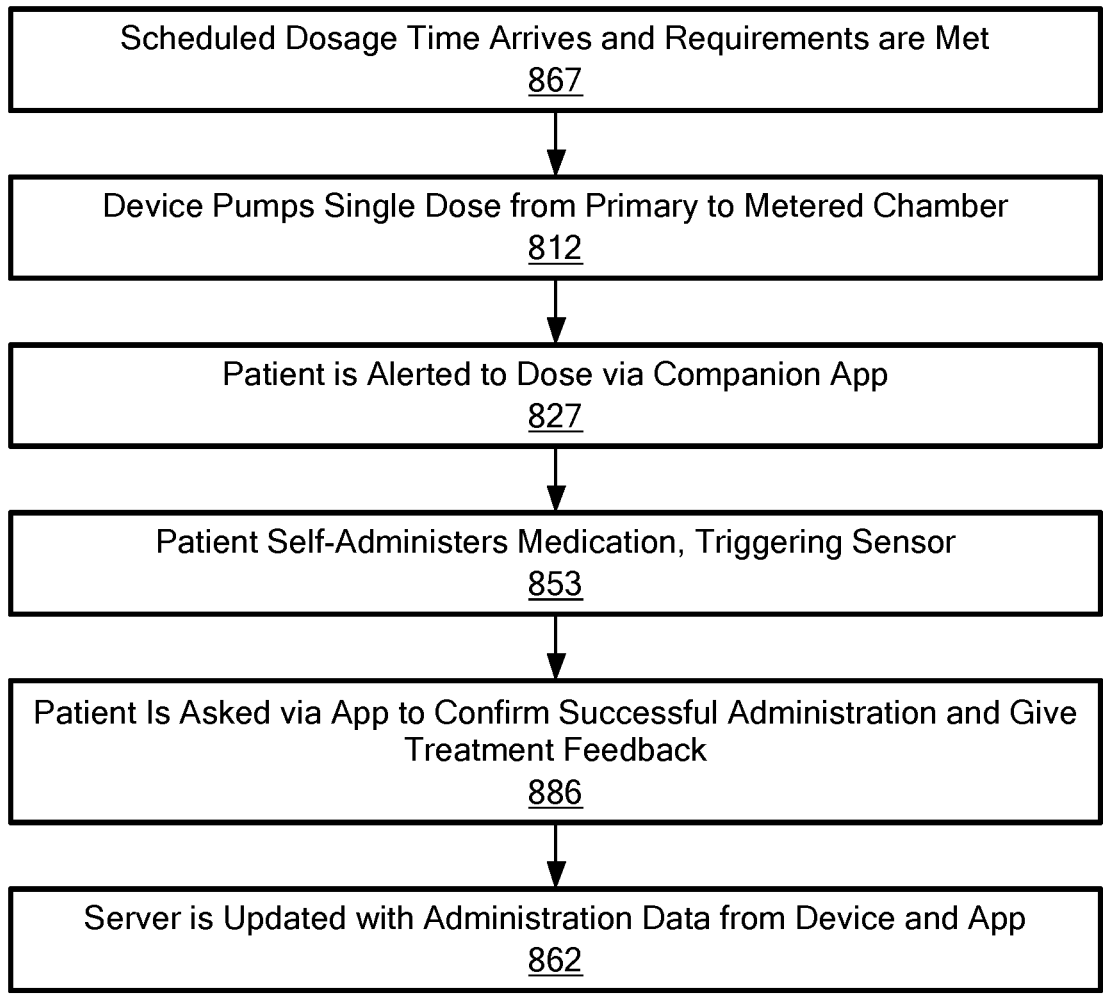
FIG. 8 is a flowchart of an embodiment of a method for the self-administration of a dose of medication using a device of the present invention.

FIG. 8 describes in detail one embodiment of process 782 of self-administering a dose of medication.

At block 867, when a scheduled time arrives at which a dose should be administered, command subassembly 503 or patient management software 561 on server 562 first confirms that current data from any required accompanying devices is within an approved range. That is, before administration of a dose can be made possible, certain parameters, specified by an HCP upon prescription or some other time, must be satisfied. These requirements may include, for example, the patient having a certain health status verified by sensors, the patient inputting certain data into the interface 570, signing an agreement saying they won't operate heavy machinery for a certain period of time after self-administering the medication, confirming that the user is ready and able, confirming the user's identity with a fingerprint scanner or camera, or any other requirement deemed necessary by the HCP.

At prerequisite verification block 867 in some embodiments, certain other parameters are confirmed to be within their respective desired range. Such parameters include but are not limited to one or more of the following parameters: completely successful administrations up to present, sufficient volume of medication remaining to constitute a desired quantity of doses, the absence of a detected tamper event, adequate device battery charge, adequate wireless signal connectivity between device 500 and World Wide Web 559, and successful server 562 connectivity via patient terminal 568. Data may be input manually by the patient or may be obtained directly from a sensor onboard device 500 or external device 572a. Such sensors may for example measure heart rate, blood pressure, or blood glucose level. If such data is not immediately available, the server prompts the patient via smartphone to make the data available by, for example, blowing into a breathalyzer.

Additional parameters that must be met within prerequisite 867 may include but are not limited to: the time elapsed since the prior dose was taken, proximity to dose time set in schedule 547, patient compliance up to the present, the patient's completion of a survey on terminal 570, reception by the device of updated control signals 590, and both HCP and patient being present on a video call. For example, if a patient has taken a dose near the time of their next dose, their next dose may not be made available for administration. This may be done by preventing the patient from taking their next dose entirely, or requiring the patient to wait a period of time before taking their next dose, wherein these margins may be configurable by HCP 592. For the purpose of illustration, a scheduled dose may not be made available should it be determined that the prior dose has not yet been administered, for example to prevent the patient from taking two doses at once and to prevent excess medication from being transferred to a chamber which cannot contain it. In some embodiments, schedule 547 may model, copy, or utilize scheduling data used in other electronic health record (EHR) systems.

In some embodiments, prerequisites 867 are stored remotely on database 564, which may allow HCP 592 to modify these requirements at any time using HCP interface 566. Such modifications may be desired by the HCP for example due to changes in the patient's medical condition or trustworthiness over time. The determination as to whether dose 582 is to be made available by command subassembly 503 in some embodiments is made by software 561 stored on the server 562, while the data used to make said determination is collected from any number of sources. For the purposes of illustration, some prerequisites may involve confirmation of patient identity and health parameters being within a safe range, and the data to make such determinations may originate from monitored subassembly 522, patient terminal 568, and external devices 572a. In other embodiments, the software to make the determination as to whether or not the command subassembly 503 should make a dose available, including verification of the applicable prerequisites, may be stored on device 500 or patient terminal 568 to enable full operation without internet connection. In embodiments where such determination is made without internet connection, locally transmitted data may be taken into account, for example data transmitted via bluetooth between the device, patient terminal, and any external devices.

At block 812, once the parameters are confirmed to be successfully met, patient management software 561 on server 562 will command the device 500 to make a dose available to the patient for self-administration. For device 200 for example, this would include the pumping of one dose from the primary chamber 208 to metered chamber 210.

At block 827, patient 594 is alerted to the availability of a dose. This could occur through the patient interface 570 using a popup such as notification window 627, or through any other method, such as an automated phone call, text, or email, or device 500 alerts the patient with a noise or LED indicator.

In block 853 the patient self-administers a dose 582 of the prescribed medication, possibly in multiple increments 583. The patient controls delivery interface 504 though application of patient control actions 553. In the nasal spray embodiment of FIG. 2 described above, patient control actions 553 include the manual depression of spray nozzle depressor 238. The administration of the prescribed medication is confirmed using administration event data 526b collected by monitored subassembly 522. Alternatively or additionally, such a confirmation may be obtained by monitored subassembly 522 based on detected fluid levels in regulated subassembly 506. The device records the timestamp of dose administration, which is sent to patient management software 561 executing on server 562, which will store the device's timestamped administration confirmation along with the health parameters recorded before dose partitioning. This information is stored in patient database 564 for subsequent presentation to the doctor.

In block 886, after administration has been detected in block 853, the patient is prompted, via patient interface 570, to confirm successful administration and enter into patient interface 570 treatment feedback, utilizing the data collection function of the user interface 586, possibly including input biometrics 537 and/or feedback 523. This step may be performed through interface functionality possibly resembling health checkup form 623 and/or side-effect inquiry 639. This would also be the time at which a patient 594 can report an error in administration, possibly through a button such as 631 or through contact page 600D.

In block 862, server 562, and database 564, are updated with data concerning the particular administration event from device 500, patient interface 570, and any external devices 572a. This is likely not to be its own step in the process, and rather would likely happen throughout the self-administration process steps described herein with reference to FIG. 8. This is due to the fact that some data is required by patient management software 561 prior to administration, per prerequisites confirmed at block 867, and patient management software 561 is made aware of an administration event in real-time as discussed herein in connection with block 853, as to prompt block 886. The data is processed through patient management software 561 on server 562 and logged into database 564. Software 561 may calculate the remaining amount of medication in device 500. If the dose could not be partitioned because one of any of the above parameters were not met, or an error was reported during administration, the device will also record which parameters were not met and store this in the database 564, while notifying the doctor 592 that a dose could not be taken and the associated causes. Patient interface 570 and HCP interface 566 are both updated to reflect this data, which may include, for example, the resetting of countdown timer 609.

Some embodiments of device 500 have a removable primary chamber or cartridge 108, 208, 308, where either pharmacy 551 or HCP 592 is responsible for replacing when the medication is depleted, which may be after the administration of any number of doses, which may for example depend on the capacity of the multi-dose chamber or the number of single-dose cartridges.

While some embodiments of regulated subassembly 506 of device 500 include a dedicated medication transfer mechanism, such as pump 212 and extractor mechanism 312, others may restrict access to a single dose of medication through methods which do not entail the physical transfer of medication. For example some embodiments of regulated subassembly 506 include a single chamber for medication accessible to the delivery interface 504 while restricting how much and at what times patient control actions 553 can be performed. One such embodiment includes a mechanism which locks and unlocks the nasal spray depressor, allowing it to be depressed only a specified number of times (the sum of such applications constituting the administration of a single prescribed dose) and on a specified schedule. Other such embodiments may limit patient control actions 553 based upon data from a fluid flow sensor, fluid volume sensor, or any other sensor which may indicate when one dose has been administered.

In some embodiments of device 100 and 200, both reservoirs are part of a single assembly that is one of a set of such assemblies that are specifically configured for approved dosages and refill durations. For example, one assembly will have a secondary reservoir with a capacity for a first prescribed daily dosage of a particular medication and a primary reservoir with a capacity for a 30 day supply of that dosage of the medication. A second assembly of the set could have reservoirs with a capacity that is 50% greater than the capacity of the corresponding reservoirs in the first assembly to accommodate a second prescribed daily dosage that is 50% more than the first prescribed daily dosage.

In some embodiments of system 501, external device 572a may be ingested, inserted, implanted, or injected into the body of the patient, possibly for the detection of medication concentrations or the detection of chemicals which may make administration of the medication dangerous. For example, such a sensor could be used to confirm administration. In another example, such a sensor is used to confirm a lack of illicit substances in the patient's body prior to making a dose available for administration. Alternative embodiments of such a device or sensor may be incorporated into the medication itself, for example a nanobot within an ingestible pill.

In some embodiments of system 501, dosage schedule 547 may not be a set of predetermined times but rather a set of predetermined criteria, which, if met, indicate the arrival of a scheduled dose. For example, should the medication be insulin, device 572a may be a blood glucose monitor, and only when the patient's blood glucose level is measured to be above and/or below a threshold does device 500 make a dose of insulin available.

Figure 9:
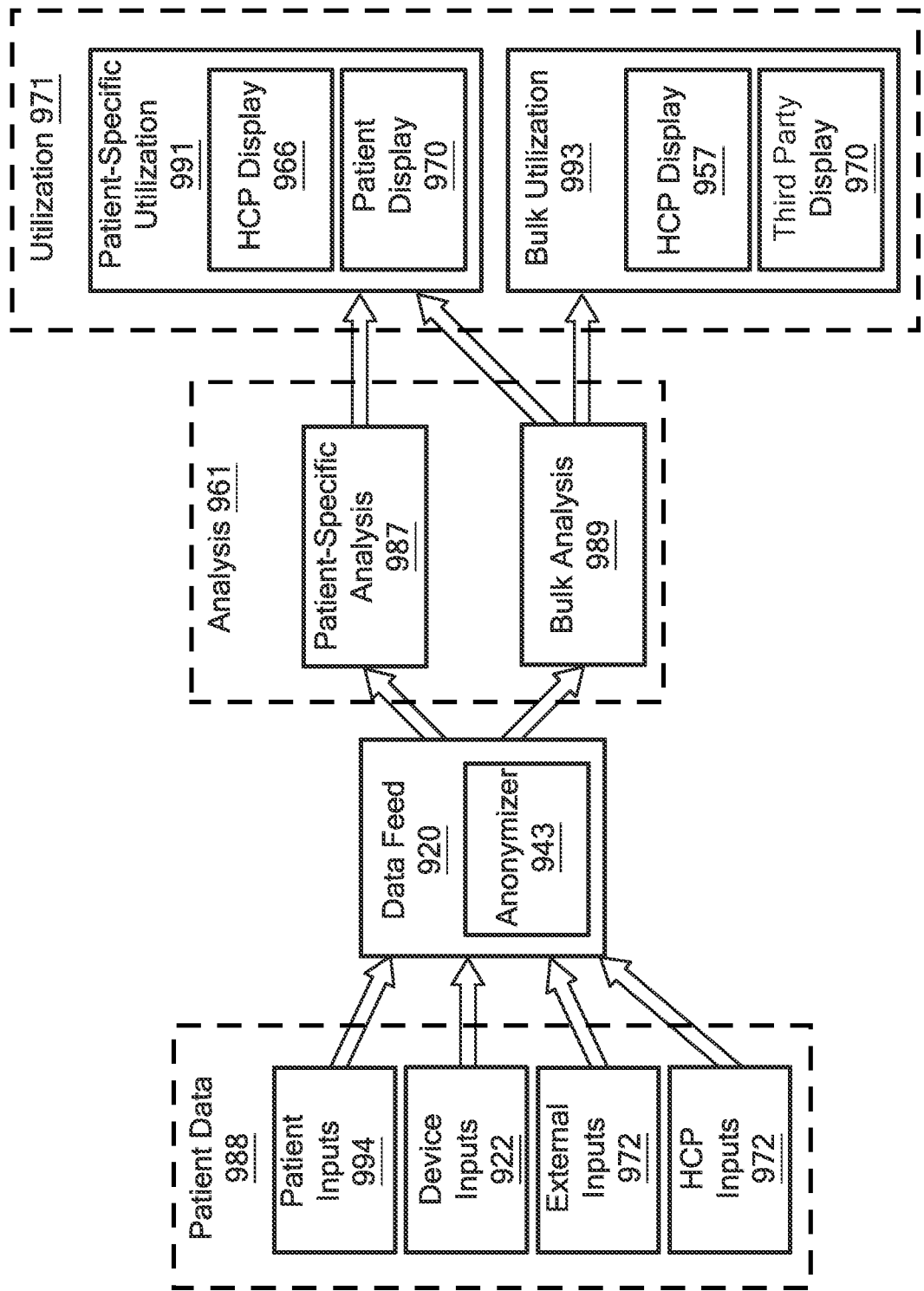
FIG. 9 is a schematic block diagram of one embodiment of the information and data flow through a system of the present invention.

FIG. 9 is a schematic block diagram of information and data flow through system 501 for the analysis of patient data and its presentation to and utilization by patient 594, HCP 592, and third parties. Patient parameters 988 are collected from a variety of sources and the subsequent consumption of that data, including analysis 961 and utilization 971, may occur on server 562, for example using software 561 or database 564, on HCP terminal 557, HCP interface 566, patient terminal 568, patient interface 570, or anywhere else within or external to system 501. Patient parameters 988 includes data 994 which is input by the patient 594, data 922 which is input by device monitoring subassembly 522, data 992 which is input by HCP 592, external sources 972, and any other data collected by any component of system 501.

Patient input data 994 is any data input into system 501 directly by the patient, for example via the data collection features 586 on patient interface 570, which may be companion app 573, and may include but is not limited to input biometrics 537, input feedback 523, and may collect user identification data such as authentication confirmations through a password, fingerprint sensor, or camera. This may include, for example, data input as a prerequisite to administer a dose or after a dose was administered, such as the results from health form 623 and side effects inquiry 639. Data 992 is directly inputted by HCP 592 through HCP interface 566 and may include but is not limited to prescription 574, commands 590, dose quantity 545, dose schedule 545, commands 590, and/or patient history or medical records. Device monitoring data 922 is collected by device 500, and may include but is not limited to user ID 543b, onboard biometrics 530b, fluid level 528b, tamper events 524b, administration events 526b, and device state 560b.

External data 972 is collected by any external source which interfaces with system 501, which may include but is not limited to external devices, such as external devices 572a, the servers of companies which collect data directly from external devices, healthcare system infrastructure for hospitals and pharmacies, government records, and EHRs. External data 972 may include but is not limited to biometrics 572b and any health parameters collected such as blood pressure, heart rate, blood oxygen, weight, steps walked, blood alcohol content, glucose levels, and concentration of medication or its metabolites in the blood. It also may include user identification data collected from any external devices, such as fingerprint and facial data, and any other data such as that collected by GPS, automotive interface, patient terminal, and camera. It should be appreciated that in some embodiments external data 972 may include data collected by external devices in a hospital, hospice, or nursing home. Such devices may include active monitoring equipment and/or diagnostics such as EKG, and may be configured to interface with system 501, for example by transmitting data directly to a system 501 component such as patient terminal 568 or HCP terminal 557 via bluetooth or wifi, or indirectly, for example via the internet from a third party server.

While external data 972 includes data collected by external devices which interface with system 501, some external devices do not. This data may instead be manually input by the patient, for example through patient terminal 568, and included as part of patient input data 994. Or it may be manually input by the HCP, for example via HCP terminal 557, and included as part of HCP input data 992. Some examples of this type of data include data input by the HCP as recorded during clinical diagnostics, for example health parameters, blood test results, and x-ray images following a routine checkup, and data input by patients such as medical history details and measurements from analog devices such as a traditional scale.

Patient parameters 988 are fed through data feed 920 before analysis 961 is conducted. There may exist overlap between external data 972, HCP input data 992, device monitoring data 922 and patient input data 994. Data feed 920 may filter out such redundant data, for example based on time of measurement or acquisition or based on prioritization of source. Data feed 920 may also include anonymizer 943 that contains functionality to anonymize patient data, which may be required for bulk analysis 989 and utilization 993.

Analysis 961 includes patient-specific analysis 987, which uses patient parameters 988 for one patient, and bulk analysis 989 which uses both raw data from data feed 920 and results from patient-specific analysis 987. This analysis may occur upon the HCP requesting said analysis, additional data being added to the database, or on any other schedule, and may include data processed for visualizations, consolidations of data, execution of algorithms for the generation of quantitative data analytics such as statistical analyses, identification of trends, and outcome measures. In some embodiments, the HCP is capable of adapting the analyses that are conducted on their behalf, for the purposes of conveying the most useful data in a manner most optimal for a given HCP and their goals. HCP interface 566, for example, may enable the HCP to request specific analysis be conducted using specific data. Analysis 961 may occur in one or many locations, for example on server 562 executed by patient management software 561, or by HCP interface 566 or patient interface 570.

Patient-specific analysis 987 consumes raw data for one patient and outputs analyzed data. Patient-specific analysis 987 may include, but is not limited to, trends, correlations, distributions, or any number of functions or algorithms. For example, determining correlations between one or more patient parameters over time. For the purpose of illustration, this may be calculating the correlation coefficient between PHQ-9 scores as collected as part of data 994 and body weight as collected by internet connected scale as part of data 972. Another example of analysis 987 is the calculation of distributions of when the dose is taken, which may then be utilized by the HCP and patient to find a more optimal dose schedule.

Bulk analysis 989 can consume both raw data generated from data feed 920, and results from patient-specific analysis 987. Bulk analysis 989 generates analyses taking into account multiple patients, while patient-specific analysis 987 takes into account a single patient for any given analysis. These analyses may be determined for example by HCP 592, drug or device manufacturers, or by those conducting clinical trials. This data may be anonymized, pursuant to jurisdictional policy. Bulk analysis 989 may comprise any number of analyses to investigate any number of factors. For example, analysis of correlations between patient parameters, for example statistical analyses comparing compliance and medication, compliance and dosage, compliance and tamper events, compliance and schedule, side-effects and dosage, side-effects and tamper events, dosage and blood pressure, dosage and pain levels, three-dimensional cross-correlation of age, compliance, and dosage, or any other comparison. Bulk analysis 989 may include utilizing machine learning to build predictive models, for example to demonstrate effects of a medication on certain vitals based on any number of factors. Bulk analysis 989 may also include analyses involving the patient's genome, for example side-effects or medication uptake may be correlated with one or multiple genes. These analyses could be determined based on objectives including for example identifying risks in a treatment, determining the safety and efficacy of a given medication and proposed dosages and schedules, locating the source of a problem in a broader system, optimizing instructions for use of a product, discovering new applications of existing treatments, or determining ideal treatment for a patient with a given set of conditions. Patient data can be analyzed with reference to literature and standard data. Specific analytics which may be conducted may include but are not limited to t-tests and one-, two- and three-way ANOVA tests and p values, regression curves and R values, probabilities, averages and standard deviations, distributions, and correlation coefficients. Bulk analysis 989 may be requested and customized for the needs of various parties in and adjacent to the system, for example patients for the optimization of self-administration timing, doctors for the optimization of medication and dosage, nurses for the optimization of their own time management, insurance companies for the optimization of investment impact and risk reduction, device manufacturers for the optimization of use of their devices concerning medication uptake and patient compliance, pharmaceutical manufacturers for the optimization of medication indications and side effects warnings, and local governments for the optimization of resource allocation for public services. Such analyses can be requested by these parties through various means, including but not limited to their given interface 570 or 566, third party interface 1065 (described below in reference to FIG. 10), and through direct communication with system customer service representatives and application engineers. Bulk analyses can in some embodiments be initiated by the system itself for example for use in determining prerequisites for a patient to be given access to a medication dose, for recommending to HCPs optimal treatments given the patient condition and medical history based upon the experiences of others, for determining when to send a notification to an HCP or patient indicating possible risk for the experiencing of a side-effect, and for determining what recommendation to make to the patient to improve their self-administration experience.

Utilization 971 includes patient-specific utilization 991 and bulk data utilization 993. Utilization 971 presents data from analysis 961 to desired entities. This may be, for example, for the purposes of optimizing a patient's treatment, diagnosing conditions, monitoring potential health issues of one patient or within a group of patients, or researching the efficacy and safety of a given treatment or set of treatments. HCPs, patients, or third parties may be presented data as part of utilization 971 pursuant to relevant laws. For illustration, utilization 971 may be in the form of graphs and tables and may convey any trends and correlations within the datasets. Some examples of data which may be presented includes but is not limited to, trends and correlations between tamper events, administration events, overall compliance over time, administration time deviations, health parameters, sensor data, survey results, and PHQ-9 scores.

In patient-specific utilization 991, data from patient-specific analysis 987 are presented to HCP 592 or the patient. For example, this may include visualizations of trends in improvement over time, vital signs over time, and compliance over time. This data may be compared to known standards from literature or to data from bulk analysis 989. For example, a chosen patient's data may be compared to bulk data from patients in any number of distinguished groups, for example other patients within the given HCP's practice or even more specifically patients within the practice on the exact same treatment. Other such groups of patients may include those outside of the given HCP's practice, instead including any patient on a specific medication, in a specific region, with a specific condition, or other such large, anonymized grouping.

Bulk data utilization 993 includes data analyzed from multiple or all patients in any form, for example visual or tabular form. Visualizations may include graphs and tables. Non-visual data may be stored electronically, and provided to users through an API, a database interface, data files, or any other method. For example, drug manufacturers may use analyzed survey results to make decisions on dosage or dose schedules. Clinical trials may use this data to gauge the success of treatment for patients within the clinical trial. Bulk data utilization 993 may be used for all patients in one practice. For the purpose of illustration, a hospital might use bulk analysis 993 to drive treatment decisions, or generate an overview on treatment progress for all patients.

Figure 10:
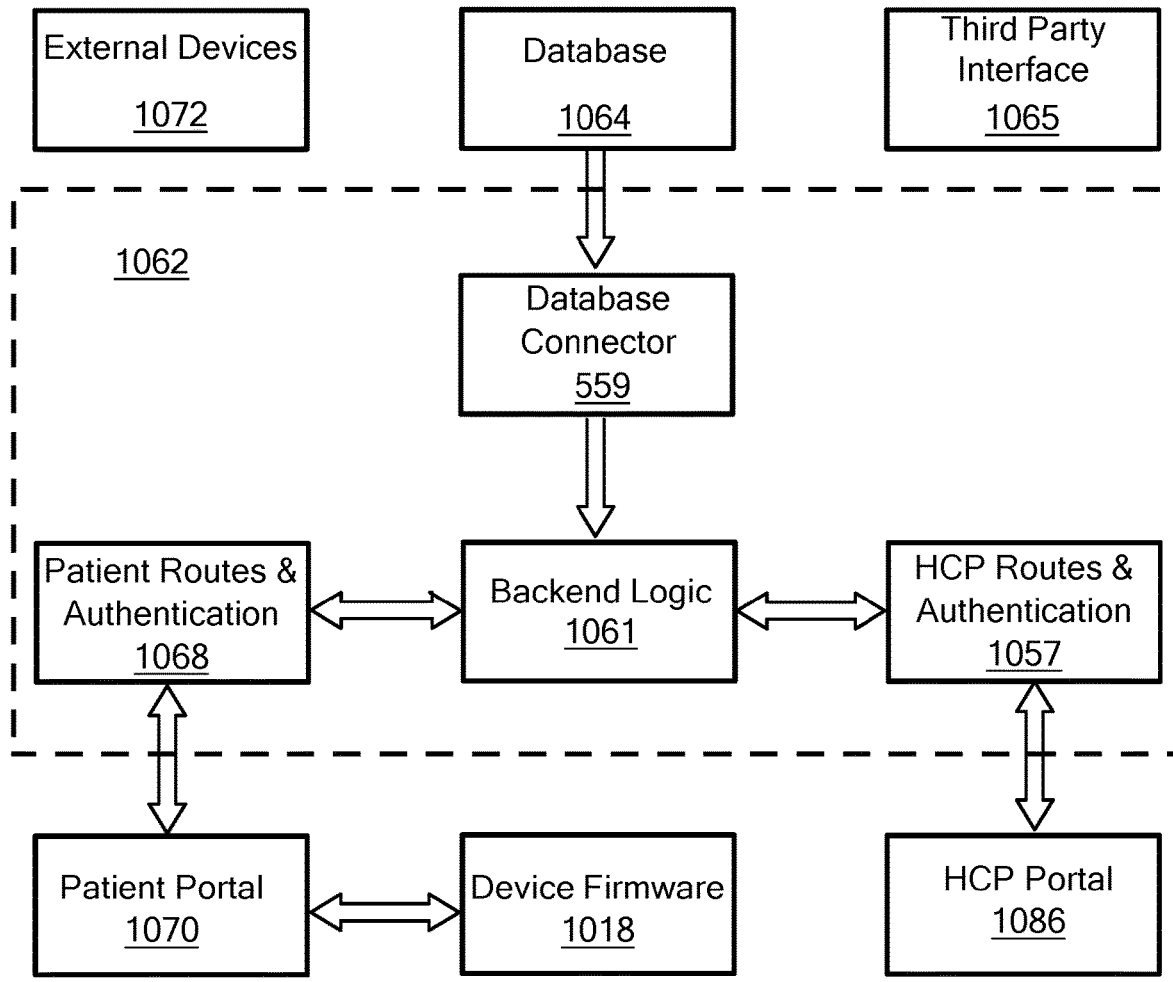
FIG. 10 is a schematic block diagram of one embodiment of the information and data flow through a system of the present invention.

FIG. 10 is a schematic diagram of information and data flow in one embodiment of the system, detailing the path of data from its source, for example devices such as drug delivery device 500, patient terminal 568, and external drug delivery device 572a, to its destination, for example database 564 and external parties' systems. The path this data takes will have impacts on data security and HIPAA compliance, as well as system performance, user experience, and in determining which data can be utilized and in what ways. FIG. 10 includes a data-flow structure that allows data to be collected centrally and then distributed in a controlled, secure manner.

Backend 1062 manages patient and HCP data, collates and analyzes information, enables connectivity to patient devices, handles the storage and retrieval of data from database 1064, and interfaces with third parties. In one embodiment, a substantial portion of the functionality of backend 1062 exists within backend logic 1061, which processes data generated from the patient, HCP, third parties, or any number of sources. This may include but is not limited to data 988 and data generated from backend 1062. Backend logic 1061 may perform functions such as correlating identifiers, determining the source and destination of data, conducting analysis 961, or functionality relating to patient management software 561, for example determining whether a dose should be made available. The remaining components of backend 1062 serve to assist in the distribution and collection of data to and from their intended destination.

Patient routes & authentication 1068 enables the connectivity between patient portal 1070 and backend logic 1061, whereas HCP routes & authentication 1057 enables the connectivity between HCP portal 1066 and backend logic 1062. These routes & authentication components include all endpoints that patient portal 1070 and HCP portal 1066 may use respectively. In one embodiment, these endpoints exist as HTTP request methods, for example it may consist of GET and POST requests. It may also provide a method for securely authenticating patients such that unauthorized users cannot access backend 1062. For the purpose of illustration, this may be done using authentication tokens such as JWT that are attached to the data sent from patient portal 1070. Patient routes & authentication 1068 selects which pieces of data the patient must send to backend 1061 and which pieces of data the patient may retrieve. Data may be selectively filtered out for the purposes of performance or data security.

Patient portal 1070 is an implementation of patient interface 570. Patient portal 1070 may communicate directly with device firmware 1018, and as such, the terminal 568 on which it resides may include capabilities such as bluetooth. In some embodiments, patient portal 1070 is a web application that may be accessed through any web-capable device. In some embodiments, patient interface 570 is companion application 573 and in some it resembles the interface of FIGS. 6A-H. For the purpose of illustration, patient interface 1070 may be hosted on a particular website that may require an SSL connection. In other embodiments, it exists as a native application on one or more platforms.

Device firmware 1018 exists on device 500, enabling proper device function, for example that of monitoring subassembly 522, control subassembly 503 and communication module 520, as well as error handling. Communication with backend 1062 is necessary for the functioning of the device, as data is both collected and received by the device. In some embodiments, this communication with backend 1062 could occur directly, and in others, including the embodiment of FIG. 10, indirectly via patient portal 1070, which may have internet connection while the device may not.

HCP routes & authentication 1057 enables the connectivity between HCP portal 1066 and backend logic 1062. Data such as patient settings and analysis 961 may be requested and transmitted to HCP portal 1066. As with patient routes & authentication 1068, HCP routes & authentication 1057 may or may not include HTTP endpoints and security measures.

HCP portal 1066 is an implementation of HCP interface 566. HCP portal 1066 communicates with backend 1062 through HCP routes & authentication 1057 to provide HCPs with relevant patient data and methods for monitoring and controlling a patient's treatment. HCP portal 1066 may include utilization 971, such as patient-specific utilization 991 and bulk data utilization 993.

FIG. 10 is an embodiment of system 501 wherein external devices 1072 communicate and interface directly with backend 1062 and wherein third party systems also interface directly with backend 1062. There are alternative embodiments where external devices 1072 communicate indirectly with backend 1062, for example through patient portal 1070, HCP portal 1066, or third party interface 1065.

Third party interface 1065 allows system 501 to communicate with an external system not included in system 501, for example a patient management system or medication management system or combination thereof. This may include an EHR system, pharmacy prescription system, or government health service system. Third party interface 1065 may include functionality utilizing an API provided by the third party, and/or functionality utilizing an API that is a component of the present invention, and some utilize a combination thereof. Examples of data exchanged with interface 1065 may include but are not limited to any data included in data 988. In some embodiments, data from third party interface 1065 may be used to determine prescription information and leverage functionality to determine dose availability for the patient. In other embodiments, data collected through third party interface 1065 may be combined with diagnostic or usage data from Data Collection 586 to provide improved treatment or compliance analysis for HCP 592. In embodiments in which external devices 1072 communicate exclusively with an external system, they may interface with backend 1062 via an external interface 1065. FIG. 10 describes an embodiment in which the third party interface 1065 communicates exclusively and directly with backend 1062 and where external device 1072 communicated directly with backend 1062 via its own internet connection. However in some alternative embodiments, one-way or two-way communication with third party interface 1065 may take place with backend 1062, patient portal 1070, HCP portal 1066, external device 1072, or any combination thereof. In some embodiments, system 501 is incorporated with a third party system wherein system 501 is integrated as a subcomponent of the aforementioned third party system, and third party interface 1065 enables communication between system 501 and the parent, third party system.

Database connector 1020 enables communication between database 1064 and backend 1062. Database connector 1020 may include an abstraction of database-specific functionality. For example, Database connector 1020 may convert structured data to a tabular format required by a relational database. In some embodiments, database connector 1020 adds and/or removes components of the data, for example metadata and identifiers, depending on the source and destination. In other embodiments, database connector encrypts data in transit to and from database 1064.

Database 1064 enables the persistent storage of information collected from the patient, HCP 592, device 500, external devices 572a, or third parties. The retrieval or storage of that information occurs using database connector 1020. In some embodiments, this data is encrypted while stored. Database 1064 may or may not be located on server 562.

FIG. 11 is an embodiment of HCP interface 566 accessed through terminal 557, and the software for which may be located and executed on this terminal, on server 562, or on any other system component or combination thereof. It can both send and receive data from database 565 on server 502, and communicate with device 500.

Figure 12:
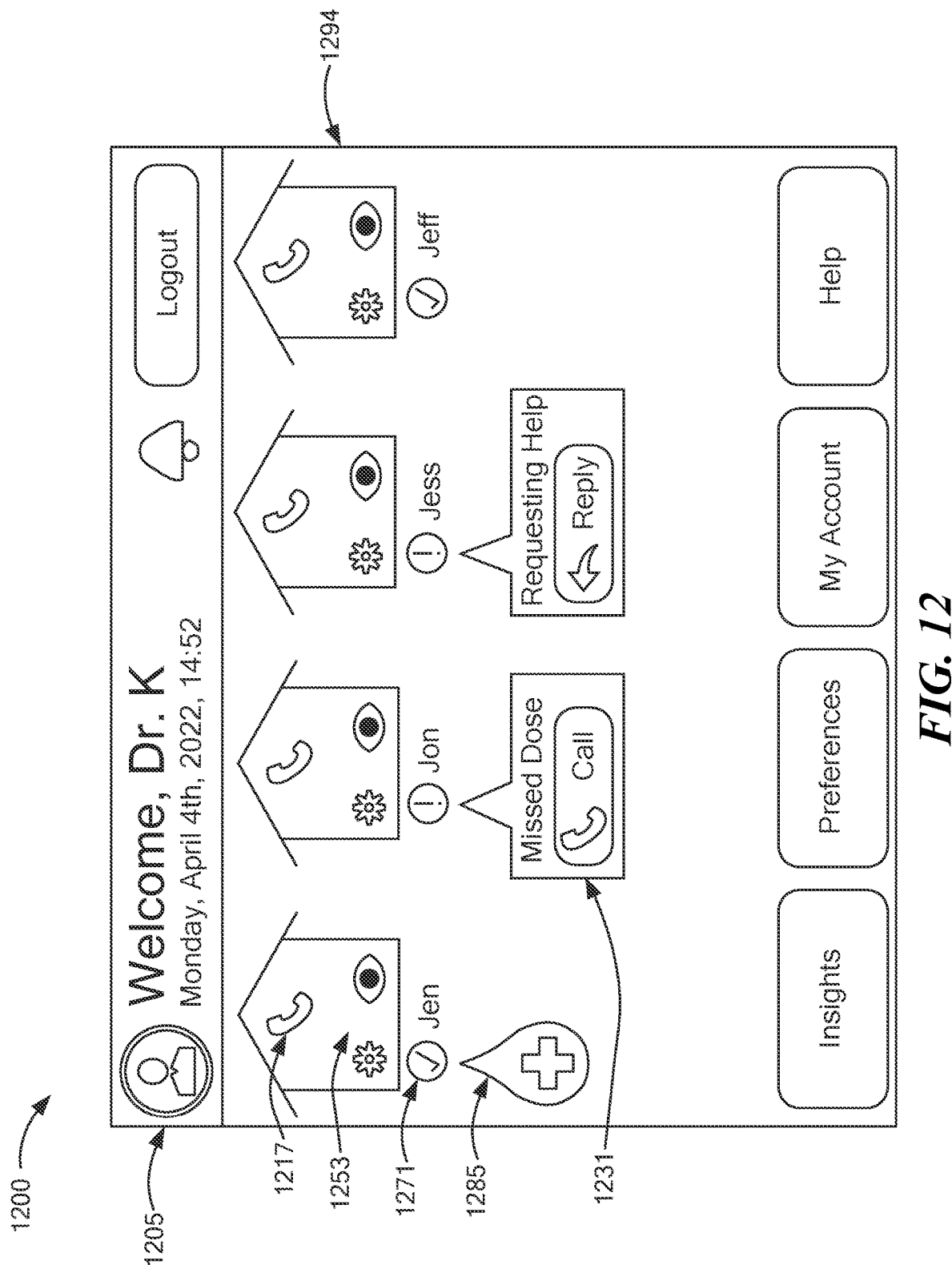
FIG. 12 is a display generated of an alternative embodiment of an HCP interface of the present invention.
Figure 13:
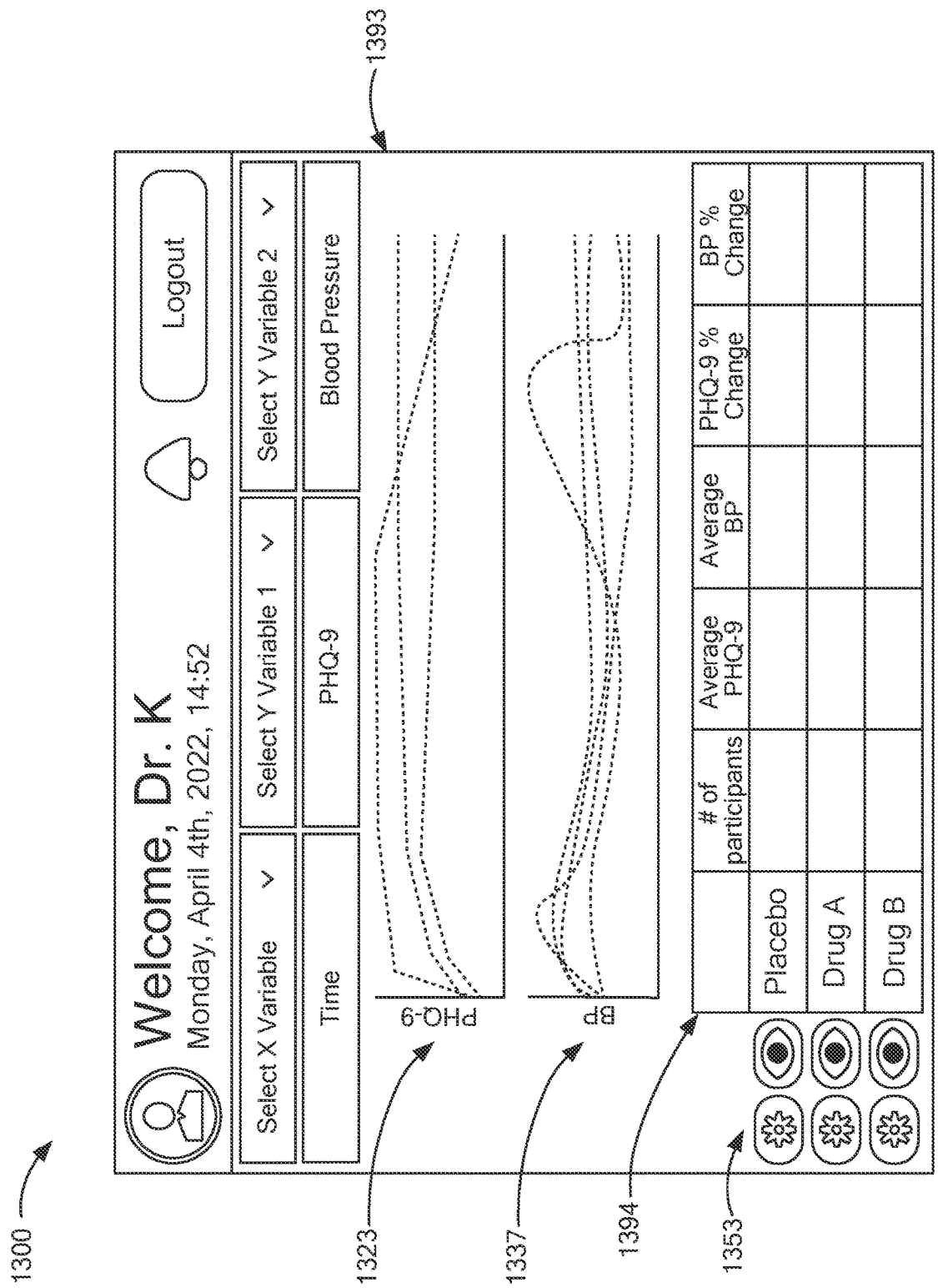
FIG. 13 is a display generated of an alternative embodiment of an HCP interface of the present invention.

Portal 1100 is one embodiment of HCP interface 566 specifically tailored to an HCP within a small medical practice with multiple patients using system 501. Other embodiments of interface 566 are shown in FIGS. 12 and 13, tailored to other applications.

Figure 11A:
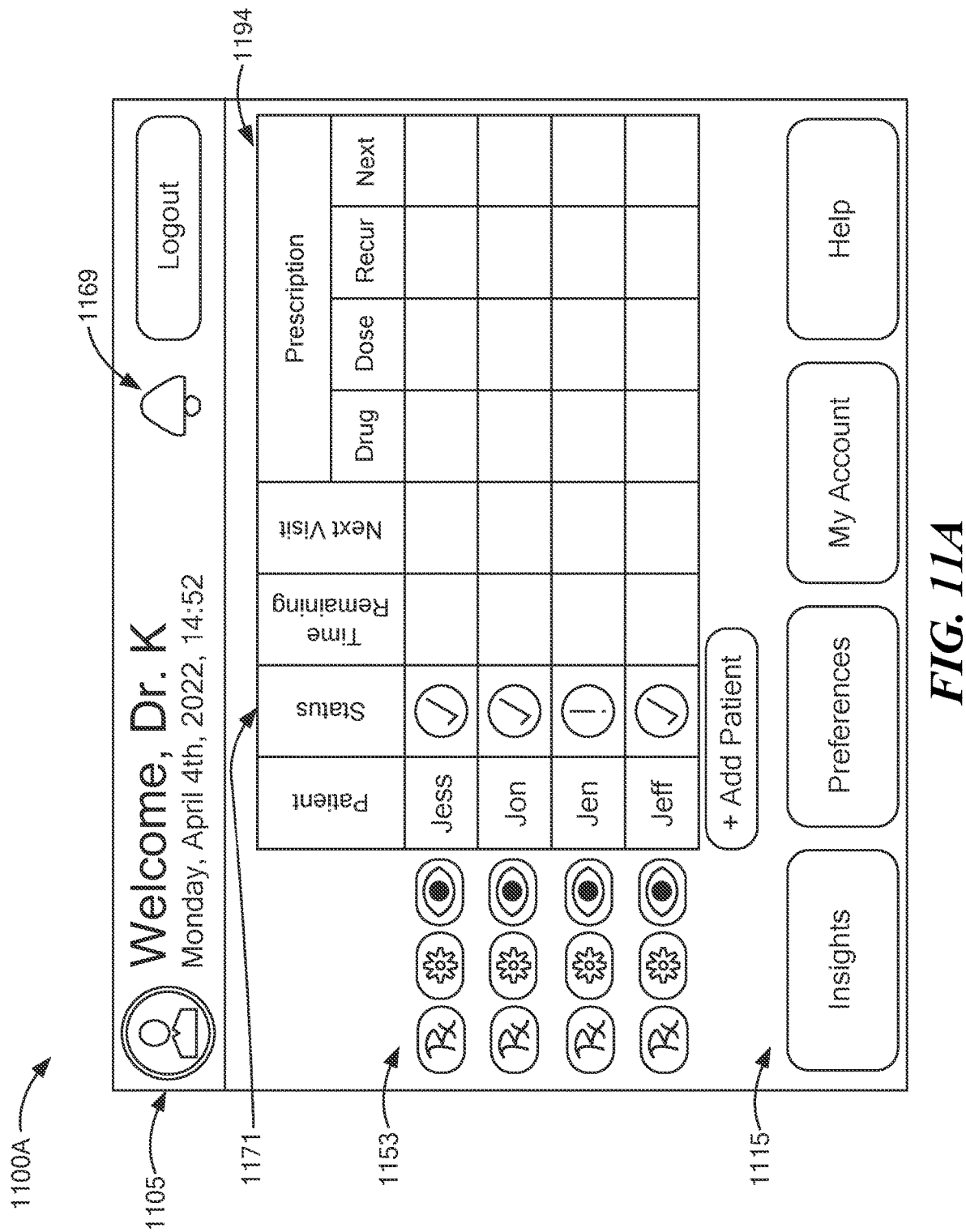
FIG. 11A-11D are displays generated by embodiments of an HCP interface of the present invention.

A home page 1100A for HCPs is presented in FIG. 11A. Home page 1100A has a header 1105 including the name of the HCP presently logged in, a drop-down notifications log 1169 for alerts such as tamper events, as well as a button for the HCP to logout, for example to allow for the same terminal to be used by multiple HCPs within the same medical practice.

Below header 1105 is list of patients 1194. List of patients 1194 contains every patient over which the logged-in HCP oversees, for example each in the practice or each patient to whom the logged-in HCP prescribes medication. Within list 1194 is patient status indicator 1171, which may be a check mark, for example should there be no concerns with the associated patient, or may be an exclamation point if there is a concern with a patient, for example a detected tamper event, missed dose, or prolonged lack of device internet connectivity. In some embodiments of list 1194, each patient's next dose time is is indicated, and in some such embodiments, when a dose time arrives, a button appears to allow the HCP to initiate an audio and/or video communication with the given patient in order to monitor their medication administration in real time. To the left of list of patients 1194 are control buttons 1153 which can be used to quickly create a new prescription or to view or modify patient details and settings.

Below list of patients 1194 is directory 1115 which allows the HCP to access various pages outside of the home page, such as those for viewing insights, modifying HCP account or other global settings, for example notification settings, or contacting a party in case of technical difficulties. Such a party could, for example, be the developer of portal 1100 or a third party.

Figure 11B:
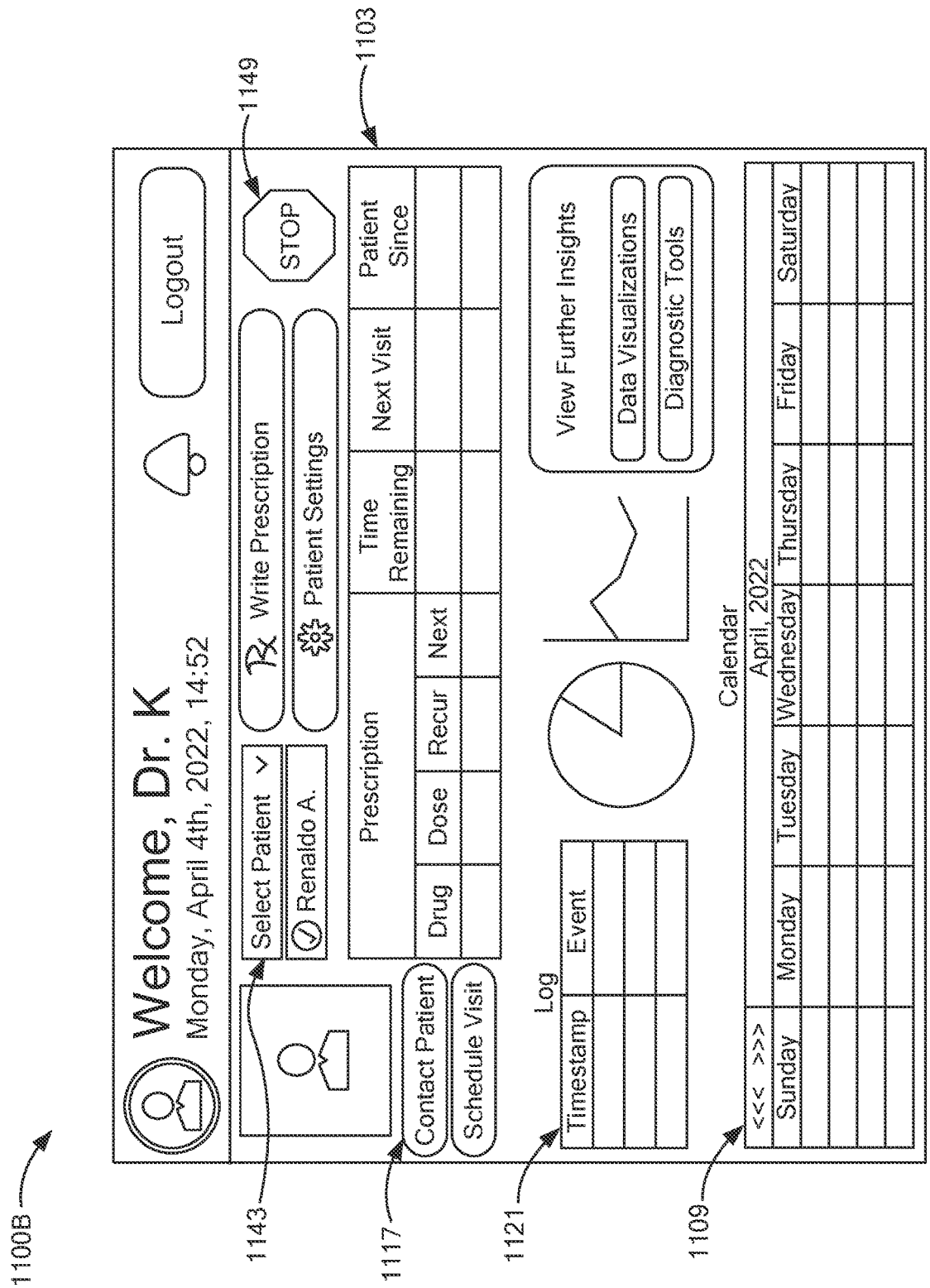

Patient overview page 1100B is presented in FIG. 11B. Below the header, patient overview page 1100B has a patient select drop down menu 1143, which allows the HCP to select the patient to view.

Below patient select 1143 is overview 1103, which displays an overview of the selected patient. Overview 1103 provides essential patient information to the HCP such as the current prescription, graphs that provide an overview on treatment progress, navigation buttons for creating a prescription, modifying settings, or viewing additional data, as well as contact buttons and an emergency stop button.

Within overview 1103 exists stop button 1149 which allows the HCP to disable the ability for the patient to administer a dose. Device shutdown command 549, as noted above with reference to FIG. 5, may be initiated using stop button 1149. Such a command is also referenced above with reference to FIG. 7 as a potential component of commands 590 as part of process 790.

On the bottom left-hand side of overview 1103 exists contact button 1117. When pressed, the patient will be contacted in some form, including but not limited to a voice call, a video call, email, or a text message, and in some embodiments, should multiple communication forms be available, a menu appears for the HCP to select which one to initiate.

Below patient overview 1103 exists event log 1121. Event log 1121 displays a patient's event history in a tabular form. The data within event log 1121 may include but is not limited to dose administration times, missed doses, and tamper events, along with relevant timestamps.

Below event log 1121 exists calendar 1109, providing an overview of the patient's treatment in the current month. The data within calendar 1109 may include but is not limited to data from event log 1121. Some events may be actionable. For the purpose of illustration, a tamper event may include a button to contact the patient's primary physician or family member. In the top left corner of calendar 1109 are navigation buttons to move forward or back in time to view months other than the present one.

Figure 11C:
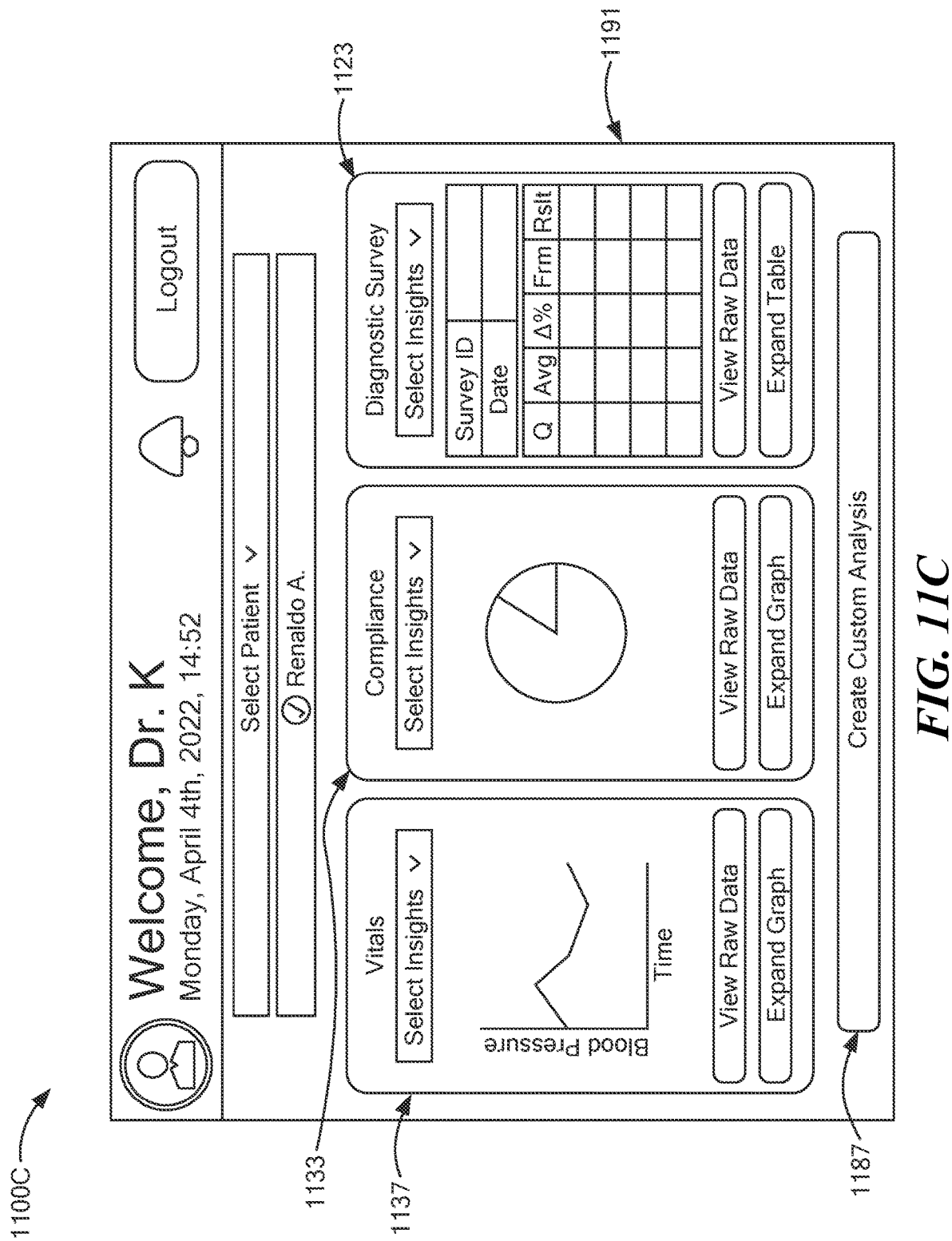

Patient analysis page 1100C is presented in FIG. 11C. Patient analysis page 1100C is where the HCP goes to view raw data or analyzed patient data.

Within patient analysis page 1100C exists analysis display 1191, which provides raw data or data visualizations of the patient's data which may include compliance, health parameters, survey results, or other treatment or biometric data. The data provided may be gathered through various sources, including but not limited to third parties and analysis 961. Components of analysis display 1191 may include embodiments of utilization 971. For example, patient-specific utilization 991 may be overlaid with bulk data utilization 993 to provide HCPs with comparisons between data from all patients and data from the selected patient. Such data may be displayed in any number of ways, which may vary based on the type of data being displayed, and may include but is not limited to tables, navigable databases, graphs such as bar graphs, line graphs, pie charts, box plots, scatter plots, distribution curves, and trend lines.

Within analysis display 1191 exists subsection 1137 dedicated to displaying health parameter raw data and/or data visualizations. These health parameters, in the embodiment of FIG. 11C, include vitals, with blood pressure over time chosen by the HCP as the desired visualization to display. This data may be generated from external devices 572a, third parties, from device 500, or may have been input by the patient via their interface. This may include for example blood pressure and heart rate. Trends in this data may be displayed for the HCP and may or may not be used to help them make educated diagnostic decisions. For example, a patient with a blood pressure trending higher over time may be removed from their medication if it is known to cause high blood pressure or perhaps be put on a blood pressure reducing medication.

Within analysis 1191, to the right of vitals 1137, exists a subsection dedicated to compliance 1133, which provides raw data or data visualizations on patient compliance during their treatment. This data may be used by HCPs to determine whether to continue treatment as is, take measures to improve compliance, or remove the patient from the medication entirely. Some measures which may be used to improve compliance may be requiring doses be taken while on a video conference with an HCP, a feature which also may be incorporated into embodiments of portals 1100 and 600.

To the right of compliance 1133 exists survey scores 1123. Survey scores 1123 displays a summary of, which in FIG. 11C is diagnostic, information collected from the patient. This may include answers to a particular survey, which may be averaged or calculated otherwise, trends in the responses over time, a comparison to the average score of multiple patients, and a result column displaying any conclusions that may be driven by the survey responses. Survey scores 1123 may include metadata, such as the survey ID, the last time the selected patient took the survey, and the survey response rate. Such data may for example be used to track outcome measures, which may provide the HCP with insight needed to optimize the treatment.

At the bottom of analysis display 1191 exists button 1187 to create custom analysis, which allows the HCP to create their own implementation of utilization 971 from raw or analyzed data that is patient-specific or not or a combination of both. For the purpose of illustration, this may include the ability to compare a patient's survey scores to known responses within a larger population, or viewing the correlation between dose times and biometrics collected from external devices 572a.

Figure 11D:
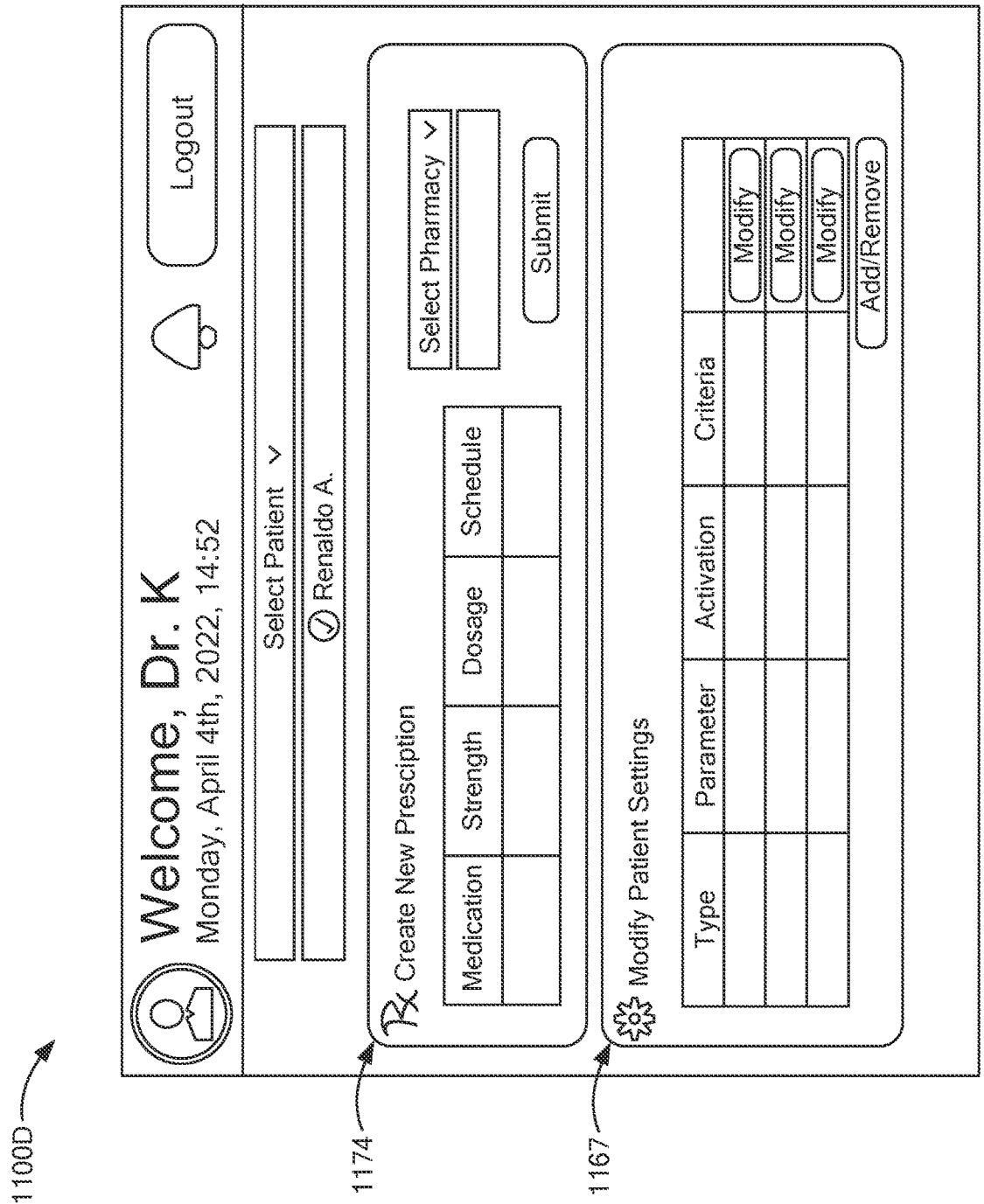

Patient settings page 1100D is presented in FIG. 11D. Patient settings page 1100D includes options to create a new prescription 1174 and modify settings 1167.

At the top of patient settings page 1100D exists tool 1174 to create a new prescription 574, for example as part of medication prescription step 774. Prescription writing tool 1174 allows the HCP to write a prescription for the patient for a given medication with a specified dose and schedule. Tool 1174 may include recommendations for the dose amount or schedule, perhaps taking into account biometric and compliance data collected from the patient, including but not limited to analysis 961 and data collected from external sources such as an EHR. In some embodiments, tool 1174 may integrate with pharmacies, such that the prescription may be automatically delivered, electronically or otherwise, to the patient's preferred pharmacy. Some embodiments may integrate with EHR systems, such as those found at pharmacies or hospitals, allowing information regarding the prescription to be added to said EHR.

Below tool 1174 exists a tool to modify patient settings 1167, which may include prerequisites 867, requirements after a dose is taken, data access controls, and contact information for relevant third parties. Examples of requirements that may be modified through tool 1167 include, but are not limited to which data needs to be input and what thresholds allow for a dose to be made available, which if any surveys may be given before or after a dose, and when an HCP should receive an automatic alert.

FIG. 12 is another embodiment of HCP interface 566, tailored for use in larger, controlled environments such as assisted living, senior communities, nursing homes, hospices, medical institutions, hospitals, or anywhere else which may benefit from providing a convenient way for nurses to actively monitor many patients simultaneously and manage their care more closely than may be desired by the HCP who chose to use the embodiment of FIG. 11.

Home page 1200 has a header 1205 including the name of the HCP presently logged in with a selection box to change who is presently using the portal, for example the nurse currently on shift monitoring elderly residents. Different nurses for example may have different sets of patients for whom they are responsible, and thus the indication of current user allows the portal to present them with the most relevant information. On the right hand side of header 1205 exists a lock button that will prevent unauthorized access.

Below header 1205 exists map 1294. Map 1294 may or may not map the physical location of patients onto the screen. For example, some alternative embodiments show a map of a hospital floor plan with navigation buttons to change which floor is being viewed, while the embodiment of FIG. 12 and others show a street view of houses with navigation around the neighborhood using click, hold and drag mouse functions. Map 1294 provides a visual overview of some or all patients managed by the HCP, along with essential information such as their status or notifications of requested help. The visualization may be modified to fit the needs of the HCP. For example, homes may be shown in the case of an assisted living facility. In a hospital setting, the HCP may instead use beds or rooms.

Within each patient domicile icon in map 1294 exists icons and buttons to manage the patient. Status identifier 1271 provides an outlook on the overall health and performance of a patient. For example, if a patient is requesting help or not in compliance, the status icon may change.

Above status icons 1271 exists call button 1217. This allows the HCP to directly communicate with the patient, for example through voice or video call.

Below status icons 1271 exists quick actions 1253, which allow the HCP to view an overview of the patient or modify patient settings.

Below quick control actions 1253 exists nurse location 1285. In some embodiments where map 1294 physically maps the location of patients onto the screen, nurse location 1285 allows the HCP, patient, or relevant third parties to track the location of the HCP. Nurse location 1285 may be used to optimize pathing for the HCP depending on factors such as the locations and status of patients, traffic, or any other relevant factors.

To the right of nurse location 1285 exists alert notification 1231. Alerts may occur automatically or may be triggered manually by the patient, HCP or third party. For example, a patient may be unable to administer a dose and requests help. Some notifications may be actionable, for example in the case of a missed dose a call button may appear. These actions may be different based on the generated notification.

FIG. 13 is another embodiment of HCP interface 566, tailored towards use for bulk data utilization 993, for example by HCPs managing a clinical trial, pharmaceutical companies studying drugs in development or monitoring drugs in use by the public, and insurance companies looking for trends to inform policies and/or to guide investment.

Page 1300 is an embodiment specifically intended for use with a clinical trial, and has a layout optimized for viewing trends amongst patients in different treatment groups to help analyze which treatments are working best for who and what side effects may be occurring and why. Other embodiments may be tailored for use by an HCP that is not involved in clinical trials but simply wants to compare their own patients, for example through use of custom analysis function 1187.

Data visualization 1393 displays graphical trends to help HCPs visualize the progress of the treatment and the health and compliance of their patients. This may be in the form of raw or previously analyzed data, and may include trendlines, statistical analysis, distributions, or other visualized analyses which may benefit the HCP. Patients may be split up into groups. For the purpose of illustration, a clinical trial may want to split patients into groups for each medication being tested along with a placebo or other control groups.

Within data visualizations 1393 exists performance metrics 1323 which displays data collected from the patient intended to measure treatment progress. Patients may be grouped by the drug they are taking, or any number of factors, such that the HCP can compare progress using a variety of independent variables.

Below performance metrics 1323 exists vitals 1337 which displays vitals data collected from all patients. This information may be colored or otherwise differentiated based on treatment or any number of factors. Vitals 1337 may indicate anomalies or trends within the dataset. Such data may for example drive decisions by a pharmaceutical company in regards to suggested dosing, side effect warnings, risks to certain demographics, and indications for use.

Table 1394 displays groupings of patients along with performance metrics, compliance information, or any number of metrics relevant to the HCP. Information may be highlighted, such as any indication that data may be skewed, for example due to poor compliance by a participant.

To the left of table 1394 exists quick actions 1353, which allows the HCP to view each grouping or modify settings for a particular grouping. For example, if one treatment is deemed too dangerous to continue testing, the HCP may opt to disable the administration of doses for all devices utilizing said treatment.

System 501 may contain a distributed network of multiple instances of HCP interface 566, where each interface instance is either uniform or separate and distinct, for example adjusted to the needs of each individual HCP 592 within the system. For example, one the patient's doctor may use an interface similar to that of FIG. 11, while a nurse who cares for that patient may use an interface similar to that of the embodiment of FIG. 12, further while the oversight board of a clinical trial in which the patient is participating may use an interface similar to that of the embodiment of FIG. 13. For the purpose of illustration, a practice may include many physicians who maintain their own set of patients and thus system 501 configured such that analyses utilization 971 may be able to be accessed by multiple HCP interfaces 566, each with the same or different sets of analyses. Other components of system 501 may also be distributed in the location of their data storage and processing, including but is not limited to patient interface 570, server 562, patient management software 561, analysis 961, backend 1062, backend logic 1061, database 564, and note that each of these system components may be distributed in different ways and between different locations.

It should be appreciated that various embodiments may be formed with one or more of the above-described features. The above aspects and features may be employed in any suitable combination as the present invention is not limited in this respect. It should also be appreciated that the drawings illustrate various components and features which may be incorporated into various embodiments. For simplification, some of the drawings may illustrate more than one optional feature or component. It should also be appreciated that the present invention is not limited to the specific embodiments disclosed in the drawings. It should be recognized that the invention encompasses embodiments which may include only a portion of the components described above and/or illustrated in any of the referenced drawings, and/or may also encompass embodiments combining components illustrated in multiple different drawing figures.

The present application is a continuation-in-part of pending U.S. patent application Ser. No. 17/461,837, filed Aug. 30, 2021, which is a continuation of Ser. No. 16/897,232, filed Jun. 9, 2020, now issued as U.S. Pat. No. 11,103,422, which claims the benefit of U.S. Provisional Patent Application 62/859,138, filed Jun. 9, 2019, all of which are hereby incorporated by reference herein in their entireties.

It should be understood that the foregoing description of various embodiments is intended merely to be illustrative thereof and that other embodiments, modifications, and equivalents are within the scope of the invention recited in the claims appended hereto.

What is claimed is:

1. A distributed system for enabling remote oversight and control over a self-administration of medication by a patient, comprising:
   a device for use by the patient to self-administer a prescribed medication comprising a monitored subassembly having at least two sensors connected to said device to detect device parameters including detected attempts to tamper with the device and detected events of medication self-administration, and to remotely transmit said detected device parameters, and a command subassembly configured to control the device and its use to mitigate a risk associated with patient self-administration of potentially dangerous in response to remotely-generated commands received by the device; and
   a patient management software program stored on a non-transitory computer-readable storage medium, executing on a remote server communicably coupled to said device, wherein said patient management software program receives said transmitted detected device parameters, stores and analyzes the detected device parameters for subsequent presentation to a health care provider (HCP), and further configured to generate said commands in response to the HCP and to transit said commands to the device.

2. The system of claim 1, wherein said device delivers a medication in one or more of the following delivery mechanisms:
- nasal spray;
- inhaler;
- transdermal patch;
- intravenous injection;
- intramuscular injection; and
- eye drop.

3. The system of claim 1, wherein said medication is in one or more of the following forms:
- aerosol;
- mist;
- vapor;
- smoke;
- powder; and
- gel.

4. The system of claim 1, further comprising a computational analysis of any data which exists within the system.

5. The system of claim 4, wherein said analysis is conducted on data collected from, and said analysis is utilized by, one or more of:
- patient;
- health care provider;
- device; and
- external system.

6. The system of claim 5, wherein said external system comprises one or more of:
- pharmacy system;
- insurance system;
- government system;
- drug manufacturer;
- drug delivery device manufacturer;
- sensor device manufacturer;
- healthcare software developer;
- research institution;
- electronic medical records system; and
- hospital system.

7. The system of claim 4, wherein said analysis comprises one or more of:
- data from a single patient; and
- data from many patients.

8. The system of claim 4, wherein said analysis comprises one or more of:
- tracking patient use of the device,
- patient adherence to schedule;
- patient medical conditions;
- patient side-effects related to taking the medication;
- survey results over time;
- treatment progress;
- compliance;
- health parameters;
- sensor data;
- correlations and trends amongst variables;
- drug comparisons;
- trial participant grouped data; and
- accepted standards.

9. The system of claim 4, wherein said presentation of analysis is used for one or more of:
- monitoring patient adherence to dose schedule;
- optimization of patient treatment;
- surveillance of potential health risks;
- diagnostics;
- assessing the efficacy of a medication;
- assessing the safety of a medication; and
- assessing cost-benefit analysis of a treatment.

10. The system of claim 1, wherein a computing platform is accessible to the health care provider (HCP) and communicably connected to the server, and further wherein the system comprises:
- a HCP interface program, executing on the platform, comprising data presentation means for monitoring information being related to the patient and the patient's use of said device;
- wherein said HCP interface program comprising data collection means for receiving information entered by the HCP, said information being related to device control; and
- wherein said HCP interface is configured to transmit said HCP-entered information to said patient management software executing on the server to generate said commands in response to the HCP and to transit said commands to the device.

11. The system of claim 10, wherein said commands comprise one or more of:
- a single dose quantity of the medication;
- a dosing schedule;
- permit access to the device for prescription refills;
- cease operability of the device; and
- prerequisites.

12. The system of claim 10, wherein said HCP interface program wherein HCP interface is designed for use by:
- private practice;
- hospital;
- assisted living facility;
- clinical testing site;
- government health service;
- pharmaceutical company;
- device company; and
- insurance company.

* * * * *